United States Patent
Thomas et al.

(10) Patent No.: US 10,774,073 B2
(45) Date of Patent: Sep. 15, 2020

(54) COMPOSITIONS AND METHODS FOR TREATING INFECTIONS

(71) Applicant: Vyera Pharmaceuticals, LLC, New York, NY (US)

(72) Inventors: Stephen B. Thomas, New York, NY (US); Allen T. Hopper, Lexington, MA (US); Matthew Welsch, New Haven, CT (US)

(73) Assignee: Vyera Pharmaceuticals, LLC, New York, NY (US)

( * ) Notice: Subject to any disclaimer, the term of this patent is extended or adjusted under 35 U.S.C. 154(b) by 0 days.

(21) Appl. No.: 16/075,924

(22) PCT Filed: Feb. 2, 2017

(86) PCT No.: PCT/US2017/016224
§ 371 (c)(1),
(2) Date: Aug. 6, 2018

(87) PCT Pub. No.: WO2017/136556
PCT Pub. Date: Aug. 10, 2017

(65) Prior Publication Data
US 2019/0077794 A1 Mar. 14, 2019

Related U.S. Application Data

(60) Provisional application No. 62/375,712, filed on Aug. 16, 2016, provisional application No. 62/291,900, filed on Feb. 5, 2016.

(51) Int. Cl.
*C07D 401/04* (2006.01)
*C07D 403/14* (2006.01)
*C07D 403/04* (2006.01)
*C07D 239/50* (2006.01)
*C07D 401/12* (2006.01)
*C07D 405/12* (2006.01)
*C07D 403/12* (2006.01)
*A61P 33/02* (2006.01)
*C07D 401/14* (2006.01)
*C07D 405/14* (2006.01)

(52) U.S. Cl.
CPC ............ *C07D 403/14* (2013.01); *A61P 33/02* (2018.01); *C07D 239/50* (2013.01); *C07D 401/04* (2013.01); *C07D 401/12* (2013.01); *C07D 401/14* (2013.01); *C07D 403/04* (2013.01); *C07D 403/12* (2013.01); *C07D 405/12* (2013.01); *C07D 405/14* (2013.01)

(58) Field of Classification Search
CPC .. C07D 403/14; C07D 239/50; C07D 401/04; C07D 401/12; C07D 401/14; C07D 403/04; C07D 403/12; C07D 405/12; C07D 405/14; A61P 33/02
See application file for complete search history.

(56) References Cited

U.S. PATENT DOCUMENTS

| | | | | |
|---|---|---|---|---|
| 4,532,240 A * | 7/1985 | Werbel | ................. | C07D 239/42 514/252.14 |
| 4,774,249 A * | 9/1988 | Kompis | ............... | C07D 211/70 514/272 |
| 2004/0006042 A1* | 1/2004 | Berry | ................... | A61K 31/505 514/50 |

FOREIGN PATENT DOCUMENTS

| | | | | |
|---|---|---|---|---|
| EP | 0103464 A2 | 3/1984 | | |
| EP | 0122580 A1 | 10/1984 | | |
| WO | WO-00/09131 A1 | 2/2000 | | |
| WO | WO-0009131 A1 * | 2/2000 | ............. | A61K 45/06 |
| WO | WO-2017/136556 A1 | 8/2017 | | |
| WO | WO-2019/032458 A1 | 2/2019 | | |
| WO | WO-2019032458 A1 * | 2/2019 | ........... | C07D 239/50 |

OTHER PUBLICATIONS

S. Cole, 26 Cancer Chemotherapy and Pharmacology, 250-256 (1990) (Year: 1990).*
M. Welsch et al., 7 Medicinal Chemistry Letters, 1124-1129 (2016) (Year: 2016).*
CAS Abstract of U.S. Pat. No. 4,774,249 (1988) (Year: 1988).*
CAS Abstract of U.S. Pat. No. 4,532,240 (1985) (Year: 1985).*
H. Nahrevanian et al., 11 Journal of Natural Remedies, 167-176 (2011) (Year: 2011).*
L.M. Werbel et al., Chemistry and Biology of Pteridines, 69-71 (1986) (Year: 1986).*
M. Parenti et al., 47 Journal of Medicinal Chemistry, 4258-4267 (2004) (Year: 2004).*
R. Moran et al., 36 Molecular Pharmacology, 736-743 (1989) (Year: 1989).*
R. McLeod et al., Human Toxoplasma Infection in, Toxoplasma Gondii (Academic Press, 2014) (Year: 2014).*
A. Rosowsky et al., 47 Journal of Medicinal Chemistry, 1474-1486 (2004) (Year: 2004).*
A. Rosowsky et al., 45 Journal of Medicinal Chemistry, 233-241 (2002) (Year: 2002).*
Allegra et al., "Potent in Vitro in Vivo Antitoxoplasma Activity of the Lipid-soluable Antifolate Trimetrexate," The Journal of Clinical Investigation, 79(2):478-482 (1987).
Bowman et al., "Protein Flexibility and Species Specificity in Structure-Based Drug Discovery: Dihydrofolate Reductase as a Test System," J Am Chem Soc, 129(12): 3634-3640 (2007) and Supplemental Information.
Chae et al., "Novel Receptor Surface Approach for 3D-QSAR: The Weighted Probe Interaction Energy Method," J Chem Inf Comput Sci, 44(5): 1774-1787 (2004).
(Continued)

*Primary Examiner* — Alexander R Pagano
(74) *Attorney, Agent, or Firm* — Foley Hoag LLP; David P. Halstead; Lucas P. Watkins

(57) ABSTRACT

The invention relates to inhibitors of dihydrofolate reductase and pharmaceutical preparations thereof. The invention further relates to methods of treatment of parasitic infections, such as *T. gondii, T. cruzi, P. falciparum, T. brucei,* or *L. major* infections, using the novel inhibitors of the invention.

21 Claims, No Drawings

(56) References Cited

OTHER PUBLICATIONS

Cheng et al., "Studies of the Inhibition of Bovine Liver Dihydrofolate Reductase by Pyrimidine Compounds," J Food Drug Anal, 2(4): 265-270 (1994).
Cole, "Patterns of Cross-Resistance in a Multidrug-Resistant Small-Cell Lung Carcinoma Cell Line," Cancer Chemother Pharmacol, 26(4): 250-256 (1990).
Database Registry Chemical Abstracts, Database Accession No. (1350098-74-6), CAS Registry No. (1350098-74-6), (Dec. 7, 2011).
Database Registry Chemical Abstracts, Database Accession No. (907967-86-6), CAS Registry No. (907967-86-6), (Sep. 20, 2006).
Database Registry Chemical Abstracts, Database Accession No. (912483-00-2), CAS Registry No. (912483-00-2), (Nov. 20, 2006).
Database Registry Chemical Abstracts, Database Accession No. (912537-53-2), CAS Registry No. (912537-53-2), (Nov. 6, 2006).
Database Registry Chemical Abstracts, Database Accession No. (959253-99-7), CAS Registry No. (959253-99-7), (Dec. 21, 2007).
Doweyko, "The Hypothetical Active Site Lattice. An Approach to Modelling Active Sites from Data on Inhibitor Molecules," J Med Chem, 31(7): 1396-1406 (1988).
International Search Report and Written Opinion for International Application No. PCT/US2018/045389 dated Nov. 14, 2018.
Kinnamon et al., "Polyamines: Agents with Macrofilaricidal Activity," Ann Trop Med Parasit, 93(8): 851-858 (1999).
Maag et al., "94. 5-(N-Arylnortropan-3-yl)-and 5-(N-Arylpiperidin-4-yl)-2,4-diaminopyrimidines. Novel Inhibitors of Dihydrofolate Reductase," Helv Chim Acta, 69(4): 887-897 (1986).
Moran et al., "Relative Substrate Activities of Structurally Related Pteridine, Quinazoline, and Pyrimidine Analogs for Mouse Liver Folypolyglutamate Synthetase," Mol Pharmacol, 36(5): 736-743 (1989).
Parenti et al., "Three-Dimensional Quantitative Structure—Activity Relationship Analysis of a Set of Plasmodium Falciparum Dihydrofolate Reductase Inhibitors Using a Pharamcophore Generation Approach," J Med Chem, 47(17): 4258-4267 (2004).
Welsch et al., "Discovery of Potent and Selective Leads against Toxoplasma gondii Dihydrofolate Reductase via Structure-Based Design," ACS Med Chem Lett, 7(12): 1124-1129 (2016).
Werbel et al., "In Vivo and In Vitro Evaluation of 5-[4-(Substituted Aryl)-1-Piperazinyl]-6-Alkyl-2,4-Pyrimidinediamines as Antitumor Agents," Chemistry and Biology of Pteridines, 69-71 (1986).
Extended European Search Report for EP Application No. 17748159.5 dated Jun. 13, 2019.
Bohm et al., "Three-dimensional quantitative structure-activity relationship analyses using comparative molecular field analysis and comparative molecular similarity indices analysis to elucidate selectivity differences of inhibitors binding to trypsin, thrombin, and factor Xa," J. Med. Chem., 42:458-477 (1999).

\* cited by examiner

COMPOSITIONS AND METHODS FOR TREATING INFECTIONS

RELATED APPLICATIONS

This application is a U.S. National Stage of International Patent Application No. PCT/US2017/016224, filed Feb. 2, 2017, which claims the benefit of U.S. Provisional Application No. 62/291,900, filed on Feb. 5, 2016, and U.S. Provisional Application No. 62/375,712, filed on Aug. 16, 2016, the entire teachings of each of which are incorporated herein by reference.

BACKGROUND OF THE INVENTION

Parasitic protozoan infections are a major concern for human health. Toxoplasmosis is a parasitic infection caused by *Toxoplasma gondii* (*T. gondii*). Although toxoplasmosis is most often asymptomatic, persons infected with toxoplasmosis can experience severe symptoms, including seizures, poor coordination, lung damage, eye damage, and brain damage, and the infection in immunocompromised patients is often fatal if not treated. Other parasitic protozoan infections include leishmaniasis (also known as leishmaniosis), caused by protozoans of genus *Leishmania*, including *Leishmania major* (*L. major*) *Leishmania tropica* (*L. tropica*), *Leishmania brasihensis* (*L. brasiliensis*), and *Leishmania donovani* (*L. donovani*); Chagas disease, caused by the protozoan *Trypanosoma cruzi* (*T. cruzi*); Human African Trypanosomiasis (also known as HAT and African sleeping sickness), caused by the protozoan *Trypanosoma brucei* (*T. brucei*); and Malaria, caused by protozoans of genus *Plasmodium*, including *Plasmodium falciparum* (*P. falciparum*).

Existing treatment for toxoplasmosis include administration of pyrimethamine, usually in combination with a DHPS sulfonamide inhibitor (e.g., sulfadiazine) to improve efficacy and leucovorin to improve tolerability. Allergic reactions to sulfonamide drugs are common and therefore some patients are not able to receive the combination therapy. Pyrimethamine treatment may cause severe side-effects and toxicity, including nausea, vomiting, leukopenia, bone marrow toxicity, teratogenicity and central nervous system toxicity. Mechanism-based toxicity of DHFR inhibition in mammalian, including human, cells can be partially alleviated by administration of leucovorin to selectively replace tetrahydrofolate in mammalian cells.

Pyrimethamine acts by inhibiting the enzyme dihydrofolate reductase (DHFR). The $IC_{50}$ for pyrimethamine against *T. gondii* DHFR (tgDHFR) is 0.76 μM, while that against human DHFR (hDHFR) is 5.8 μM. (Allegra et al., J. Clin. Investigation. 1987, 79, 478-482.) Thus, although pyrimethamine inhibits tgDHFR more potently than hDHFR, the selectivity ratio for tgDHFR—less than 10—is relatively low. Therefore, clinically relevant doses of pyrimethamine result in plasma concentrations that effectively inhibit hDHFR, leading to many of the observed mechanism-based side effects of pyrimethamine. Furthermore, the relatively high $IC_{50}$ for pyrimethamine against tgDHFR requires greater concentrations in plasma for efficacy, which may cause additional, off-target induced side effects.

Thus, there is a need for compounds that are both more potent inhibitors of tgDHFR and more selective inhibitors of tgDHFR over hDHFR. Likewise, there is also a need for potent and selective DHFR inhibitors against *Leishmania, T. cruzi, T. brucei* and *Plasmodium* for the treatment of leishmaniasis, Chagas disease, African Trypanosomiasis, and Malaria, respectively.

SUMMARY OF THE INVENTION

In certain embodiments, the present invention relates to compounds having the structure of formula (I):

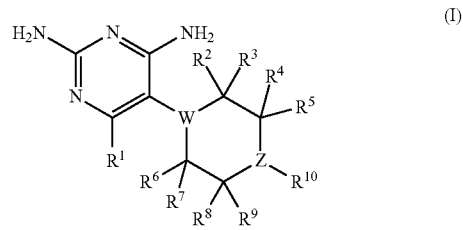

wherein:
$R^1$ is H, $C_{1-6}$ alkyl, $C_{3-6}$ cycloalkyl, $C_{4-8}$ cycloalkylalkyl, or halogen;
W is N or $CR^{18}$ and Z is N or $CR^{17}$, provided that at least one of W and Z is N;
$R^2$, $R^3$, $R^4$, $R^5$, $R^6$, $R^7$, $R^8$, $R^9$, $R^{17}$, and $R^{18}$ are independently selected from H, $C_{1-6}$ alkyl, $C_{3-6}$ cycloalkyl, hydroxyl or fluorine; provided that at least four of $R^2$, $R^3$, $R^4$, $R^5$, $R^6$, $R^7$, $R^8$, and $R^9$ are H; if W is N, then none of $R^2$, $R^3$, $R^6$, and $R^7$ is hydroxyl; and if Z is N, then none of $R^4$, $R^5$, $R^8$, and $R^9$ is hydroxyl;
$R^{10}$ is substituted or unsubstituted $C_{6-10}$ aryl or 5- to 10-membered heteroaryl;
or a pharmaceutically acceptable salt and/or prodrug thereof.

The invention further relates to pharmaceutical compositions of such compounds, as well as methods of using such compounds to treat infections (e.g., parasitic infections, such as toxoplasmosis).

DETAILED DESCRIPTION OF THE INVENTION

In one aspect, the present invention relates to compounds having the structure of formula (I):

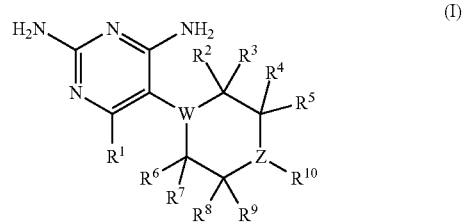

In formula (I):
$R^1$ is H, $C_{1-6}$ alkyl, $C_{3-6}$ cycloalkyl, $C_{4-8}$ cycloalkylalkyl, or halogen;
W is N or $CR^{18}$ and Z is N or $CR^{17}$, provided that at least one of W and Z is N;
$R^2$, $R^3$, $R^4$, $R^5$, $R^6$, $R^7$, $R^8$, $R^9$, $R^{17}$, and $R^{18}$ are independently selected from H, $C_{1-6}$ alkyl, $C_{3-6}$ cycloalkyl, hydroxyl or fluorine; provided that at least four of $R^2$, $R^3$, $R^4$, $R^5$, $R^6$, $R^7$, $R^8$, and $R^9$ are H; if W is N, then none of $R^2$, $R^3$, $R^6$, and $R^7$ is hydroxyl; and if Z is N, then none of $R^4$, $R^5$, $R^8$, and $R^9$ is hydroxyl;

$R^{10}$ is substituted or unsubstituted $C_{6-10}$ aryl or 5- to 10-membered heteroaryl;

or a pharmaceutically acceptable salt and/or prodrug thereof.

In certain embodiments, W is N and Z is $CR^{17}$. In certain such embodiments, $R^2$, $R^3$, $R^6$, and $R^7$ are independently selected from H, $C_{1-6}$ alkyl, $C_{3-6}$ cycloalkyl, or fluorine; and $R^4$, $R^5$, $R^8$, $R^9$, and $R^{17}$ are independently selected from H, $C_{1-6}$ alkyl, $C_{3-6}$ cycloalkyl, hydroxyl or fluorine.

In certain embodiments, W is $CR^{18}$ and Z is N. In certain such embodiments, $R^2$, $R^3$, $R^6$, $R^7$, and $R^{18}$ are independently selected from H, $C_{1-6}$ alkyl, $C_{3-6}$ cycloalkyl, hydroxyl, or fluorine; and $R^4$, $R^5$, $R^8$, and $R^9$ are independently selected from H, $C_{1-6}$ alkyl, $C_{3-6}$ cycloalkyl, or fluorine.

In certain preferred embodiments, W is N and Z is N. In certain such embodiments, $R^2$, $R^3$, $R^4$, $R^5$, $R^6$, $R^7$, $R^8$, and $R^9$ are independently selected from H, $C_{1-6}$ alkyl, $C_{3-6}$ cycloalkyl, or fluorine.

In certain embodiments, the compound has the structure of formula (Ia):

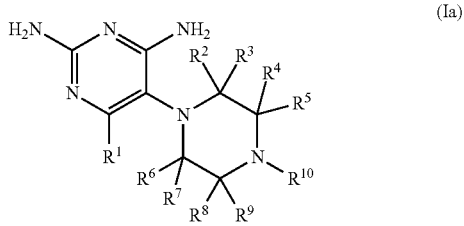

(Ia)

wherein:

$R^1$ is H, $C_{1-6}$ alkyl, $C_{3-6}$ cycloalkyl, or halogen;

$R^2$, $R^3$, $R^4$, $R^5$, $R^6$, $R^7$, $R^8$, and $R^9$ are independently selected from H, $C_{1-6}$ alkyl, $C_{3-6}$ cycloalkyl, or fluorine, provided that at least four of $R^2$, $R^3$, $R^4$, $R^5$, $R^6$, $R^7$, $R^8$, and $R^9$ are H;

$R^{10}$ is substituted or unsubstituted $C_{6-10}$ aryl or 5- to 10-membered heteroaryl;

or a pharmaceutically acceptable salt and/or prodrug thereof.

In certain embodiments, substituents on $R^{10}$ are selected from alkyl, cycloalkyl, halogen (e.g., fluoro), hydroxyl, alkoxy, cycloalkyloxy, cycloalkylalkyl, cycloalkylalkoxy, phosphoryl, phosphate, phosphonate, phosphinate, amino, amidine, imine, cyano, azido, sulfhydryl, or alkylthio, heterocyclyl, aralkyl, or an aromatic or heteroaromatic moiety. In certain embodiments, substituents on $R^{10}$ are selected from alkyl, cycloalkyl, halogen (e.g., fluoro), hydroxyl, alkoxy, cycloalkyloxy, cycloalkylalkyl, cycloalkylalkoxy, amino, amidine, imine, cyano, azido, sulfhydryl, or alkylthio, heterocyclyl, aralkyl, or an aromatic or heteroaromatic moiety. In certain preferred embodiments, $R^{10}$ is not substituted with carbonyl. In certain preferred embodiments, $R^{10}$ is not substituted with ethenyl, acyl, amide, ester, carboxylic acid, sulfonamide, sulfate, sulfone, sulfonate, sulfoxide, nitro, oxime, hydrazide, or hydrazone.

In certain embodiments, $R^{10}$ is substituted with at least one substituent selected from alkyl, cycloalkyl, halogen (e.g., fluoro), hydroxyl, alkoxy, cycloalkyloxy, cycloalkylalkyl, cycloalkylalkoxy, phosphoryl, phosphate, phosphonate, phosphinate, amino, amidine, imine, cyano, azido, sulfhydryl, or alkylthio, heterocyclyl, aralkyl, or an aromatic or heteroaromatic moiety. In certain embodiments, $R^{10}$ is substituted with at least one substituent selected from alkyl, cycloalkyl, halogen (e.g., fluoro), hydroxyl, alkoxy, cycloalkyloxy, cycloalkylalkyl, cycloalkylalkoxy, amino, amidine, imine, cyano, azido, sulfhydryl, or alkylthio, heterocyclyl, aralkyl, or an aromatic or heteroaromatic moiety. In certain preferred embodiments, $R^{10}$ is substituted with at least one substituent selected from alkyl, cycloalkyl, halogen (e.g., fluoro), hydroxyl, alkoxy, cycloalkyloxy, cycloalkylalkyl, cycloalkylalkoxy, heterocyclyl, aralkyl, or an aromatic or heteroaromatic moiety. In certain preferred embodiments, $R^{10}$ is substituted with at least one substituent selected from alkyl, cycloalkyl, halogen (e.g., fluoro), hydroxyl, alkoxy, cycloalkyloxy, cycloalkylalkyl, cycloalkylalkoxy, heterocyclyl, aralkyl, or an aromatic or heteroaromatic moiety. In certain preferred embodiments, $R^{10}$ is not substituted with carbonyl. In certain preferred embodiments, $R^{10}$ is not substituted with ethenyl, acyl, amide, ester, carboxylic acid, sulfonamide, sulfate, sulfone, sulfonate, sulfoxide, nitro, oxime, hydrazide, or hydrazone.

In certain embodiments, $R^{10}$ is substituted or unsubstituted $C_{6-10}$ aryl or 5- to 10-membered heteroaryl, and is further substituted with $R^{12}$ or $X-R^{12}$;

each instance of $R^{12}$ is independently selected from substituted or unsubstituted phenyl, 5- or 6-membered heteroaryl, or 4 to 7-membered heterocyclyl;

each instance of X is independently selected from carbonyl, Y, —$CH_2Y$—, or —$YCH_2$—;

each instance of Y is independently selected from —$CH_2$—, —O—, —S—, or —$N(R^{13})$—; and each instance of $R^{13}$ is independently H or $C_{1-6}$ alkyl.

In certain embodiments, $R^{10}$ is $C_{6-10}$ aryl or 5- to 10-membered heteroaryl, optionally substituted with one or more substituents independently selected from $R^{11}$, $R^{12}$, or $X-R^{12}$;

each instance of $R^{11}$ is independently selected from $C_{1-6}$ alkyl, $C_{1-6}$ alkoxy, $C_{2-6}$ alkoxyalkyl, $C_{3-6}$ cycloalkyl, $C_{3-6}$ cycloalkyloxy, $C_{4-8}$ cycloalkylalkyl, $C_{4-8}$cycloalkylalkoxy, cyano, or halogen;

each instance of $R^{12}$ is independently selected from substituted or unsubstituted phenyl, 5- or 6-membered heteroaryl, or 4 to 7-membered heterocyclyl;

each instance of X is independently selected from carbonyl, Y, —$CH_2Y$—, or —$YCH_2$—;

each instance of Y is independently selected from —$CH_2$—, —O—, —S—, or —$NR^{13}$—; and each instance of $R^{13}$ is independently H or $C_{1-6}$ alkyl.

In certain embodiments, $R^{10}$ is substituted by no more than one $R^{12}$ or $X-R^{12}$. In certain embodiments, $R^{10}$ is substituted by one $R^{12}$. In certain embodiments, $R^{10}$ is substituted by one $X-R^{12}$.

In certain embodiments, $R^{10}$ is $C_{6-10}$ aryl or 5- to 10-membered heteroaryl, and is optionally substituted with a substituent selected from alkyl, cycloalkyl, halogen (e.g., fluoro), hydroxyl, alkoxy, cycloalkyloxy, cycloalkylalkyl, cycloalkylalkoxy, phosphoryl, phosphate, phosphonate, phosphinate, amino, amidine, imine, cyano, azido, sulfhydryl, or alkylthio, heterocyclyl, aralkyl, or an aromatic or heteroaromatic moiety. In certain preferred embodiments, $R^{10}$ is $C_{6-10}$ aryl or 5- to 10-membered heteroaryl, and is optionally substituted with a substituent selected from alkyl, cycloalkyl, halogen (e.g., fluoro), hydroxyl, alkoxy, cycloalkyloxy, cycloalkylalkyl, cycloalkylalkoxy, amino, amidine, cyano, sulfhydryl, or alkylthio, heterocyclyl, aralkyl, or an aromatic or heteroaromatic moiety.

In certain embodiments, the substituents on $R^{12}$ are selected from hydroxy, $C_{1-6}$ alkyl, $C_{1-6}$ alkoxy, $C_{3-7}$ alkoxyalkoxy, $C_{1-6}$ haloalkyl, $C_{1-6}$ haloalkyloxy, $C_{3-7}$ haloalkoxyalkoxy, $C_{3-6}$ cycloalkyl, $C_{3-6}$ cycloalkyloxy, $C_{4-8}$ cycloalkylalkyloxy, $C_{4-8}$ cycloalkylalkyl, 4 to 7-membered heterocyclyl, 4 to 7-membered heterocyclyloxy, halo, cyano, oxo, or amino optionally substituted with up to 2 $C_{1-6}$ alkyl or $C_{3-6}$ cycloalkyl. In certain embodiments, the substituents on $R^{12}$ are selected from hydroxy, $C_{1-6}$ alkyl, $C_{1-6}$ alkoxy, $C_{1-6}$ haloalkyl, $C_{1-6}$ haloalkyloxy, $C_{3-6}$ cycloalkyl, $C_{3-6}$ cycloalkyloxy, $C_{4-8}$ cycloalkylalkyloxy, $C_{4-8}$cycloalkylalkyl, 4 to 7-membered heterocyclyl, halo, cyano, oxo, or amino optionally substituted with up to 2 $C_{1-6}$ alkyl or $C_{3-6}$ cycloalkyl. In certain embodiments, the substituents on $R^{12}$ are selected from $C_{1-6}$ alkyl, $C_{3-6}$ cycloalkyl, halo, cyano, or oxo. In certain embodiments, the substituents on $R^{12}$ are selected from $C_{1-6}$ alkoxy.

In certain preferred embodiments, $R^{10}$ is phenyl. In certain such embodiments, $R^{10}$ has at least one substituent at a meta- or ortho-position, preferably at a meta position. In certain such embodiments, the phenyl ring bears at least two substituents.

In certain preferred embodiments, $R^{10}$ is a 5- to 10-membered heteroaryl, such as pyridinyl, pyrimidinyl, pyrazinyl, pyrazolyl, imidazolyl, or thiazolyl.

In certain preferred embodiments. $R^{10}$ is a 5- to 10-membered heteroaryl, such as pyridinyl, pyrimidinyl, pyrazinyl, pyridazinyl, pyrazolyl, imidazolyl, or thiazolyl. In certain such embodiments, $R^{10}$ is pyridinyl, pyrimidinyl, or pyrazinyl.

In certain preferred embodiments, $R^{12}$ is phenyl, pyridinyl, pyrimidinyl, pyrazinyl, pyrazolyl, imidazolyl, or thiazolyl. In certain such embodiments, $R^{12}$ is pyridinyl, pyrimidinyl, or pyrazinyl.

In certain embodiments, at least one of $R^2$, $R^3$, $R^4$, $R^5$, $R^6$, $R^7$, $R^8$, and $R^9$ is $C_{1-6}$ alkyl, $C_{3-6}$ cycloalkyl, or halogen; $R^1$ is $C_{4-6}$ alkyl, $C_{3-6}$ cycloalkyl, or fluoro; $R^{10}$ is substituted or unsubstituted 5- to 10-membered heteroaryl or $C_{10}$ aryl; $R^{10}$ is phenyl substituted at the meta or ortho position with at least one substituent selected from halogen (e.g., fluoro or chloro), hydroxyl, alkoxy, phosphoryl, phosphate, phosphonate, phosphinate, amino, amidine, imine, cyano, azido, sulfhydryl, or alkylthio, heterocyclyl, aralkyl, aryl, or heteroaryl; $R^{10}$ is phenyl substituted with $C_{1-6}$ alkyl optionally substituted with $C_{1-6}$ alkyl, $C_{3-6}$ cycloalkyl, halogen, carbonyl, cyano, or hydroxyl; or $R^{10}$ is phenyl substituted with $R^{12}$ or X—$R^{12}$, preferably X—$R^{12}$.

In certain embodiments, Z is $CR^{17}$ or W is $CR^{18}$; at least one of $R^2$, $R^3$, $R^4$, $R^5$, $R^6$, $R^7$, $R^8$, and $R^9$ is $C_{1-6}$ alkyl, $C_{3-6}$ cycloalkyl, or halogen; $R^1$ is $C_{4-6}$ alkyl, $C_{3-6}$ cycloalkyl, $C_{4-8}$ cycloalkylalkyl, or fluoro; $R^{10}$ is substituted or unsubstituted 5- to 10-membered heteroaryl or $C_{10}$ aryl; $R^{10}$ is phenyl substituted at the meta or ortho position with at least one substituent selected from halogen (e.g., fluoro or chloro), hydroxyl, alkoxy, phosphoryl, phosphate, phosphonate, phosphinate, amino, amidine, imine, cyano, azido, sulfhydryl, or alkylthio, heterocyclyl, aralkyl, aryl, or heteroaryl; $R^{10}$ is phenyl substituted with $C_{1-6}$ alkyl optionally substituted with $C_{1-6}$ alkyl, $C_{3-6}$ cycloalkyl, halogen, carbonyl, cyano, or hydroxyl; $R^{10}$ is phenyl substituted with $R^{12}$ or X—$R^{12}$, preferably X—$R^{12}$; $R^{10}$ is phenyl substituted with fluoro; or $R^1$ is $C_{3-6}$ alkyl and $R^{10}$ is phenyl optionally substituted with halogen (e.g., fluoro or chloro), hydroxyl, alkoxy, phosphoryl, phosphate, phosphonate, phosphinate, amino, amidine, imine, azido, sulfhydryl, or alkylthio. In certain embodiments, $R^1$ is $C_{4-6}$ alkyl. $C_{3-6}$ cycloalkyl, or fluoro.

In certain embodiments. Z is $CR^{17}$ or W is $CR^{18}$.

In certain embodiments, Z is $CR^{17}$.

In certain embodiments, Z and W are N and $R^{10}$ is phenyl substituted at the meta or ortho position with at least one substituent selected from chloro, alkoxy, phosphoryl, phosphate, phosphonate, phosphinate, amino, amidine, imine, cyano, azido, sulfhydryl, or alkylthio, heterocyclyl, aralkyl, aryl, or heteroaryl.

In certain embodiments, Z and W are N, $R^1$ is H and $R^{10}$ is phenyl substituted with at least one substituent selected from halogen (e.g., fluoro or chloro), alkyl, trifluoromethyl, cycloalkyl, alkoxy, trifluoromethoxy, or cyano.

In certain embodiments, at least one of $R^2$, $R^3$, $R^4$, $R^5$, $R^6$, $R^7$, $R^8$, and $R^9$ is $C_{1-6}$ alkyl, $C_{3-6}$ cycloalkyl, or halogen.

In certain embodiments, $R^1$ is $C_{4-6}$ alkyl, $C_{3-6}$ cycloalkyl, or fluoro.

In certain embodiments. $R^1$ is $C_{4-6}$ alkyl. $C_{3-6}$ cycloalkyl, $C_{4-8}$ cycloalkylalkyl, or fluoro.

In certain embodiments, $R^1$ is $C_{3-6}$ alkyl and $R^{10}$ is phenyl optionally substituted with halogen (e.g., fluoro or chloro), hydroxyl, alkoxy, phosphoryl, phosphate, phosphonate, phosphinate, amino, amidine, imine, azido, sulfhydryl, or alkylthio.

In certain embodiments. $R^1$ is methyl and $R^{10}$ is phenyl substituted in the meta or ortho position with halogen (e.g., fluoro or chloro), alkyl, trifluoromethyl, alkoxy, trifluoromethoxy or cycloalkyl.

In certain embodiments, $R^1$ is ethyl and $R^{10}$ is phenyl optionally substituted with halogen (e.g., fluoro or chloro), hydroxyl, alkoxy, trifluoromethoxy, amino, alkyl, trifluoromethyl or cycloalkyl.

In certain embodiments, $R^1$ is propyl and $R^{10}$ is unsubstituted phenyl or phenyl optionally substituted with halogen (e.g., fluoro or chloro), hydroxyl, alkoxy, trifluoromethoxy, amino, alkyl, trifluoromethyl or cycloalkyl.

In certain embodiments, $R^{10}$ is substituted or unsubstituted 5- to 10-membered heteroaryl or $C_{10}$ aryl.

In certain embodiments, $R^{10}$ is phenyl substituted with $R^{12}$ or X—$R^{12}$, preferably X—$R^{12}$.

In certain embodiments, $R^{10}$ is phenyl substituted at the meta or ortho position with at least one substituent selected from halogen (e.g., fluoro or chloro), hydroxyl, alkoxy, phosphoryl, phosphate, phosphonate, phosphinate, amino, amidine, imine, cyano, azido, sulfhydryl, or alkylthio, heterocyclyl, aralkyl, aryl, or heteroaryl.

In certain embodiments, $R^{10}$ is phenyl substituted with $C_{1-6}$ alkyl optionally substituted with $C_{1-6}$ alkyl, $C_{3-6}$ cycloalkyl, halogen, carbonyl, cyano, or hydroxyl.

In certain embodiments, $R^{10}$ is phenyl substituted with fluoro. In certain embodiments, $R^{10}$ is fluorophenyl, and is not further substituted.

In certain embodiments, $R^{10}$ is phenyl substituted with fluoro.

In certain embodiments, if $R^1$ is H, methyl, ethyl, or chloro and $R^2$, $R^3$, $R^4$, $R^5$, $R^6$, $R^7$, $R^8$, and $R^9$ are H, then $R^{10}$ is not unsubstituted phenyl. In certain embodiments, if $R^1$ is methyl and $R^2$, $R^3$, $R^4$, $R^5$, $R^6$, $R^7$, $R^8$, and $R^9$ are H, then $R^{10}$ is not 4-chlorophenyl, 4-trifluoromethylphenyl, or 4-cyanophenyl. In certain embodiments, if $R^1$ is ethyl or n-propyl and $R^2$, $R^3$, $R^4$, $R^5$, $R^6$, $R^7$, $R^8$, and $R^9$ are H, then $R^{10}$ is not 4-cyanophenyl. In certain embodiments, compounds of the present invention do not include compounds represented by the following structures:

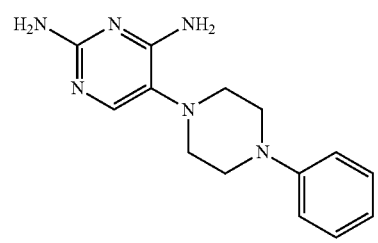

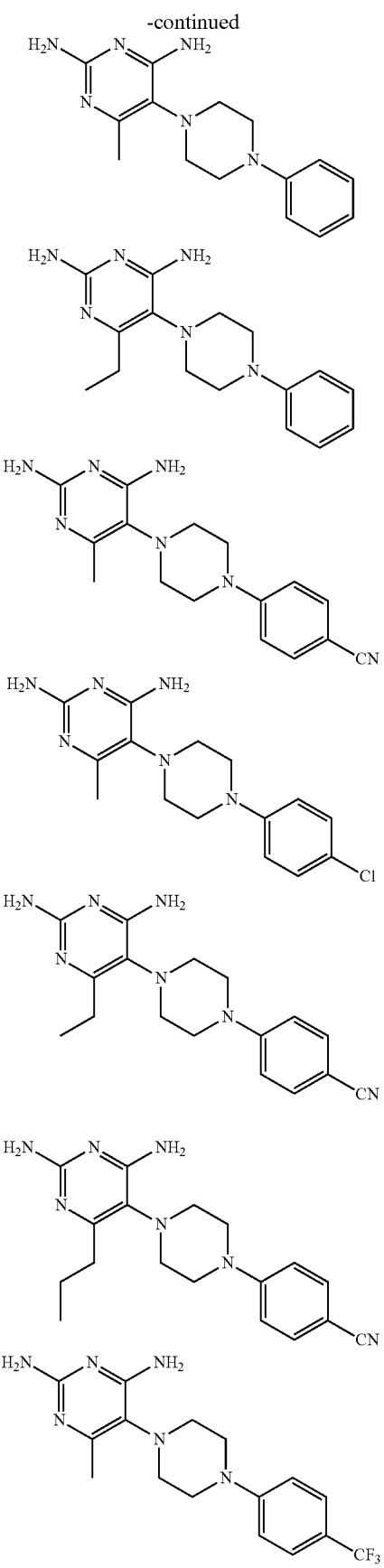

In certain embodiments, $R^1$ is H, $C_{1-3}$ alkyl, $C_{3-5}$ cycloalkyl, $C_{4-8}$ cycloalkylalkyl, or halogen. In certain embodiments, $R^1$ is $C_{4-8}$ cycloalkylalkyl.

In certain embodiments, $R^1$ is H, $C_{1-3}$ alkyl, $C_{3-5}$ cycloalkyl, or halogen.

In certain embodiments, the substituents on each instance of $R^{11}$ are selected from $C_{1-6}$ alkyl, $C_{3-6}$ cycloalkyl, halo, cyano, or oxo. In further embodiments, the substituents on each instance of $R^{11}$ are limited to methyl, ethyl, cyclopropyl, halo, cyano, or oxo.

In certain embodiments, $R^1$ is H, and $R^{10}$ is phenyl.

In certain embodiments, $R^{10}$ is substituted with $R^{12}$ and $R^{10}$ is optionally further substituted; and $R^{12}$ is selected from substituted or unsubstituted phenyl, 5- or 6-membered heteroaryl, or 4 to 7-membered heterocyclyl. In certain such embodiments, $R^{10}$ is substituted with $R^{12}$, and $R^{10}$ is optionally further substituted with one or more substituents independently selected from $R^{11}$; and $R^{12}$ is substituted or unsubstituted phenyl, 5- or 6-membered heteroaryl, or 4 to 7-membered heterocyclyl. In certain preferred embodiments, $R^{12}$ is phenyl, pyridinyl, pyrimidinyl, pyrazinyl, pyrazolyl, imidazolyl, thiazolyl, or tetrahydropyranyl. In certain such embodiments, $R^{12}$ is phenyl, pyridinyl, pyrimidinyl, pyrazinyl, or tetrahydropyranyl. In certain embodiments, $R^{12}$ is phenyl, pyridinyl, pyrimidinyl, pyrazinyl, pyrazolyl, imidazolyl, or thiazolyl. In certain embodiments, each instance of $R^{11}$ is independently selected from $C_{1-6}$ alkyl, $C_{1-6}$ alkoxy, $C_{2-6}$ alkoxyalkyl, cyano, or halogen. In certain preferred embodiments, the substituents on $R^{12}$ are selected from hydroxy, $C_{1-6}$ alkyl, $C_{1-6}$ alkoxy, $C_{1-6}$ haloalkyl, $C_{1-6}$ haloalkyloxy, $C_{3-6}$ cycloalkyl, $C_{3-6}$ cycloalkyloxy, $C_{4-8}$ cycloalkylalkyl, 4 to 7-membered heterocyclyl, halo, cyano, oxo, or amino optionally substituted with up to 2 $C_{1-6}$ alkyl or $C_{3-6}$ cycloalkyl. In certain preferred embodiments, the substituents on $R^{12}$ are selected from $C_{1-6}$ alkyl, $C_{3-6}$ cycloalkyl, halo, cyano, or oxo. In further embodiments, the substituents on $R^{12}$ are limited to methoxy, ethoxy, hydroxy, methyl, ethyl, cyclopropyl, cyclobutylamine, dimethylamine, methylamine, trifluoromethyl, halo, cyano, or oxo. In further embodiments, the substituents on $R^{12}$ are limited to methyl, ethyl, cyclopropyl, halo, cyano, or oxo.

In certain embodiments, $R^{12}$ is substituted or unsubstituted phenyl, 5- or 6-membered heteroaryl, or 4- to 7-membered heterocyclyl. In certain such embodiments, $R^{12}$ is substituted with methyl, ethyl, methoxy, ethoxy or trifluoromethyl. In certain preferred embodiments, $R^1$ is H. In certain embodiments. $R^{12}$ is phenyl, pyrimidin-5-yl, or pyridin-3-yl. In certain embodiments, $R^{12}$ is pyrimidin-5-yl or pyridin-3-yl. In certain preferred embodiments, $R^{12}$ is 2-methoxy-pyrimidin-5-yl, 3-methoxyphenyl, 2-methoxy-pyridin-3-yl, 2-methyl-pyrimidin-5-yl, or tetrahydropyran-4-yl. In certain preferred embodiments, $R^{12}$ is 2-methoxy-pyrimidin-5-yl, 3-methoxyphenyl, 2-methoxy-pyridin-3-yl, or 2-methyl-pyrimidin-5-yl.

In certain preferred embodiments, the present invention relates to a compound having one of the following structures:

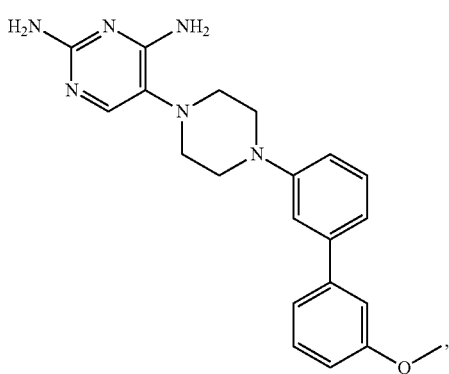

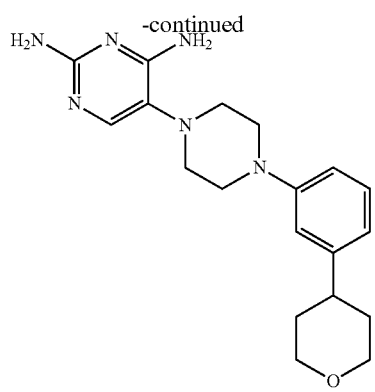

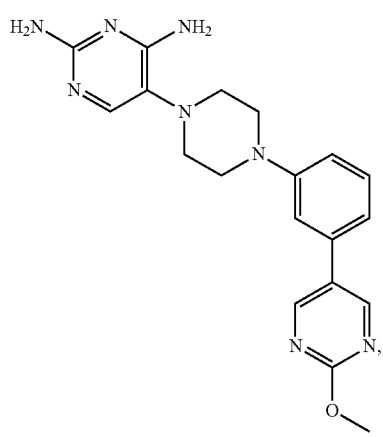

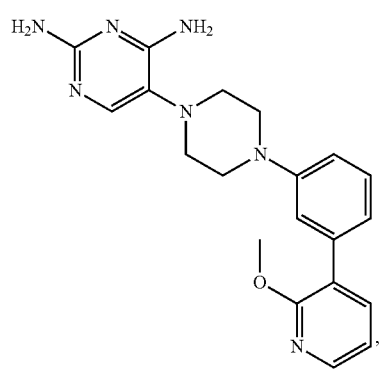

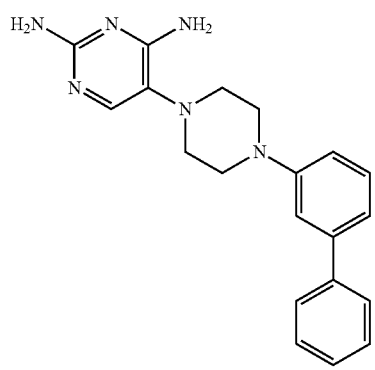 [SMILES: Nc1ncc(N2CCN(c3cccc(-c4ccccc4)c3)CC2)c(N)n1]

or a pharmaceutically acceptable salt or prodrug thereof.

In certain embodiments, $R^{12}$ is substituted or unsubstituted phenyl. In further embodiments, the substituents on $R^{12}$ are selected from $C_{1-6}$ alkyl, $C_{1-6}$ alkyloxy, $C_{3-6}$ cycloalkyl, halo, cyano, or oxo. In further embodiments, the substituents on $R^{12}$ are selected from $C_{1-6}$ alkyl, $C_{3-6}$ cycloalkyl, halo, cyano, or oxo. In certain preferred embodiments, the substituents on $R^{12}$ are limited to hydroxyl, methyl, trifluoromethyl, trifluoromethoxy, ethyl, cyclopropyl, methoxy, ethoxy, halo, cyano, or oxo. In certain preferred embodiments, the substituents on $R^{12}$ are limited to methyl, ethyl, cyclopropyl, halo, cyano, or oxo.

In certain preferred embodiments, the present invention relates to a compound having the following structure:

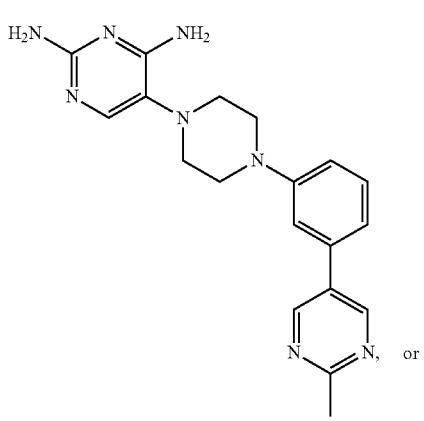

or a pharmaceutically acceptable salt or prodrug thereof.

In certain embodiments, $R^1$ is $C_{1-6}$ alkyl, $C_{3-6}$ cycloalkyl, or $C_{4-8}$ cycloalkylalkyl; and $R^{10}$ is optionally substituted with one or more substituents independently selected from $R^{11}$. In certain preferred embodiments, each instance of $R^{11}$ is independently selected from $C_{1-6}$ alkyl, $C_{1-6}$ alkoxy, $C_{2-6}$ alkoxyalkyl, cyano, or halo. In certain preferred embodiments. $R^1$ is $C_{3-6}$ cycloalkyl, $C_{4-8}$ cycloalkylalkyl, or $C_{1-3}$ alkyl.

In certain embodiments, $R^1$ is $C_{1-6}$ alkyl or $C_{3-6}$ cycloalkyl; and $R^{10}$ is optionally substituted with one or more substituents independently selected from $R^{11}$. In certain preferred embodiments, each instance of $R^{11}$ is independently selected from $C_{1-6}$ alkyl, $C_{1-6}$ alkoxy, $C_{2-6}$ alkoxyalkyl, cyano, or halo. In certain preferred embodiments, $R^1$ is $C_{3-6}$ cycloalkyl or $C_{1-3}$ alkyl.

In certain preferred embodiments, the present invention relates to a compound having one of the following structures:

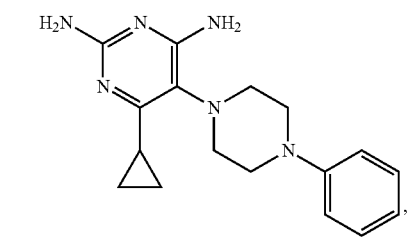

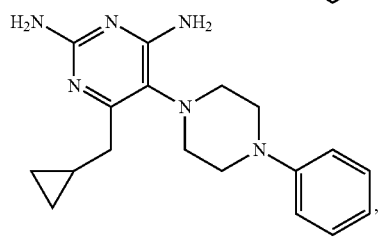

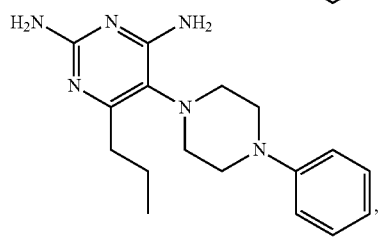

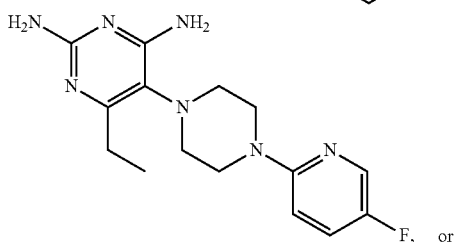

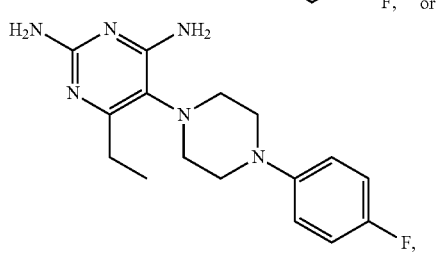

or a pharmaceutically acceptable salt or prodrug thereof.

In certain embodiments of the above, Z is CR$^{17}$ and W is N. In certain such embodiments. R$^1$ is C$_{1-6}$ alkyl or C$_{3-6}$ cycloalkyl; and R$^{10}$ is optionally substituted with one or more substituents independently selected from R$^{11}$. In certain preferred embodiments, each instance of R$^{11}$ is independently selected from C$_{1-6}$ alkyl, C$_{1-6}$ alkoxy, C$_{2-6}$ alkoxyalkyl, cyano, or halo.

In certain embodiments of the above, Z is CR$^{17}$. In certain embodiments, Z is CR$^{17}$; R$^1$ is C$_{1-6}$ alkyl, C$_{3-6}$ cycloalkyl, C$_{4-8}$ cycloalkylalkyl; and R$^{10}$ is optionally substituted with one or more substituents independently selected from R$^{11}$. In certain preferred embodiments, each instance of R$^{11}$ is independently selected from C$_{1-6}$ alkyl, C$_{1-6}$ alkoxy, C$_{2-6}$ alkoxyalkyl, cyano, or halo.

In certain preferred embodiments, the present invention relates to a compound having one of the following structures:

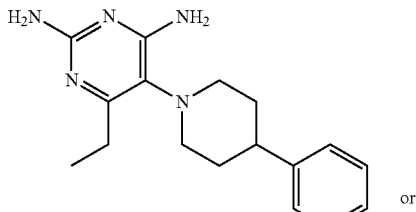

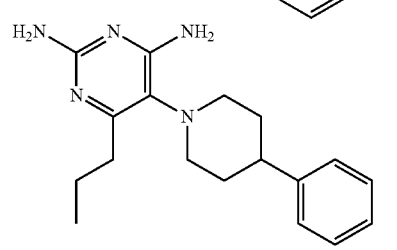

or a pharmaceutically acceptable salt or prodrug thereof.

In certain embodiments, R$^{10}$ is substituted with R$^{15}$ and R$^{16}$ and is optionally substituted with one or more substituents independently selected from R$^{11}$; and R$^{15}$ and R$^{16}$ are independently selected from halo, such as chloro. In certain preferred embodiments, each instance of R$^{11}$ is independently selected from C$_{1-6}$ alkyl, C$_{1-6}$ alkoxy, C$_{2-6}$ alkoxyalkyl, cyano, or halo.

In certain preferred embodiments, the present invention relates to a compound having the following structure:

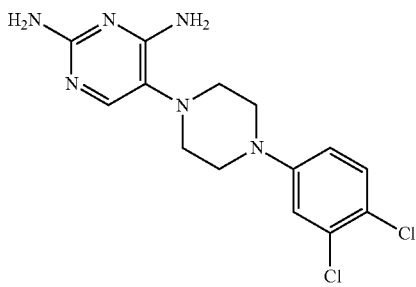 [SMILES: Nc1ncc(N2CCN(c3ccc(Cl)c(Cl)c3)CC2)c(N)n1]

or a pharmaceutically acceptable salt or prodrug thereof.

In certain embodiments, R$^{10}$ is substituted with R$^{15}$ and is optionally substituted with one or more substituents independently selected from R$^{11}$; and R$^{15}$ is independently selected from halo (such as chloro) or haloalkyl (such as trifluoromethyl). In certain preferred embodiments, each instance of R$^{11}$ is independently selected from C$_{1-6}$ alkyl, C$_{1-6}$ alkoxy, C$_{2-6}$ alkoxyalkyl, cyano, or halo.

In certain preferred embodiments, the present invention relates to a compound having the following structure:

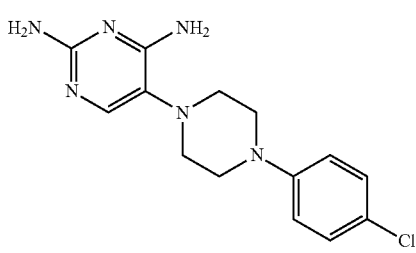

-continued

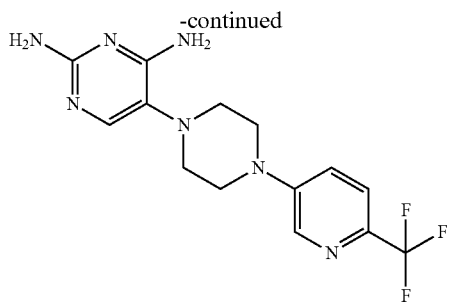

or a pharmaceutically acceptable salt or prodrug thereof.

In another aspect, the present invention relates to a pharmaceutical composition comprising a compound as disclosed herein.

In yet another aspect, the present invention relates to a method of preventing or inhibiting the growth or proliferation of a microorganism using a compound of formula (I). In certain embodiments, the microorganism is a protozoan. In certain embodiments, the protozoan is of genus *Toxoplasma, Leishmania, Trypanosoma,* or *Plasmodium.* In certain embodiments, the microorganism is *T. gondii, T. cruzi, T. brucei,* or is of genus *Leishmania* or *Plasmodium.* In certain preferred embodiments, the microorganism is *T. gondii, T. cruzi, P. falciparum, T. brucei,* or *L. major.* In certain embodiments inhibiting the growth or proliferation of a microorganism comprises applying a compound having the structure of formula (I) to a location. The compound may be applied in the form of a spray (e.g., from a spray bottle) or by wiping (e.g., with a pre-soaked wipe, a mop, or a sponge). In certain embodiments, the location is one where the microorganism is known or suspected to be present. In certain embodiments, the location is one that is at risk for the presence of the microorganism. In certain embodiments, the compound of formula (I) is applied prophylactically. In certain embodiments, the compound of formula (I) is applied after suspected contamination by the protozoan. In certain embodiments, the location may be a surface, such as a cooking surface or a surface that has contact with material suspected of containing the microorganism, such as a surface that has had contact with raw meat or animal (such as cat) feces. In certain embodiments, the cooking surface is a cutting board, a counter, or a utensil, such as a knife or fork. In certain embodiments, the location may be the surface or interior of a food, such as a meat or a vegetable. In certain embodiments, the location may be a liquid, such as water, for instance drinking water. In certain embodiments, the location may be soil. In certain embodiments, the location may be a place where a cat has defecated or will defecate, or an area where cat feces or cat litter is likely to spread or to have been spread. In further embodiments, the location is a litterbox or the area around a litterbox. In certain embodiments, the location is a body surface, such as a hand.

In certain embodiments, the compound of formula (I) is used to prevent transmission of the microorganism between people and/or animals. In further embodiments, the transmission is congenital transmission. In further embodiments, the compound of formula (I) is administered to a mother, administered to an infant, applied to the skin of the mother, or applied to the skin of the infant. In certain embodiments, the compound of formula (I) is applied to blood, such as blood intended for transfusion. In certain embodiments, the compound of formula (I) is applied to an organ, such as an organ intended for transplant. In certain embodiments, the compound of formula (I) is administered to an organ donor prior to transplant. In certain embodiments, the compound of formula (I) is administered to an animal, such as a cat or a mouse.

In yet another aspect, the present invention relates to a method of treating an infection, comprising administering a compound having the structure of formula (I), a pharmaceutically acceptable salt or prodrug thereof, or a pharmaceutical composition comprising such a compound, salt, or prodrug. In certain embodiments, the infection is caused by a protozoan. In certain embodiments, the protozoan is of genus *Toxoplasma, Leishmania, Trypanosoma,* or *Plasmodium.* In certain embodiments, the microorganism is *T. gondii, T. cruzi, T. brucei,* or is of genus *Leishmania* or *Plasmodium.* In certain preferred embodiments, the infection is caused by *T. gondii, T. cruzi, P. falciparum, T. brucei,* or *L. major.*

In yet another aspect, the present invention relates to one of the compounds or compositions disclosed herein, a pharmaceutically acceptable salt or prodrug thereof, or a pharmaceutical composition comprising such a compound, salt, or prodrug, for use in the treatment of an infection. In certain embodiments, the infection is caused by a protozoan, such as an Apicomplexan protozoan. In certain embodiments, the protozoan is of genus *Toxoplasma, Leishmania, Trypanosoma,* or *Plasmodium.* In certain embodiments, the microorganism is *T. gondii, T. cruzi, T. brucei,* or is of genus *Leishmania* or *Plasmodium.* In certain preferred embodiments, the infection is caused by *T. gondii, T. cruzi, P. falciparum, T. brucei,* or *L. major.*

In still another aspect, the present invention relates to a compound having the structure of formula (I), a pharmaceutically acceptable salt or prodrug thereof, or a pharmaceutical composition comprising such a compound, salt, or prodrug for use in the treatment of an infection.

The compounds disclosed herein inhibit DHFR, and can prevent or ameliorate infections, including toxoplasmosis. In certain embodiments, the compounds herein preferentially inhibit protozoan DHFR relative to human DHFR. In certain such embodiments, the protozoan is of genus *Toxoplasma, Leishmania, Trypanosoma,* or *Plasmodium.* In certain embodiments, the microorganism is *T. gondii. T. cruzi, T. brucei,* or is of genus *Leishmania* or *Plasmodium.* In certain preferred embodiments, the microorganism is *T. gondii, T. cruzi, P. falciparum, T. brucei,* or *L. major.* In certain such embodiments, the selectivity of the compounds herein for protozoan DHFR (such as *T. gondii, T. cruzi, P. falciparum, T. brucei,* or *L. major*) versus human DHFR (as determined by the ratio of the compound's $IC_{50}$ against each enzyme) is greater than 3-fold, greater than 10-fold, greater than 30-fold, greater than 50-fold, greater than 75-fold, greater than 100-fold, or greater than 300-fold. In certain embodiments, the compounds herein have an $IC_{50}$ for protozoan DHFR (such as *T. gondii, T. cruzi, P. falciparum, T. brucei,* or *L. major*) less than 1000 nM or less than 100 nM, preferably less than 10 nM. In certain embodiments, the selectivity of the compounds herein for *T. gondii, T. cruzi, P. falciparum, T. brucei,* or *L. major* versus human DHFR (as determined by the ratio of the compound's $IC_{50}$ against each receptor) is greater than 3-fold, greater than 10-fold, greater than 30-fold, greater than 50-fold, greater than 75-fold, greater than 100-fold, or greater than 300-fold. In certain embodiments, the compounds herein have an $IC_{50}$ for *T. gondii, T. cruzi, P. falciparum, T. brucei,* or *L. major* DHFR of less than 1000 nM or less than 100 nM, preferably less than 10 nM.

In certain embodiments, compounds of the invention may be prodrugs of the compounds disclosed herein, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl, or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomers. For example, a compound of the invention may have greater than 30% de, 40% de, 50% de, 60% de, 70% de, 80% de, 90% de, or even 95% or greater de.

In certain embodiments, the present invention relates to methods of treatment with a compound disclosed herein, or a pharmaceutically acceptable salt thereof. In certain embodiments, the therapeutic preparation may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound. A diastereomerically enriched mixture may comprise, for example, at least 60 mol percent of one diastereomer, or more preferably at least 75, 90, 95, or even 99 mol percent.

In certain embodiments, the present invention relates to methods of treatment with a compound disclosed herein, or a pharmaceutically acceptable salt thereof. In certain embodiments, the therapeutic preparation may be enriched to provide predominantly one enantiomer of such a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound disclosed herein. A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient, comprising any of the compounds shown above (e.g., a compound of the invention), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkvynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alknyl groups by one or more alkyl, carbocyclyl, aryl, heterocyclyl, or heteroaryl groups is contemplated.

The term "amide", as used herein, refers to a group

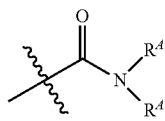

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

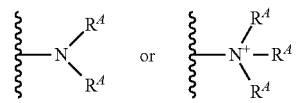

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

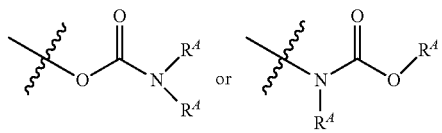

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^A$, wherein R$^A$ represents a hydrocarbyl group.

The term "carboxy", as used herein, refers to a group represented by the formula —CO$_2$H.

The term "ester", as used herein, refers to a group —C(O)OR$^A$ wherein R$^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO₃H, or a pharmaceutically acceptable salt thereof.

The term "sulfonamide" is art-recognized and refers to the group represented by the general formulae

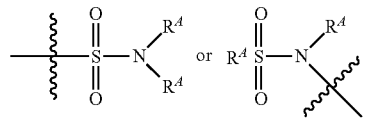

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —S(O)—$R^A$, wherein $R^A$ represents a hydrocarbyl.

The term "sulfonate" is art-recognized and refers to the group SO₃H, or a pharmaceutically acceptable salt thereof.

The term "sulfone" is art-recognized and refers to the group —S(O)₂—$R^A$, wherein $R^A$ represents a hydrocarbyl.

The term "thioalkyl", as used herein, refers to an alkyl group substituted with a thiol group.

The term "thioester", as used herein, refers to a group —C(O)S$R^A$ or —SC(O)$R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

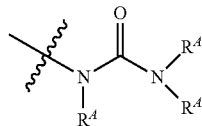

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996. John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxvcarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions, are converted into the therapeutically active agents of the present invention. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of the invention in a formulation represented above can be replaced with the corresponding suitable prodrug, e.g., wherein a hydroxyl in the parent compound is presented as an ester or a carbonate or carboxylic acid present in the parent compound is presented as an ester.

Use of DHFR Inhibitors

Another embodiment of the invention is the use of the compounds described herein for the treatment of infections (e.g., parasitic infections, such as toxoplasmosis). In certain embodiments, the compounds described herein may be used conjointly with other compounds useful for that purpose, such as sulfadiazene, sulfamethoxazole, clindamycin, spiramycin, atovaquone, CDPK1 inhibitors, or cytochrome $BC_1$ inhibitors. Compounds of the present invention may also be used conjointly with leucovorin to improve tolerability.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch, (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol, (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution, (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol, (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, L-ascorbic acid, L-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, D-glucoheptonic acid, D-gluconic acid, D-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, L-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, L-pyroglutamic acid, salicylic acid, sebacic acid, stearic acid, succinic acid, sulfuric acid, L-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the invention relates to a method for conducting a pharmaceutical business, by manufacturing a formulation of a compound of the invention, or a kit as described herein, and marketing to healthcare providers the benefits of using the formulation or kit for treating or preventing any of the diseases or conditions as described herein.

EXAMPLES

Example 1: General Methods

NMR spectra were recorded on a Varian 400 MHz for $^1$H NMR. LCMS were taken on a quadrupole Mass Spectrometer on Shimadzu LCMS 2010 (Column: sepax ODS 50×2.0 mm, 5 um) or Agilent 1200 HPLC, 1956 MSD (Column: Shim-pack XR-ODS 30×3.0 mm, 2.2 um) operating in ES (+) ionization mode.

LC/MS Method A:

Run on a Shimadzu LC-20AB with a MS 2010 detector using a Luna-C18(1) column (2.0*30 mm, 3 um) at 40° C. Mobile phase A was 0.037% (v/v) aqueous TFA and mobile phase B was 0.018% (v/v) TFA in acetonitrile. The flow rate was 0.8 mL/min from 0.01 to 1.51 min, then 1.2 mL/min from 1.52 to 2.00 min. The gradient ran from 90% mobile phase A to 10% mobile phase A over 1.15 min then remained at 10% mobile phase A through 1.65 min then back to 90% mobile phase A at 1.66 min and was maintained at 90% mobile phase A through 2.0 min. The UV detection was 220 nm and the MS was measured in positive ion mode.

LC/MS Method B:

Run on an Agilent 1200 with a MS 6120 detector using an Xbridge Shield RP18 column (2.1*50 mm, 5 um) at 40° C. Mobile phase A was 10 mM aqueous $NH_4HCO_3$ and mobile phase B was acetonitrile. The flow rate was 1.0 mL/min from 0.01 to 2.48 min, then 1.2 mL/min from 2.50 to 3.00 min. The gradient ran from 90% mobile phase A to 20% mobile phase A over 2.00 min then remained at 20% mobile phase A through 2.48 min then back to 90% mobile phase A at 2.50 min and maintained at 90% mobile phase A through 3.0 min. The UV detection was 220 nm and the MS was measured in positive ion mode.

LC/MS Method C:

Run on an Agilent 1200 with a MS 6120 detector using an Xbridge Shield RP18 column (2.1*50 mm, 5 um) at 40° C. Mobile phase A was 10 mM aqueous $NH_4HCO_3$ and mobile phase B was acetonitrile. The flow rate was 1.0 mL/min from 0.01 to 2.50 min, then 1.2 mL/min from 2.51 to 3.00 min. The gradient ran from 70% mobile phase A to 10% mobile phase A over 1.50 min then remained at 10% mobile phase A through 2.50 min then back to 70% mobile phase A at 2.51 min and maintained at 70% mobile phase A through 3.0 min. The UV detection was 220 nm and the MS was measured in positive ion mode.

LC/MS Method D:

Run on an Agilent 1200 with a MS 6120 detector using a Venusil XBP-C18 column (2.1*50 mm, 5 um) at 40° C. Mobile phase A was 0.0375% aqueous TFA and mobile phase B was 0.018% TFA in acetonitrile. The flow rate was 0.8 mL/min from 0.01 to 4.5 min. The gradient was maintained at 99% mobile phase A from 0.00 min to 0.40 min, then the gradient ran from 99% mobile phase A to 10% mobile phase A over 3.00 min then to 0% mobile phase A over 0.45 min; then back to 99% mobile phase A over 0.01 min and maintained here for 0.55 min The UV detection was 220 nm and the MS was measured in positive ion mode.

Example 2: Synthetic Method A

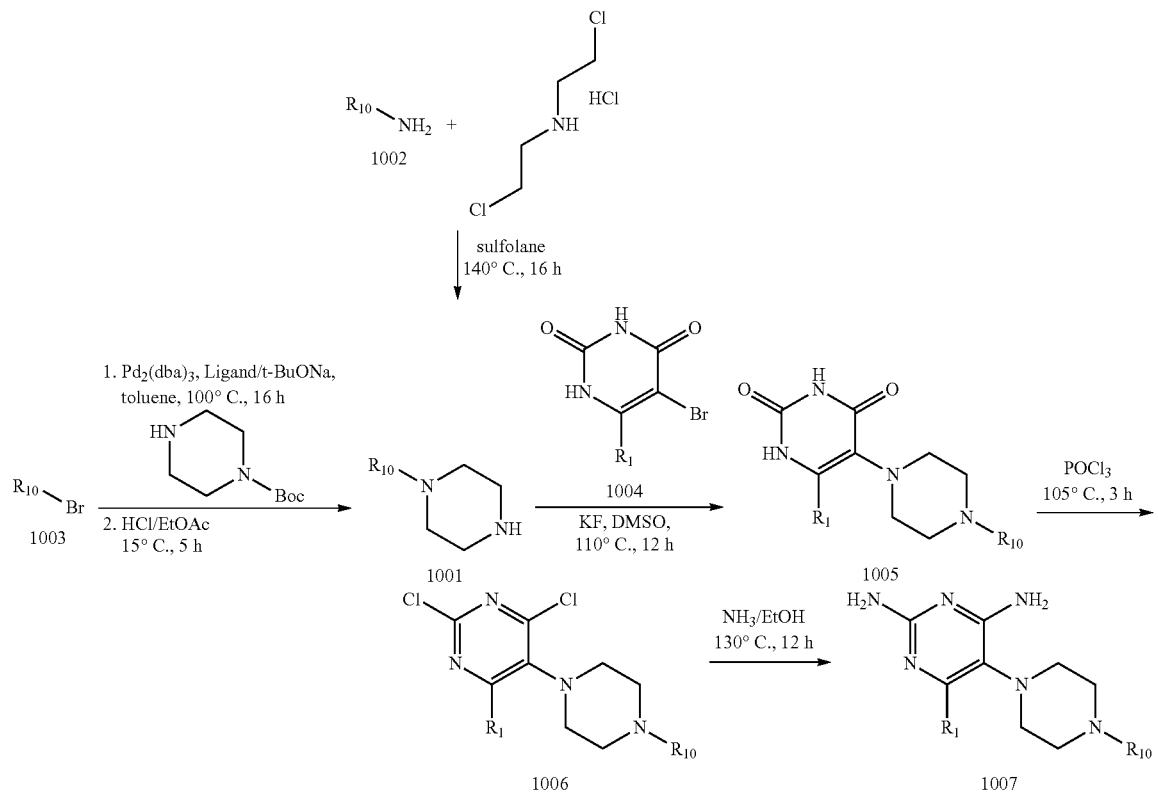

Piperazine intermediates 1001 are generally commercially available or can be prepared by various literature methods (i.e., Rong Gao and Daniel J. Canney. A versatile and practical microwave-assisted synthesis of sterically hindered N-arylpiperazines, J. Org. Chem., 2010, 75(21), 7451-53). For example, anilines or aminoheteroaryl starting materials 1002 can be reacted with bis(2-chloroethyl)amine with sulfolane at 140° C. to give intermediate 1001. (Lokesh Ravilla et. al., An efficient scale up process for synthesis of N-arylpiperazines Tetrahefron Letters, 2015, 56(30), 4541-44). Alternatively, protected piperazines can be reacted with a bromoaryl or bromoheteroaryl compounds 1003 under Buchwald conditions to give desired intermediates 1001.

Nucleophilic substitution reaction of 1001 with 5-bromopyrimidine-2,4(1H,3H)-diones 1004 using KF as basic catalyst and heating in DMSO gives 5-piperazinylpyrimidines 1005. Reaction with $POCl_3$ at 105° C. gives 2,4-dichloropyrimidines 1006 and desired 2,4-diaminopyrimidines 1007 are generated by reaction with $NH_3$ in ethanol at 130° C. 5-Bromopyrimidine-2,4(1H,3H)-diones 1004 are generally commercially available or can be prepared by bromination of the corresponding 6-substituted pyrimidinedione.

Alternatively, compounds of the invention can be prepared by Suzuki or Stille coupling reactions as shown below.

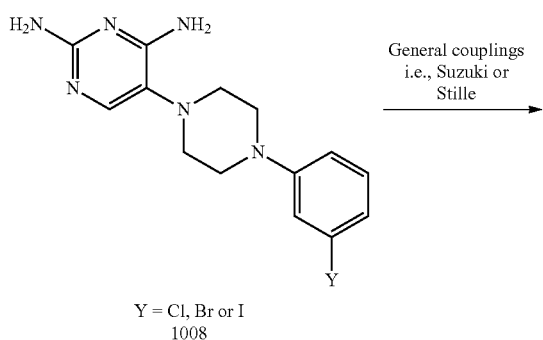

Y = Cl, Br or I
1008 final targets
1009

Synthetic Method A is exemplified below in the synthesis of 5-(4-([1,1'-biphenyl]-3-yl)piperazin-1-yl)pyrimidine-2,4-diamine (Compound 2).

Step 1. Tert-Butyl 4-([1,1'-biphenyl]-3-yl)piperazine-1-carboxylate

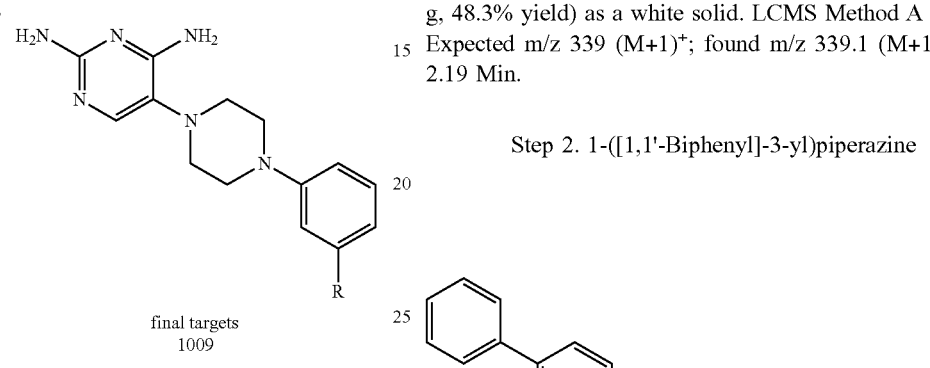

3-Bromo-1,1'-biphenyl (10.0 g, 42.9 mmol, 7.1 mL, 1.0 eq) was added to a solution of sodium 2-methylpropan-2-olate (4.9 g, 51.4 mmol, 1.2 eq) and Pd$_2$(dba)$_3$ (785.6 mg, 858.0 umol, 0.02 eq) in toluene (100.0 mL). 1,1'-Biphenyl]-2-yldicyclohexylphosphine (2.4 g, 6.8 mmol, 0.16 eq) and tert-butyl piperazine-1-carboxylate (7.9 g, 42.9 mmol, 1.0 eq) were added to the above mixture at 25° C., the reaction vessel was degassed with N$_2$ three times and the solution was stirred for 16 h at 100° C. under N$_2$ atmosphere. TLC (Petroleum ether:Ethyl acetate=5:1. Rf=0.51) showed 3-bromo-1,1'-biphenyl was consumed, and one major new spot with increased polarity was detected. The reaction mixture was concentrated under reduced pressure to give a brown residue which was purified by column chromatography (Petroleum ether:Ethyl acetate=10:1~5:1) to give tert-butyl 4-([1,1'-biphenyl]-3-yl)piperazine-1-carboxylate (7.0 g, 48.3% yield) as a white solid. LCMS Method A (ESI+): Expected m/z 339 (M+1)$^+$; found m/z 339.1 (M+1)$^+$, RT: 2.19 Min.

Step 2. 1-([1,1'-Biphenyl]-3-yl)piperazine

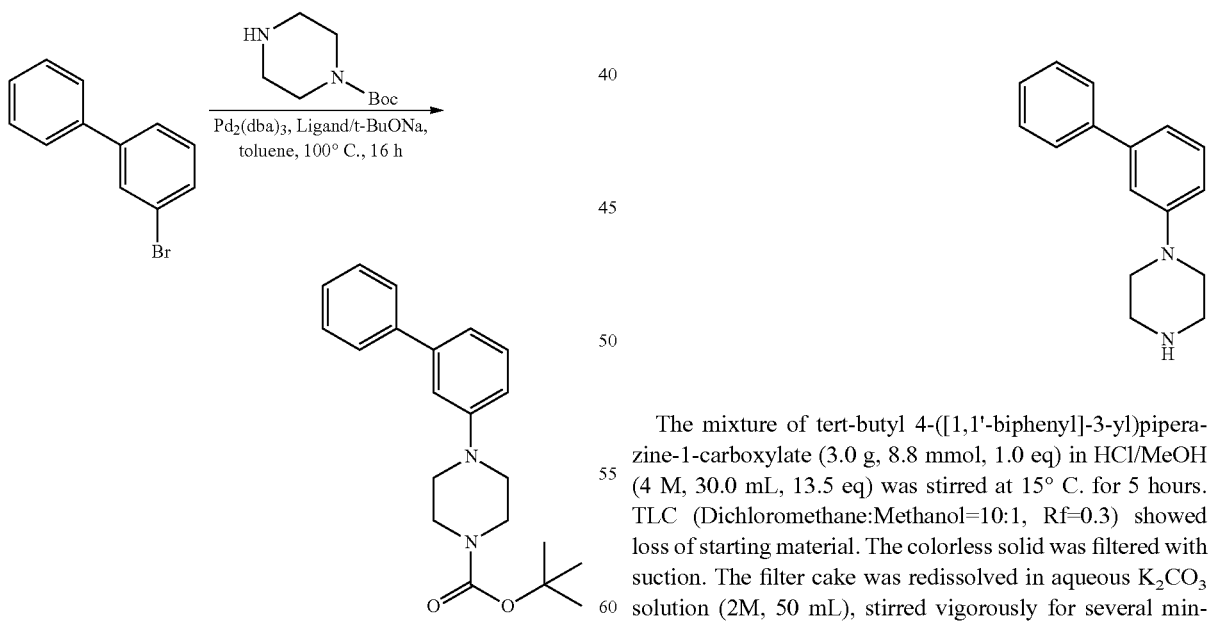

The mixture of tert-butyl 4-([1,1'-biphenyl]-3-yl)piperazine-1-carboxylate (3.0 g, 8.8 mmol, 1.0 eq) in HCl/MeOH (4 M, 30.0 mL, 13.5 eq) was stirred at 15° C. for 5 hours. TLC (Dichloromethane:Methanol=10:1, Rf=0.3) showed loss of starting material. The colorless solid was filtered with suction. The filter cake was redissolved in aqueous K$_2$CO$_3$ solution (2M, 50 mL), stirred vigorously for several minutes, and extracted with ethyl acetate (2×150 mL). The combined organic layers were dried over anhydrous Na$_2$SO$_4$ and filtered and concentrated under reduced pressure to give 1-([1,1'-Biphenyl]-3-yl)piperazine (2.0 g, 8.3 mmol, 94.7% yield) as a yellow oil. LCMS Method B (ESI+): Expected m/z 239 (M+1)$^+$; Found m/z 239.1 (M+1)$^+$, RT: 2.19 Min.

Step 3. 5-(4-([1,1-biphenyl]-3-yl)piperazin-1-yl)pyrimidine-2,4(1H,3H)-dione

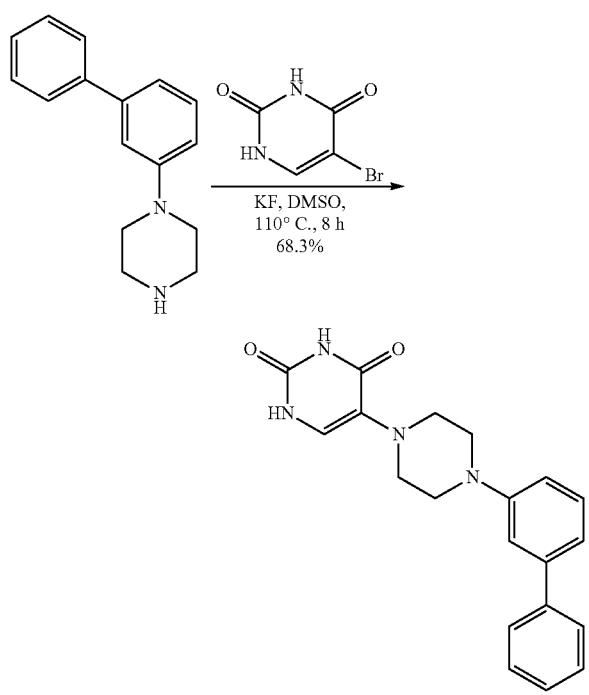

To a mixture of 5-bromo-1H-pyrimidine-2,4-dione (400.6 mg, 2.1 mmol, 1.0 eq) and 1-([1,1'-biphenyl]-3-yl)piperazine (500 mg, 2.1 mmol, 1.0 eq) in DMSO (10.00 mL) was added potassium fluoride (182.8 mg, 3.15 mmol, 1.5 eq). The resulting mixture was stirred at 110° C. for 8 hours, cooled to room temperature, poured into water and the gray precipitate collected by suction filtration. The gray solid was washed with 100 mL of 1:1 EtOAc:petroleum ether to give 5-(4-([1,1'-biphenyl]-3-yl)piperazin-1-yl)pyrimidine-2,4(1H,3H)-dione (500.0 mg, 1.4 mmol, 68.3% yield) as a gray solid. LCMS Method B (ESI+): Expected m/z 349.1 (M+1)$^+$; found m/z 349.1 (M+1)$^+$, RT: 2.16 Min.

Step 4. 5-(4-([1,1'-biphenyl]-3-yl)piperazin-1-yl)-2,4-dichloropyrimidine

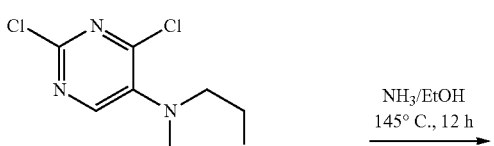

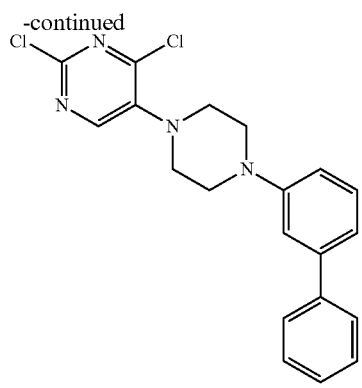

A mixture of 5-(4-([1,1'-biphenyl]-3-yl)piperazin-1-yl)pyrimidine-2,4(1H,3H)-dione (400.0 mg, 1.1 mmol, 1.0 eq) in POCl$_3$ (26.3 g, 171.6 mmol, 15.9 mL, 149.4 eq) was degassed and purged with N$_2$ 3 times, and then the mixture was stirred at 105° C. for 5 hours under N$_2$ atmosphere. LCMS was consistent with the desired product MS (385.1, RT=2.24 Min). The reaction mixture was concentrated under reduced pressure to give a black residue, diluted with H$_2$O (50 mL) and extracted with ethyl acetate (2×50 mL). The organic phase was dried over Na$_2$SO$_4$, filtered and concentrated under reduced pressure to give 5-(4-([1,1'-biphenyl]-3-yl)piperazin-1-yl)-2,4-dichloropyrimidine (250.0 mg, 649 μmol, 56.4% yield) as a yellow solid. LC/MS Method C (ESI+): Expected m/z 385 (M+1)$^+$; found m/z 385.1 (M+1)$^+$, RT: 2.24 Min.

Step 5. 5-(4-([1,1'-biphenyl]-3-yl)piperazin-1-yl)pyrimidine-2,4-diamine

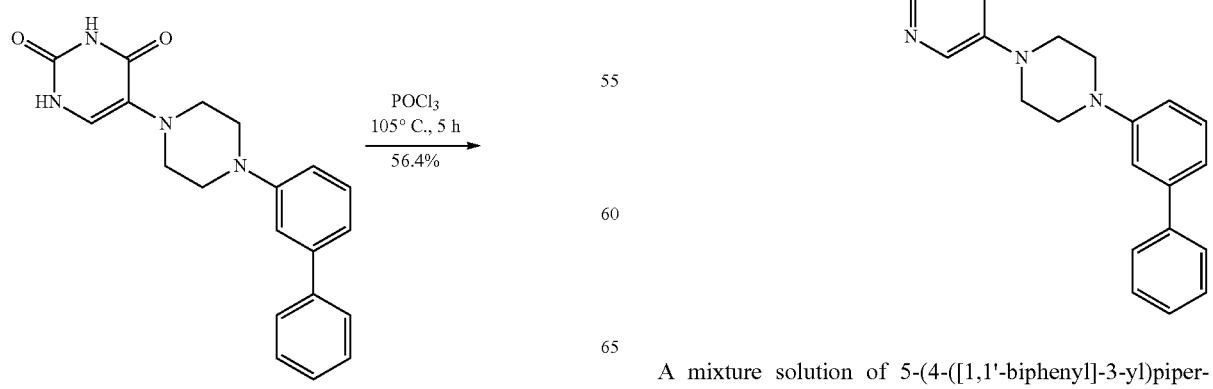

A mixture solution of 5-(4-([1,1'-biphenyl]-3-yl)piperazin-1-yl)-2,4-dichloropyrimidine (100.0 mg, 0.26 mmol, 1.0 eq) in NH₃/EtOH (10 mL) was added to a steel bomb. The mixture was stirred at 145° C. for 12 hours. The suspension was cooled to room temperature and concentrated under reduced pressure to give a brown residue. The residue was purified by Prep-HPLC (TFA condition) to give 5-(4-([1,1'-biphenyl]-3-yl)piperazin-1-yl)pyrimidine-2,4-diamine (86.5 mg, 249.6 µmol, 30.0% yield) as a white solid. LCMS Method D (ESI+): Expected m/z (347 M+1)⁺; found m/z 347.1 (M+1)⁺, Rt: 2.60 Min. ¹H NMR (MeOD 400 MHz) δ=7.64 (d, J=7.4 Hz, 2H), 7.59-7.55 (m, 2H), 7.54-7.49 (m, 1H), 7.46 (t, J=7.4 Hz, 3H), 7.38 (d, J=7.4 Hz, 1H), 7.36-7.30 (m, 1H), 3.66 (br.s., 4H), 3.18 (d, J=4.3 Hz, 4H).

The compounds listed in Table 1 were prepared using Synthetic Method A as for Compound 2 above by reacting 5-bromouracil with the appropriately substituted arylpiperazines.

TABLE 1

Compounds Prepared Using Synthetic Method A

| No. | IUPAC Name | LC/MS (M + 1) Expected MW | LC/MS (M + 1) Observed MW | ¹H NMR (400 MHz) |
|---|---|---|---|---|
| 1 | 5-(4-(3,4-dichlorophenyl)piperazin-1-yl)pyrimidine-2,4-diamine | 339 | 339 | (DMSO-d₆) δ = 8.40 (br.s., 1H), 7.62 (br.s., 1H), 7.54 (s, 1H), 7.48 (br.s., 2H), 7.38 (d, J = 9.3 Hz, 1H), 7.14 (d, J = 2.6 Hz, 1H), 6.94 (dd, J = 2.6, 8.8 Hz, 1H), 3.45-3.34 (m, 4H), 2.82 (br.s., 4H) |
| 2 | 5-(4-([1,1'-biphenyl]-3-yl)piperazin-1-yl)pyrimidine-2,4-diamine | 347.2 | 347.1 | (METHANOL-d₄) δ = 7.64 (d, J = 7.4 Hz, 2H), 7.59-7.55 (m, 2H), 7.54-7.49 (m, 1H), 7.46 (t, J = 7.4 Hz, 3H), 7.38 (d, J = 7.4 Hz, 1H), 7.36-7.30 (m, 1H), 3.66 (br.s., 4H), 3.18 (d, J = 4.3 Hz, 4H) |
| 3 | 5-(4-(3-(trifluoromethyl)phenyl)piperazin-1-yl)pyrimidine-2,4-diamine | 339.1 | 339.1 | (METHANOL-d₄) δ = 7.50 (s, 1H), 7.44-7.39 (m, 1H), 7.23 (br d, J = 8.8 Hz, 1H), 7.20 (br s, 1H), 7.10 (br d, J = 7.5 Hz, 1H), 3.40 (br s, 4H), 3.01 (br d, J = 4.4 Hz, 4H) |
| 4 | 5-(4-phenylpiperazin-1-yl)pyrimidine-2,4-diamine | 271.1 | 271.1 | (DMSO-d₆) δ = 7.59 (s, 1H), 7.22 (br t, J = 7.8 Hz, 2H), 6.96 (br d, J = 8.2 Hz, 2H), 6.78 (t, J = 7.0 Hz, 1H), 6.07 (br s, 2H), 5.61 (br s, 2H), 3.25 (br s, 4H), 2.88 (br t, J = 4.5 Hz, 4H) |
| 5 | 5-(4-(2-chlorophenyl)piperazin-1-yl)pyrimidine-2,4-diamine | 305.1 | 305.1 | (DMSO-d₆) δ = 7.62 (s, 1H), 7.42 (br d, J = 7.8 Hz, 1H), 7.35-7.28 (m, 1H), 7.18 (br d, J = 7.8 Hz, 1H), 7.05 (br t, J = 7.4 Hz, 1H), 6.09 (br s, 2H), 5.63 (s, 2H), 3.11 (br s, 4H), 2.91 (br d, J = 3.9 Hz, 4H) |
| 6 | 5-(4-(4-chlorophenyl)piperazin-1-yl)pyrimidine-2,4-diamine | 305.1 | 305.1 | (DMSO-d₆) δ = 7.58 (s, 1H), 7.24 (br d, J = 9.0 Hz, 2H), 6.97 (br d, J = 9.0 Hz, 2H), 6.08 (br s, 1H), 5.61 (s, 2H), 3.26 (br s, 4H), 2.86 (br t, J = 4.3 Hz, 4H) |
| 7 | 5-(4-(m-tolyl)piperazin-1-yl)pyrimidine-2,4-diamine | 285.1 | 285.1 | (DMSO-d₆) δ = 7.59 (s, 1H), 7.10 (t, J = 7.8 Hz, 1H), 6.83-6.70 (m, 2H), 6.60 (br d, J = 7.4 Hz, 1H), 6.08 (br s, 2H), 5.62 (s, 2H), 3.23 (br s, 4H), 2.86 (br t, J = 4.3 Hz, 4H), 2.25 (s, 3H) |

TABLE 1-continued

Compounds Prepared Using Synthetic Method A

| No. | IUPAC Name | LC/MS (M + 1) Expected MW | LC/MS (M + 1) Observed MW | $^1$H NMR (400 MHz) |
|---|---|---|---|---|
| 8 | 5-(4-(p-tolyl)piperazin-1-yl)pyrimidine-2,4-diamine | 285.1 | 285.1 | (DMSO-$d_6$) δ = 7.58 (s, 1H), 7.03 (d, J = 8.4 Hz, 2H), 6.86 (d, J = 8.4 Hz, 2H), 6.06 (br. s., 1H), 5.60 (s, 2H), 3.19 (br. s., 4H), 2.87 (d, J = 4.0 Hz, 4H), 2.20 (s, 3H) |
| 9 | 5-(4-(3-methoxyphenyl)piperazin-1-yl)pyrimidine-2,4-diamine | 301.1 | 301.1 | (DMSO-$d_6$) δ = 7.58 (s, 1H), 7.11 (t, J = 8.4 Hz, 1H), 6.54 (br d, J = 8.0 Hz, 1H), 6.47 (s, 1H), 6.37 (br d, J = 8.0 Hz, 1H), 6.08 (br s, 1H), 5.61 (s, 2H), 3.72 (s, 3H), 3.25 (br s, 4H), 2.86 (br d, J = 4.0 Hz, 4H) |
| 10 | 5-(4-(2-cyclopropylphenyl)piperazin-1-yl)pyrimidme-2,4-diamine | 311.19 | 311.1 | (CDCl$_3$) δ = 7.81 (s, 1H), 7.18-7.12 (m, 1H), 7.08-6.99 (m, 2H), 6.80 (d, J = 7.6 Hz, 1H), 5.13 (br s, 1H), 4.59 (br s, 2H), 3.15 (br s, 4H), 3.07-3.02 (m, 4H), 2.42-2.30 (m, 1H), 1.05-0.98 (m, 2H), 0.76-0.71 (m, 2H) |
| 11 | 5-(4-(3-bromophenyl)piperazin-1-yl)pyrimidine-2,4-diamine | 349.0 and 351.10 | 349.0 and 351.1 | (DMSO-$d_6$) δ = 7.57 (s, 1H), 7.19-7.12 (m, 1H), 7.09 (br s, 1H), 6.94 (br dd, J = 7.9, 18.4 Hz, 2H), 5.65 (s, 2H), 3.29 (br s, 4H), 2.85 (br s, 4H) |
| 12 | 5-(4-([1,1'-biphenyl]-4-yl)piperazin-1-yl)pyrimidine-2,4-diamine | 347.2 | 347.2 | (METHANOL-$d_4$) δ = 7.60-7.50 (m, 5H), 7.39 (br t, J = 7.4 Hz, 2H), 7.30-7.23 (m, 1H), 7.10 (br d, J = 8.6 Hz, 2H), 3.48-3.36 (m, 4H), 3.03 (br d, J = 4.3 Hz, 4H) |
| 13 | 5-(4-([1,1'-biphenyl]-2-yl)piperazin-1-yl)pyrimidine-2,4-diamine | 347.19 | 347.2 | (DMSO-$d_6$) δ = 7.65 (br d, J = 7.6 Hz, 2H), 7.48 (s, 1H), 7.44 (br t, J = 7.2 Hz, 2H), 7.31 (br t, J = 7.2 Hz, 2H), 7.21 (br d, J =7.2 Hz, 1H), 7.12-7.05 (m, 2H), 5.99 (br s, 1H), 5.60 (s, 2H), 2.88 (br s, 4H), 2.64 (br s, 4H) |
| 14 | 5-(4-(o-tolyl)piperazin-1-yl)pyrimidine-2,4-diamine | 285.17 | 285.1 | (MeOD) δ = 7.53 (s, 1H), 7.21-7.11 (m, 3H), 7.03-6.97 (m, 1H), 3.10 (br s, 4H), 3.03 (br d, J = 4.0 Hz, 4H), 2.34 (s, 3H) |
| 15 | 5-(4-phenylpiperidin-1-yl)pyrimidine-2,4-diamine | 270.16 | 270.1 | (METHANOL-$d_4$) δ = 7.45 (s, 1H), 7.31-7.26 (m, 4H), 7.21-7.15 (m, 1H), 3.16 (br d, J = 11.6 Hz, 2H), 2.79-2.60 (m, 3H), 2.06-1.93 (m, 2H), 1.93-1.85 (m, 2H) |

TABLE 1-continued

Compounds Prepared Using Synthetic Method A

| No. | IUPAC Name | LC/MS (M + 1) Expected MW | LC/MS (M + 1) Observed MW | $^1$H NMR (400 MHz) |
|---|---|---|---|---|
| 16 | 5-(4-(4-cyclopropylphenyl)piperazin-1-yl)pyrimidine-2,4-diamine | 311.2 | 311.1 | (METHANOL-d$_4$) δ = 7.53 (s, 1H), 7.09 (s, 4H), 3.44 (br s, 4H), 3.08 (br s, 4H), 1.88 (br s, 1H), 0.94 (br d, J = 8.0 Hz, 2H), 0.63 (br s, 2H) |
| 17 | 5-(4-(3,5-difluorophenyl)piperazin-1-yl)pyrimidine-2,4-diamine | 307.1 | 307.1 | (DMSO-d$_6$) δ = 7.59 (s, 1H), 6.61-6.53 (m, 2H), 6.44-6.33 (m, 1H), 5.90 (br s, 2H), 5.38 (s, 2H), 3.33 (t, J = 4.8 Hz, 4H), 2.85 (t, J = 4.8 Hz, 4H) |
| 18 | 5-(4-(3-fluoro-5-methoxyphenyl)piperazin-1-yl)pyrimidine-2,4-diamine | 319.2 | 319.1 | (METHANOL-d$_4$) δ = 7.46 (s, 1H), 6.39-6.28 (m, 2H), 6.23-6.08 (m, 1H), 3.74 (s, 3H), 3.35 (br dd, J = 2.4, 13.8 Hz, 4H), 2.97 (br d, J = 4.6 Hz, 4H) |
| 19 | 5-(4-(quinolin-3-yl)piperazin-1-yl)pyrimidine-2,4-diamine | 322.2 | 322.1 | (METHANOL-d$_4$) δ = 9.13 (d, J = 3.1 Hz, 1H), 8.42 (br s, 1H), 8.10 (br d, J = 7.6 Hz, 1H), 8.06 (br d, J = 8.4 Hz, 1H), 7.87-7.78 (m, 2H), 7.55 (s, 1H), 3.68 (br s, 4H), 3.09 (br s, 4H) |
| 20 | 5-(4-(pyridin-4-yl)piperazin-1-yl)pyrimidine-2,4-diamine | 272.15 | 272.1 | (MeOD-d$_4$) δ = 8.16 (d, J = 7.6 Hz, 2H), 7.50 (s, 1H), 7.22 (d, J = 7.6 Hz, 2H), 3.90 (br s, 4H), 3.00 (br s, 4H) |
| 21 | 5-(4-(2,6-dimethylpyridin-4-yl)piperazin-1-yl)pyrimidine-2,4-diamine | 300.19 | 300.1 | (MeOD-d$_4$) δ = 7.50 (s, 1H), 6.93 (s, 2H), 3.84 (br s, 4H), 2.97 (br s, 4H), 2.50 (s, 6H) |
| 22 | 5-(4-(3-chlorophenyl)piperazin-1-yl)pyrimidine-2,4-diamine | 305.1 | 305.1 | (DMSO-d$_6$) δ = 11.76 (br, 1H), 8.43 (br s, 1H), 7.65 (br s, 1H), 7.56 (br s, 1H), 7.43 (br s, 2H), 7.23 (br t, J = 8.4 Hz, 1H), 6.98 (br s, 1H), 6.93 (br d, J = 8.4 Hz, 1H), 6.80 (br d, J = 7.6 Hz, 1H), 3.36 (br s, 4H), 2.86 (br s, 4H) |
| 23 | 5-(4-(3-(trifluoromethoxy)phenyl)piperazin-1-yl)pyrimidine-2,4-diamine | 355.14 | 355.1 | (METHANOL-d$_4$) δ = 7.49 (s, 1H), 7.31 (t, J = 8.2 Hz, 1H), 6.98 (d, J = 7.9 Hz, 1H), 6.84 (s, 1H), 6.72 (d, J = 7.9 Hz, 1H), 3.38 (s, 4H), 2.99 (s, 4H) |
| 24 | 5-(4-(3-chloro-5-methylphenyl)piperazin-1-yl)pyrimidine-2,4-diamine | 319.1 | 319.1 | (METHANOL-d$_4$) δ = 7.48 (s, 1H), 6.79 (s, 1H), 6.75 (s, 1H), 6.68 (s, 1H), 3.34-3.31 (m, 4H), 2.99-2.98 (m, 4H), 2.28 (s, 3H) |
| 25 | 5-(4-(3-morpholinophenyl)piperazin-1-yl)pyrimidine-2,4-diamine | 356.21 | 356.1 | (METHANOL-d$_4$) δ = 7.53 (s, 1H), 7.30 (t, J = 4.4 Hz, H1), 6.92-6.84 (m, 1H), 6.91-6.80 (m, 1H), 6.82-6.78 (m, 1H), 3.92-3.85 (m, 4H), 3.49 (s, 4H), 3.31-3.25 (m, 4H), 3.08 (s, 4H) |

The compounds listed in Table 2 were prepared using Synthetic Method A as above by reacting 5-bromouracil with 1-([1,1'-biphenyl]-3-yl)-3-methylpiperazine or 1-([1,1'-biphenyl]-3-yl)-2-methylpiperazine.

TABLE 2

Compounds Prepared Using Synthetic Method A

| No. | IUPAC Name | LC/MS (M + 1) Expected MW | LC/MS (M + 1) Observed MW | $^1$H NMR (400 MHz) |
|---|---|---|---|---|
| 26 | 5-(4-([1,1'-biphenyl]-3-yl)-3-methylpiperazin-1-yl)pyrimidine-2,4-diamine | 361.2 | 361.1 | (METHANOL-$d_4$) δ = 7.80 (br d, J = 19.2 Hz, 2H), 7.73-7.62 (m, 4H), 7.55 (br s, 1H), 7.50 (t, J = 7.6 Hz, 2H), 7.47-7.39 (m, 1H), 4.26 (ddd, J = 3.2, 6.4, 9.5 Hz, 1H), 4.00 (br s, 1H), 3.76 (br d, J = 12.0 Hz, 1H), 3.45-3.34 (m, 2H), 3.28-3.19 (m, 1H), 3.12 (dd, J = 9.6, 12.8 Hz, 1H), 1.18 (d, J = 6.4 Hz, 3H) |
| 27 | 5-(4-([1,1'-biphenyl]-3-yl)-2-methylpiperazin-1-yl)pyrimidine-2,4-diamine | 361.2 | 361.1 | (METHANOL-$d_4$) δ = 7.67 (s, 1H), 7.60 (br d, J = 7.5 Hz, 2H), 7.43 (t, J = 7.6 Hz, 2H), 7.34 (q, J = 8.4 Hz, 2H), 7.24 (s, 1H), 7.15 (br d, J = 7.6 Hz, 1H), 7.05 (br d, J = 6.4 Hz, 1H), 3.78-3.62 (m, 2H), 3.27-3.05 (m, 3H), 3.04-2.91 (m, 1H), 2.82 (br s, 1H), 1.06 (d, J = 6.4 Hz, 3H) |

The compounds listed in Table 3 were prepared using Synthetic Method A as above by reacting 5-bromo-6-ethyluracil with the appropriately substituted arylpiperazine or 4-arylpiperidine.

TABLE 3

Compounds Prepared Using Synthetic Method A (arylpiperazine or 4-arylpiperidine)

| No. | IUPAC Name | LC/MS (M + 1) Expected MW | LC/MS (M + 1) Observed MW | $^1$H NMR (400 MHz) |
|---|---|---|---|---|
| 28 | 6-ethyl-5-(4-phenylpiperazin-1-yl)pyrimidine-2,4-diamine | 299.2 | 299.1 | (METHANOL-$d_4$) δ = 7.36 (d, J = 6.4 Hz, 2H), 7.22 (d, J = 7.6 Hz, 2H), 7.08 (d, J = 6.8 Hz, 1H), 3.58 (d, J = 10.4 Hz, 2H), 3.43-3.31 (m, 4H), 3.11 (d, J = 6.0 Hz, 2H), 2.71 (d, J = 7.2 Hz, 2H), 1.32 (t, J = 6.8 Hz, 3H) |
| 29 | 5-(4-([1,1'-biphenyl]-3-yl)piperazin-1-yl)-6-ethylpyrimidine-2,4-diamine | 375.2 | 375.1 | (METHANOL-$d_4$) δ = 7.61 (d, J = 7.2 Hz, 2H), 7.43 (d, J = 8.0 Hz, 4H), 7.36 (d, J = 6.4 Hz, 1H), 7.30 (d, J = 7.2 Hz, 1H), 7.18 (d, J = 7.2 Hz, 1H), 3.65 (d, J = 9.2 Hz, 2H), 3.44-3.31 (m, 4H), 3.12 (d, J = 8.8 Hz, 2H), 2.73 (d, J = 7.6 Hz, 2H), 1.33 (t, J = 6.8 Hz, 3H) |
| 30 | 5-(4-(3-chlorophenyl)piperazin-1-yl)-6-ethylpyrimidme-2,4-diamine | 333.1 | 333.1 | (METHANOL-$d_4$) δ = 7.25-7.17 (m, 1H), 6.99 (br s, 1H), 6.93 (br d, J = 7.9 Hz, 1H), 6.83 (br d, J = 7.9 Hz, 1H), 3.56 (br d, J = 11.0 Hz, 2.H), 3.28-3.20 (m, 2H), 3.16-2.99 (m, 4H), 2.70 (br d, J = 7.5 Hz, 2H), 1.32 (br t, J = 6.8 Hz, 3H) |

TABLE 3-continued

Compounds Prepared Using Synthetic Method A (arylpiperazine or 4-arylpiperidine)

| No. | IUPAC Name | LC/MS (M + 1) Expected MW | LC/MS (M + 1) Observed MW | $^1$H NMR (400 MHz) |
|---|---|---|---|---|
| 31 | 6-ethyl-5-(4-(m-tolyl)piperazin-1-yl)pyrimidine-2,4-diamine | 313.2 | 313.1 | (METHANOL-d$_4$) δ = 7.34-7.27 (m, 1H), 7.18 (s, 1H), 7.14 (br d, J = 8.2 Hz, 1H), 7.03 (d, J = 7.5 Hz, 1H), 3.65-3.53 (m, 2H), 3.52-3.41 (m, 4H), 3.20-3.10 (m, 2H), 2.72 (q, J = 7.7 Hz, 2H), 2.38 (s, 3H), 1.33 (t, J = 7.6 Hz, 3H) |
| 32 | 6-ethyl-5-(4-(3-fluorophenyl)piperazin-1-yl)pyrimidine-2,4-diamine | 317.2 | 317.2 | (METHANOL-d$_4$) δ = 7.27-7.19 (m, 1H), 6.82 (dd, J = 2.2, 8.4 Hz, 1H), 6.74 (td, J = 2.3, 12.3 Hz, 1H), 6.56 (dt, J = 2.4, 8.3 Hz, 1H), 3.57 (br d, J = 12.1 Hz, 2H), 3.30-3.23 (m, 2H), 3.17-3.08 (m, 2H), 3.04 (br d, J = 11.5 Hz, 2H), 2.70 (q, J = 7.5 Hz, 2H), 1.31 (t, J = 7.6 Hz, 3H) |
| 33 | 6-ethyl-5-(4-(3-methoxyphenyl)piperazin-1-yl)pyrimidine-2,4-diamine | 329.2 | 329.1 | (METHANOL-d$_4$) δ = 7.27-7.22 (m, 1H), 6.77 (d, J = 8.0 Hz, 1H), 6.74-6.72 (m, 1H), 6.62 (br d, J = 8.4 Hz, 1H), 3.79 (s, 3H), 3.56 (br d, J = 11.6 Hz, 2H), 3.41-3.33 (m, 2H), 3.29-3.24 (m, 2H), 3.08 (br d, J = 11.6 Hz, 2H), 2.71 (q, J = 7.6 Hz, 2H), 1.32 (t, J = 7.6 Hz, 3H) |
| 34 | 6-ethyl-5-(4-(pyridin-2-yl)piperazin-1-yl)pyrimidine-2,4-diamine | 300.19 | 300.1 | (METHANOL-d$_4$) δ = 8.02-7.98 (m, 2H), 7.36 (d, J = 10.0 Hz, 1H), 6.98 (t, J = 6.6 Hz, 1H), 4.07 (d, J = 12.4 Hz, 2H), 3.61 (t, J = 10.2 Hz, 2H), 3.27-3.22 (m, 2H), 3.12 (d, J = 12.0 Hz, 2H), 2.69-2.63 (m, 2H), 1.29 (t, J = 7.8 Hz, 3H). |
| 35 | 6-ethyl-5-(4-(4-fluorophenyl)piperazin-1-yl)pyrimidine-2,4-diamine | 317.18 | 317.1 | (METHANOL-d$_4$) δ = 7.14-7.11 (m, 2H), 7.04 (t, J = 8.8 Hz, 2H), 3.46 (d, J = 11.6 Hz, 2H), 3.34 (d, J = 11.6 Hz, 2H), 3.16 (t, J = 11.2 Hz, 2H), 3.06 (d, J = 11.6 Hz, 2H), 2.76-2.68 (m, 2H), 1.32 (t, J = 7.6 Hz, 3H) |
| 36 | 6-ethyl-5-(4-(pyridin-4-yl)piperazin-1-yl)pyrimidine-2,4-diamine | 300.1 | 300.1 | (METHANOL-d$_4$) δ = 8.13 (d, J = 7.6 Hz, 2H), 7.19 (d, J = 7.6 Hz, 2H), 4.15 (br d, J = 12.4 Hz, 2H), 3.62 (br t, J = 9.6 Hz, 2H), 3.23-3.06 (m, 4H), 2.68-2.56 (m, 2H), 1.27 (t, J = 7.6 Hz, 3H) |
| 37 | 6-ethyl-5-(4-(pyridin-3-yl)piperazin-1-yl)pyrimidine-2,4-diamine | 300.1 | 300.1 | (METHANOL-d$_4$) δ = 8.41 (s, 1H), 8.16-8.08 (m, 2H), 7.86-7.81 (m, 1H), 3.83 (br d, J = 11.8 Hz, 2H), 3.42-3.36 (m, 3H), 3.29-3.21 (m, 1H), 3.11 (br d, J = 12.0 Hz, 2H), 2.74-2.62 (m, 2H), 1.31 (t, J = 7.6 Hz, 3H) |
| 38 | 6-ethyl-5-(4-phenylpiperidin-1-yl)pyrimidine-2,4-diamine | 298.2 | 298.2 | (METHANOL-d$_4$) δ = 7.32-7.27 (m, 4H), 7.21-7.15 (m, 1H), 3.19 (dt, J = 2.4, 11.6 Hz, 2H), 3.01 (br d, J = 11.2 Hz, 2H), 2.75-2.67 (m, 2H), 2.67-2.60 (m, |

TABLE 3-continued

Compounds Prepared Using Synthetic Method A (arylpiperazine or 4-arylpiperidine)

| No. | IUPAC Name | LC/MS (M + 1) Expected MW | LC/MS (M + 1) Observed MW | $^1$H NMR (400 MHz) |
|---|---|---|---|---|
| | | | | 1H), 1.97 (dq, J = 4.0, 12.4 Hz, 2H), 1.89-1.83 (m, 2H), 1.33 (t, J = 7.6 Hz, 3H) |
| 39 | 6-ethyl-5-(4-(p-tolyl)piperazin-1-yl)pyrimidine-2,4-diamine | 313.3 | 313.3 | (METHANOL-d$_4$) δ = 7.27 (s, 4H), 3.61-3.43 (m, 6H), 3.19-3.13 (m, 2H), 2.72 (q, J = 7.6 Hz, 2H), 2.34 (s, 3H), 1.33 (t, J = 7.6 Hz, 3H) |
| 40 | 6-ethyl-5-(4-(4-methoxyphenyl)piperazin-1-yl)pyrimidine-2,4-diamine | 329.32 | 329.3 | (METHANOL-d$_4$) δ = 7.46 (br d, J = 9.2 Hz, 2H), 7.06 (d, J = 8.8 Hz, 2H), 3.83 (s, 3H), 3.74-3.63 (m, 2H), 3.62-3.50 (m, 4H), 3.20 (br d, J = 12.0 Hz, 2H), 2.72 (q, J = 7.6 Hz, 2H), 1.38-1.30 (m, 3H) |
| 41 | 5-(4-(5-chloropyndin-2-yl)piperazin-1-yl)-6-ethylpyrimidine-2,4-diamine | 334.1 | 334.2 | (METHANOL-d$_4$) δ = 8.07 (d, J = 2.4 Hz, 1H), 7.65 (dd, J = 2.4, 9.2 Hz, 1H), 6.99 (d, J = 9.6 Hz, 1H), 4.08 (br d, J = 12.8 Hz, 2H), 3.41-3.33 (m, 2H), 3.23-3.13 (m, 2H), 3.07-3.00 (m, 2H), 2.65 (q, J = 7.2, 11.6 Hz, 2H), 1.31-1.24 (m, 3H) |
| 42 | 6-ethyl-5-(4-(3-morpholinophenyl)piperazin-1-yl)pyrimidine-2,4-diamine | 384.24 | 384.1 | (METHANOL-d$_4$) δ = 7.31-7.27 (m, 1H), 3.89 (s, 1H), 6.83-6.81 (m, 1H), 6.78 (s, 1H), 3.86-3.88 (m, 4H), 3.57-3.60 (m, 2H), 3.37-3.40 (m, 4H), 3.23-3.25 (m, 4H), 3.12-3.10 (m, 2H), 2.70-2.72 (q, J = 7.6 Hz, 2H), 1.31-1.35 (t, J = 7.6 Hz, 3H) |
| 43 | 6-ethyl-5-(4-(3-(tetrahydro-2H-pyran-4-yl)phenyl)piperazin-1-yl)pyrimidine-2,4-diamine | 383.25 | 383.3 | (METHANOL-d$_4$) δ = 7.39 (t, J = 7.6 Hz, 1H), 7.29 (s, 1H), 7.22 (dd, J = 1.6, 8.0 Hz, 1H), 7.14 (d, J = 8.0 Hz, 1H), 4.08-4.02 (m, 2H), 3.65-3.45 (m, 8H), 3.21-3.13 (m, 2H), 2.85 (tt, J = 5.2, 10.4 Hz, 1H), 2.72 (q, J = 7.6 Hz, 2H), 1.87-1.75 (m, 4H), 1.34 (t, J = 7.6 Hz, 3H) |
| 44 | 6-ethyl-5-(4-(5-fluoropyridin-2-yl)piperazin-1-yl)pyrimidine-2,4-diamine | 317.2 | 317.4 | (METHANOL-d$_4$) δ = 8.03 (d, J = 3.2 Hz, 1H), 7.55 (ddd, J = 3.2, 8.0, 9.6 Hz, 1H), 7.01 (dd, J = 3.2, 9.6 Hz, 1H), 4.02 (br d, J = 12.4 Hz, 2H), 3.37-3.32 (m, 2H), 3.25-3.16 (m, 2H), 3.04 (br d, J = 11.6 Hz, 2H), 2.67 (q, J = 7.6 Hz, 2H), 1.30 (t, J = 7.6 Hz, 3H) |
| 45 | 6-ethyl-5-(4-(5-methylpyridin-2-yl)piperazin-1-yl)pyrimidine-2,4-diamine | 313.2 | 313.4 | (METHANOL-d$_4$) δ = 7.92 (dd, J = 2.0, 9.6 Hz, 1H), 7.81 (s, 1H), 7.34 (d, J = 9.6 Hz, 1H), 4.03 (br d, J = 13.2 Hz, 2H), 3.64-3.56 (m, 2H), 3.29-3.20 (m, 2H), 3.17-3.09 (m, 2H), 2.70-2.62 (m, 2H), 2.30 (s, 3H), 1.30 (t, J = 7.6 Hz, 3H) |

The compounds listed in Table 4 were prepared using Synthetic Method A as above by reacting 5-bromo-6-methyluracil with the appropriately substituted arylpiperazine.

TABLE 4

Compounds Prepared Using Synthetic Method A

| Compd # | IUPAC Name | LC/MS (M + 1) Expected MW | LC/MS (M + 1) Observed MW | $^1$H NMR (400 MHz) |
|---|---|---|---|---|
| 46 | 5-(4-(3-chlorophenyl)piperazin-1-yl)-6-methylpyrimidine-2,4-diamine | 319.1 | 319.1 | (DMSO-d$_6$) δ = 11.85 (br s, 1H), 8.28 (br s, 1H), 7.55 (br s, 1H), 7.33 (br s, 1H), 7.22 (br t, J = 8.0 Hz, 1H), 6.97 (br s, 1H), 6.93 (br d, J = 8.0 Hz, 1H), 6.79 (br d, J = 7.2 Hz, 1H), 3.53 (br s, 2H), 3.18-3.08 (m, 4H), 2.89 (br s, 2H), 2.25 (s, 3H) |
| 47 | 6-methyl-5-(4-phenylpiperazin-1-yl)pyrimidine-2,4-diamine | 285.1 | 285.1 | (METHANOL-d$_4$) δ = 7.25 (br t, J = 8.0 Hz, 2H), 7.02 (br d, J = 8.0 Hz, 2H), 6.86 (t, J = 7.2 Hz, 1H), 3.54 (br d, J = 11.2 Hz, 2H), 3.38-3.32 (m, 2H), 2.98 (br t, J = 11.2 Hz, 2H), 2.90 (br d, J = 11.3 Hz, 2H), 2.24 (s, 3H) |
| 48 | 5-(4-([1,1'-biphenyl]-3-yl)piperazin-1-yl)-6-methylpyrimidine-2,4-diamine | 361.21 | 361.1 | (METHANOL-d$_4$) d = 7.64-7.57 (m, 2H), 7.51-7.28 (m, 5H), 7.20 (br d, J = 7.5 Hz, 1H), 7.09 (br d, J = 7.9 Hz, 1H), 3.66 (br d, J = 11.5 Hz, 2H), 3.45-3.35 (m, 2H), 3.26-3.16 (m, 2H), 3.03 (br d, J = 11.5 Hz, 2H), 2.38 (s, 3H) |

The compounds listed in Table 5 were prepared using Synthetic Method A as above by reacting 5-bromo-6-n-propyluracil with the appropriately substituted arylpiperazine.

TABLE 5

Compounds Prepared Using Synthetic Method A

| Compd # | IUPAC Name | LC/MS (M + 1) Expected MW | LC/MS (M + 1) Observed MW | $^1$H NMR (400 MHz) |
|---|---|---|---|---|
| 49 | 5-(4-phenylpiperazin-1-yl)-6-propylpyrimidine-2,4-diamine | 313.2 | 313.1 | (METHANOL-d$_4$) δ = 7.34-7.24 (m, 2H), 7.09 (br d, J = 7.9 Hz, 2H), 6.94 (br s, 1H), 3.52 (br d, J = 11.0 Hz, 2H), 3.23-3.13 (m, 4H), 3.07 (br d, J = 10.1 Hz, 2H), 2.65 (br d, J = 7.9 Hz, 2H), 1.74 (br d, J = 6.2 Hz, 2H), 1.10 (br t, J = 6.8 Hz, 3H) |
| 50 | 5-(4-(6-methylpyridin-3-yl)piperazin-1-yl)-6-propylpyrimidine-2,4-diamine | 328.2 | 328.2 | (METHANOL-d$_4$) δ = 8.21 (d, J = 2.8 Hz, 1H), 8.02 (dd, J = 2.8, 9.2 Hz, 1H), 7.65 (d, J = 9.2 Hz, 1H), 3.71 (br d, J = 11.6 Hz, 2H), 3.30-3.20 (m, 4H), 3.15-3.07 (m, 2H), 2.66-2.59 (m, 5H), 1.73 (qd, J = 7.6, 15.6 Hz, 2H), 1.07 (t, J = 7.6 Hz, 3H) |
| 51 | 5-(4-phenylpiperidin-1-yl)-6-propylpyrimidine-2,4-diamine | 312.2 | 311.4 | (METHANOL-d$_4$) δ = 7.33-7.25 (m, 4H), 7.21-7.15 (m, 1H), 3.18 (dt, J = 2.4, 11.6 Hz, 2H), 3.01 (br d, J = 11.2 Hz, 2H), 2.79-2.67 (m, 1H), 2.66-2.59 (m, 2H), 2.04-1.91 (m, 2H), 1.90-1.81 (m, 2H), 1.74 (q, J = 7.6, 15.6 Hz, 2H), 1.14-1.04 (m, 3H) |

TABLE 5-continued

Compounds Prepared Using Synthetic Method A

| Compd # | IUPAC Name | LC/MS (M + 1) Expected MW | LC/MS (M + 1) Observed MW | ¹H NMR (400 MHz) |
|---|---|---|---|---|
| 52 | 5-(4-(4-fluorophenyl)piperazin-1-yl)-6-propylpyrimidine-2,4-diamine | 331.2 | 331.1 | (METHANOL-d$_4$) δ = 7.13-7.09 (m, 2H), 7.06-7.01 (m, 2H), 3.44 (br d, J = 12.0 Hz, 2H), 3.28 (s, 1H), 3.27 (s, 1H), 3.17-3.15 (m, 2H), 3.08-3.05 (m, 2H), 2.67-2.63 (m, 2H), 1.78-1.68 (m, 2H), 1.09 (t, J = 7.4 Hz, 3H) |
| 53 | 6-propyl-5-(4-(pyridin-4-yl)piperazin-1-yl)pyrimidine-2,4-diamine | 314.2 | 314.2 | (METHANOL-d$_4$) δ = 8.14 (d, J = 7.6 Hz, 2H), 7.20 (d, J = 7.6 Hz, 2H), 4.13 (br d, J = 13.6 Hz, 2H), 3.69-3.63 (m, 2H), 3.18-3.14 (m, 4H), 2.60-2.56 (m, 2H), 1.75-1.66 (m, 2H), 1.04 (t, J = 7.2 Hz, 3H) |
| 54 | 6-propyl-5-(4-(pyridin-3-yl)piperazin-1-yl)pyrimidine-2,4-diamine | 314.2 | 314.2 | (METHANOL-d$_4$) δ = 8.39 (d, J = 2.4 Hz, 1H), 8.12 (d, J = 5.6 Hz, 1H), 8.06-8.04 (m, 1H), 7.81-7.77 (m, 1H), 3.78 (br d, J = 12.0 Hz, 2H), 3.39-3.34 (m, 2H), 3.26-3.21 (m, 2H), 3.13-3.10 (m, 2H), 2.64-2.60 (m, 2H), 1.77-1.67 (m, 2H), 1.06 (t, J = 7.6 Hz, 3H) |
| 55 | 5-(4-(2-methylpyridin-4-yl)piperazin-1-yl)-6-propylpyrimidine-2,4-diamine | 328.22 | 328.2 | (METHANOL-d$_4$) δ = 8.02 (d, J = 7.6 Hz, 1H), 7.07 (t, J = 4.4 Hz, 2H), 4.10 (br d, J = 13.2 Hz, 2H), 3.66-3.59 (m, 2H), 3.16-3.10 (m, 4H), 2.59-2.55 (m, 2H), 2.53 (s, 3H), 1.75-1.65 (m, 2H), 1.04 (t, J = 7.2 Hz, 3H) |
| 56 | 6-propyl-5-(4-(pyridin-2-yl)piperazin-1-yl)pyrimidine-2,4-diamine | 314.2 | 314.2 | (METHANOL-d$_4$) δ = 8.02-7.99 (m, 2H), 7.37 (d, J = 9.6 Hz, 1H), 7.01-6.97 (m, 1H), 4.06 (br d, J = 12.8 Hz, 2H), 3.67-3.61 (m, 2H), 3.26-3.14 (m, 4H), 2.64-2.60 (m, 2H), 1.75-1.69 (m, 2H), 1.07 (t, J = 7.6 Hz, 3H) |
| 57 | 6-propyl-5-(4-(pyrimidin-2-yl)piperazin-1-yl)pyrimidine-2,4-diamine | 315.2 | 315.2 | (METHANOL-d$_4$) δ = 8.36 (d, J = 4.8 Hz, 2H), 6.63 (t, J = 5.2 Hz, 1H), 4.47 (br d, J = 12.8 Hz, 2H), 3.47 (br t, J = 9.6 Hz, 2H), 3.14-3.00 (m, 4H), 2.61-2.57 (m, 2H), 1.74-1.68 (m, 2H), 1.05 (t, J = 7.2 Hz, 3H) |
| 58 | 5-(4-(5-chloropyrimidin-2-yl)piperazin-1-yl)-6-propylpyrimidine-2,4-diamine | 349.16 | 349.1 | (METHANOL-d$_4$) δ = 8.29 (s, 2H), 4.46-4.36 (m, 2H), 3.49-3.88 (m, 2H), 3.07-2.95 (m, 4H), 2.58-2.48 (m, 2H), 1.75-1.58 (m, 2H), 1.01 (t, J = 7.2 Hz, 3H) |
| 59 | 5-(4-(5-methylpyrimidin-2-yl)piperazin-1-yl)-6-propylpyrimidine-2,4-diamine | 329.21 | 329.1 | (CDCl$_3$) δ = 8.26 (s, 2 H), 6.84-6.55 (m, 1 H), 5.91-5.63 (m, 1 H), 4.81-4.54 (m, 2 H), 3.16 (br dd, J = 8.8, 2.4 Hz, 4 H), 3.01-2.87 (m, 2 H), 2.68-2.49 (m, 2 H), 2.19 (s, 3 H), 1.80-1.60 (m, 2 H), 1.03 (t, J = 7.2 Hz, 3 H) |
| 60 | 5-(4-(5-methoxypyridin-2-yl)piperazin-1-yl)-6-propylpyrimidine-2,4-diamine | 344.21 | 344.4 | (METHANOL-d$_4$) δ = 7.80 (dd, J = 2.8, 10.0 Hz, 1H), 7.58 (d, J = 2.8 Hz, 1H), 7.39 (d, J = 10.0 Hz, 1H), 3.94 (br d, J = 12.8 Hz, 2H), 3.85 (s, 3H), 3.58-3.57 (m, 2H), 3.23-3.11 (m, 4H), 2.61-2.57 (m, 2H), 1.74-1.65 (m, 2H), 1.04 (t, J = 7.6 Hz, 3H) |
| 61 | 5-(4-(5-fluoropyrimidin-2-yl)piperazin-1-yl)-6-propylpyrimidine-2,4-diamine | 333.19 | 333.1 | (METHANOL-d$_4$) δ = 8.30 (s, 2H), 4.45-4.31 (m, 2H), 3.46-3.37 (m, 2H), 3.10-2.97 (m, 4H), 2.61-2.53 (m, 2H), 1.76-1.62 (m, 2H), 1.04 (t, J = 7.2 Hz, 3H) |

TABLE 5-continued

Compounds Prepared Using Synthetic Method A

| Compd # | IUPAC Name | LC/MS (M + 1) Expected MW | LC/MS (M + 1) Observed MW | $^1$H NMR (400 MHz) |
|---|---|---|---|---|
| 62 | 5-(4-(5-fluoropyridin-2-yl)piperazin-1-yl)-6-propylpyrimidine-2,4-diamine | 331.2 | 331.4 | (METHANOL-d$_4$) δ = 8.02 (d, J = 3.2 Hz, 1H), 7.45 (ddd, J = 3.2, 8.0, 9.2 Hz, 1H), 6.91 (dd, J = 3.2, 9.2 Hz, 1H), 3.98 (br d, J = 12.4 Hz, 2H), 3.27 (dd, J = 3.2, 12.4 Hz, 2H), 3.23-3.11 (m, 2H), 3.08-3.00 (m, 2H), 2.65-2.57 (m, 2H), 1.78-1.66 (m, 2H), 1.06 (t, J = 7.6 Hz, 3H) |
| 109 | 5-(4-(1-phenyl-1H-pyrazol-4-yl)piperazin-1-yl)pyrimidine-2,4-diamine | 337.2 | 337.2 | (CDCl3) δ = 7.69 (s, 1H), 7.59-7.56 (m, 2H), 7.42-7.41 (m, 2H), 7.41-7.34 (m, 2H), 7.18 (s, 1H), 5.10 (s, 1H), 4.70 (s, 2H), 3.12-3.00 (m, 4H), 2.98-2.95 (m, 4H) |
| 110 | 5-(4-([2,4'-bipyridin]-4-yl)piperazin-1-yl)pyrimidine-2,4-diamine | 349.2 | 349.2 | (DMSO-d$_6$) δ = 12.04 (s, 1H), 8.86 (d, J = 6.0 Hz, 2H), 8.47 (s, 1H), 8.37 (d, J = 7.2 Hz, 1H), 7.96 (d, J = 6.0 Hz, 2H), 7.84 (s, 1H), 7.63 (s, 1H), 7.59-7.56 (m, 2H), 7.32-7.30 (m, 1H), 3.96 (s, 4H), 2.90 (s, 4H) |
| 111 | 5-(4-(3-phenoxyphenyl)piperazin-1-yl)pyrimidine-2,4-diamine | 363.4 | 364.0 | (METHANOL-d4) δ = 7.47 (s, 1H), 7.34-7.29 (m, 2H), 7.23-7.20 (m, 1H), 7.12-7.05 (m, 1H), 6.97-6.94 (m, 2H), 6.81 (d, J = 1.2 Hz, 1H), 6.67 (s, 1H), 6.49-6.48 (m, 1H), 3.33 (s, 4H), 2.97 (m, 4H) |
| 112 | 5-(4-(6-(trifluoromethyl)pyridin-3-yl)piperazin-1-yl)pyrimidine-2,4-diamine | 340.1 | 340.1 | (DMSO-d6) δ = 8.48 (d, J = 1.6 Hz, 1H), 8.44 (s, 1H), 7.70-7.66 (m, 2H), 7.58 (s, 1H), 7.49 (d, J = 5.6 Hz, 3H), 3.56 (s, 4H), 2.89 (s, 4H) |
| 113 | 5-(4-(4-chloro-3-fluorophenyl)piperazin-1-yl)pyrimidine-2,4-diamine | 323.1 | 323.1 | (DMSO-d6) δ = 8.39 (br s, 1H), 7.62 (br s, 1H), 7.57 (s, 1H), 7.55 (s, 2H), 7.34 (t, J = 18 Hz, 1H), 6.85 (dd, J = 2.8, 13.2 Hz, 1H), 6.80 (dd, J = 2.4, 9.6 Hz, 1H), 3.34 (s, 4H), 2.84 (s, 4H) |
| 114 | 5-(4-(4-methoxyphenyl)piperazin-1-yl)pyrimidine-2,4-diamine | 301.2 | 301.2 | (DMSO-d6) δ = 7.59 (s. H) 6.90-6.83 (m, 4H), 6.07 (s, 2H), 5.62 (s, 2H), 3.69 (s, 3H), 3.13 (s, 4H), 2.87 (s, 4H) |
| 115 | 5-(4-(4-(trifluoromethyl)phenyl)piperazin-1-yl)pyrimidine-2,4-diamine | 339.2 | 339.1 | (DMSO-d6) δ = 7.57 (s, 1H), 7.52 (d, J = 8.8 Hz, 2H), 7.09 (d, J = 8.4 Hz, 2H), 6.84 (s, 1H), 6.32 (s, 2H), 3.43 (s, 4H), 2.86 (s, 4H) |
| 116 | 5-(4-(4-fluorophenyl)piperazin-1-yl)pyrimidine-2,4-diamine | 289.2 | 289.1 | (DMSO-d6) δ = 7.58 (s, 1H), 7.05-6.97 (m, 4H), 6.22 (s, 2H), 5.75 (s, 2H), 3.20 (s, 4H), 2.87 (s, 4H) |
| 117 | 5-(4-(3,4-difluorophenyl)piperazin-1-yl)pyrimidine-2,4-diamine | 307.3 | 307.2 | (DMSO-d6) δ = 8.42 (s, 1H), 7.63-7.57 (m, 2H), 7.49 (s, 2H), 7.28-7.23 (m, 1H), 7.05-7.00 (m, 1H), 6.76 (d, J = 9.2 Hz, 1H), 3.31 (s, 4H), 2.87 (s, 4H) |

Example 3: Synthetic Method B

According to Synthetic Method B, compounds of the invention can be prepared by Suzuki or Stille coupling reactions as shown below.

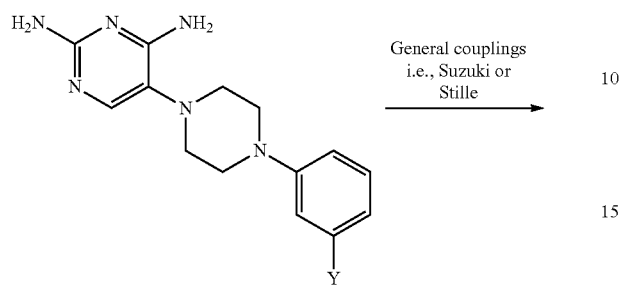

Y = Cl, Br or I
1008

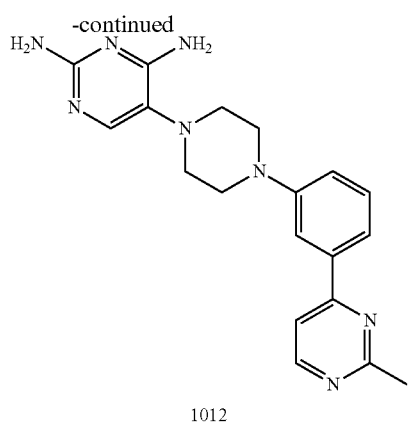

final targets
1009

The bromophenyl derivative 1010 can also be converted to the boronate 1011 as shown below, which can then undergo reaction with a variety of aryl or heteroaryl halides under Suzuki reaction conditions, as exemplified below for reaction with 4-chloro-2-methylpyrimidine to give final targets such as 1012.

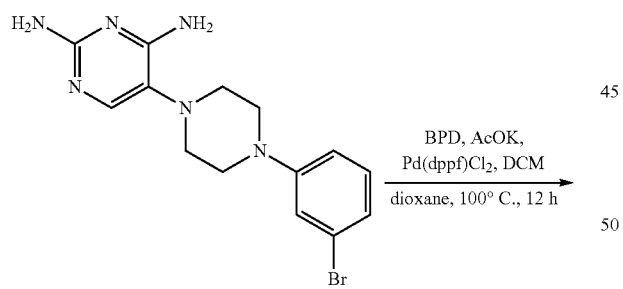

1010

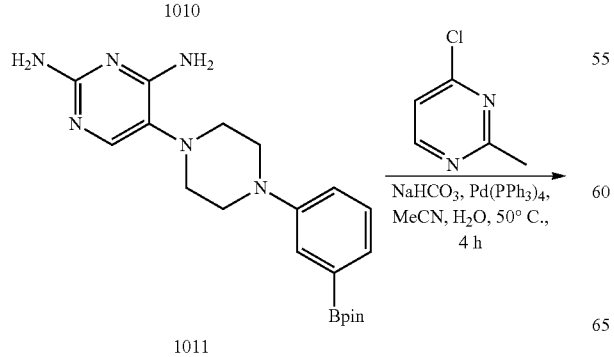

1011

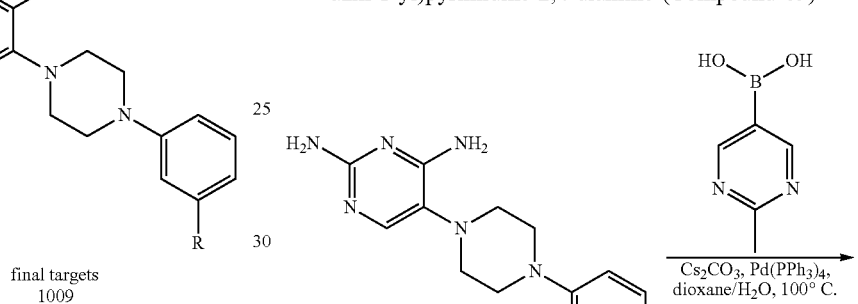

1012

Synthetic Method B is Exemplified in the Synthesis of 5-(4-(3-(2-methylpyrimidin-5-yl)phenyl)piperazin-1-yl)pyrimidine-2,4-diamine (Compound 69)

A mixture of 5-(4-(3-bromophenyl)piperazin-1-yl)pyrimidine-2,4-diamine (Compound 11) (1.0 g, 2.8 mmol, 1.0 eq), (2-methylpyrimidin-5-yl)boronic acid (394.9 mg, 2.8 mmol, 1.0 eq), $Cs_2CO_3$ (1.4 g, 4.3 mmol, 1.5 eq), $Pd(PPh_3)_4$ (165.4 mg, 143.2 umol, 0.05 eq) in dioxane (32.0 mL) and $H_2O$ (8.0 mL) was degassed and purged with $N_2$ for 3 times, and then stirred at 100° C. for 12 h under $N_2$ atmosphere. Then it was stirred with silica S thiol Met at 20° C., filtered and concentrated to give a residue. The residue was purified by prep-HPLC (TFA condition) to give 5-(4-(3-(2-methylpyrimidin-5-yl)phenyl)piperazin-1-yl)pyrimidine-2,4-diamine (1.2 g, 2.5 mmol, 88.0% yield) as a white solid. $^1$H NMR, 400 MHz, METHANOL-$d_4$) δ=8.93 (s, 2H), 7.51 (s, 1H), 7.41 (t, J=7.8 Hz, 1H), 7.26-7.24 (m, 1H), 7.16-7.09 (m, 2H), 3.44 (br s, 4H), 3.02 (br t, J=4.8 Hz, 4H), 2.73 (s, 3H).

TABLE 6

| | | Compounds Prepared Using Synthetic Method B | | |
|---|---|---|---|---|
| | | LC/MS (M + 1) | | |
| No. | IUPAC Name | Expected MW | Observed MW | $^1$H NMR (400 MHz) |
| 63 | 5-(4-(2',4'-difluoro-[1,1'-biphenyl]-3-yl)piperazin-1-yl)pyrimidine-2,4-diamine | 383.17 | 383.1 | (METHANOL-$d_4$) δ = 7.55-7.45 (m, 2H), 7.37 (t, J = 8.0 Hz. 1H), 7.09 (br s, 1H), 7.11-6.96 (m, 4H), 3.42 (br s, 4H), 3.04 (br d, J = 4.0 Hz, 4H) |
| 64 | 5-(4-(3'-fluoro-[1,1'-biphenyl]-3-yl)piperazin-1-yl)pyrimidine-2,4-diamine | 365.18 | 365.1 | (METHANOL-$d_4$) δ = 7.51 (s, 1H), 7.43 (br d, J = 2.8 Hz, 2H), 7.39-7.31 (m, 2H), 7.23 (br s, 1H), 7.14 (br d, J = 7.6 Hz, 1H), 7.06 (br d, J = 6.0 Hz, 2H), 3.43 (br s, 4H), 3.04 (br s, 4H) |
| 65 | 5-(4-(3',4'-difluoro-[1,1'-biphenyl]-3-yl)piperazin-1-yl)pyrimidine-2,4-diamine | 383.17 | 383.1 | (METHANOL-$d_4$) δ = 7.55-7.48 (m, 2H), 7.45-7.28 (m, 3H), 7.21 (br s, 1H), 7.15-7.03 (m, 2H), 3.44 (br s, 4H), 3.04 (br s, 4H) |
| 66 | 5-(4-(3-cyclopropylphenyl)piperazin-1-yl)pyrimidine-2,4-diamine | 311.19 | 311.1 | (METHANOL-$d_4$) δ = 7.52 (br s, 1H), 7.20 (br d, J = 7.2 Hz, 1H), 6.97-6.83 (m, 2H), 6.73 (br s, 1H), 3.43 (br s, 4H), 3.06 (br s, 4H), 1.91 (br s, 1H), 0.96 (br d, J = 6.0 Hz, 2H), 0.68 (br s, 2H) |
| 67 | 3'-(4-(2,4-diaminopyrimidin-5-yl)piperazin-1-yl)-[1,1'-biphenyl]-3-carbonitrile | 372.19 | 372.1 | (METHANOL-$d_4$) δ = 7.97 (s, 1H), 7.93 (br d, J = 8.4 Hz, 1H), 7.74-7.68 (m, 1H), 7.66-7.57 (m, 1H), 7.51 (s, 1H), 7.42-7.35 (m, 1H), 7.24 (s, 1H), 7.15 (br d, J = 7.6 Hz, 1H), 7.09 (br d, J = 8.0 Hz, 1H), 3.44 (br s, 4H), 3.03 (br s, 4H) |
| 68 | 5-(4-(3-(pyridin-4-yl)phenyl)piperazin-1-yl)pyrimidine-2,4-diamine | 348.19 | 348.1 | (METHANOL-$d_4$) δ = 8.56 (br s, 2.H), 7.73-7.62 (m, 3H), 7.39 (br d, J = 8.8 Hz, 1H), 7.33 (br s, 1H), 7.22 (br d, J = 7.2 Hz, 1H), 7.13 (br d, J = 7.6 Hz, 1H), 3.50-3.35 (m, 4H), 3.03 (br s, 4H) |
| 69 | 5-(4-(3-(2-methylpyrimidin-5-yl)phenyl)piperazin-1-yl)pyrimidine-2,4-diamine | 363.2 | 363.1 | (METHANOL-$d_4$) δ = 8.97 (s, 2H), 7.52 (s, 1H), 7.48-7.40 (m, 1H), 7.32 (s, 1H), 7.19 (br dd, J = 9.2, 17.2 Hz, 2H), 3.48 (br s, 4H), 3.05 (br s, 4H), 2.75 (s, 3H) |
| 70 | 5-(4-(4'-fluoro-[1,1'-biphenyl]-3-yl)piperazin-1-yl)pyrimidine-2,4-diamine | 365.18 | 365.2 | (METHANOL-$d_4$) δ = 7.66-7.57 (m, 2H), 7.52 (s, 1H), 7.36 (br t, J = 7.2 Hz, 1H), 7.24 (br s, 1H), 7.20-7.11 (m, 3H), 7.06 (br d, J = 7.2 Hz, 1H), 3.45 (br s, 4H), 3.05 (br s, 4H) |
| 71 | 5-(4-(3'-methoxy-[1,1'-biphenyl]-3-yl)piperazin-1-yl)pyrimidine-2,4-diamine | 377.2 | 377.2 | (METHANOL-$d_4$) δ = 7.54 (br s, 1H), 7.47-7.32 (m, 3H), 7.31-7.23 (m, 1H), 7.22-7.09 (m, 3H), 6.93 (br d, J = 8.0 Hz, 1H), 3.85 (br s, 3H), 3.53 (br s, 4H), 3.10 (br s, 4H) |

TABLE 6-continued

Compounds Prepared Using Synthetic Method B

| No. | IUPAC Name | LC/MS (M + 1) Expected MW | LC/MS (M + 1) Observed MW | ¹H NMR (400 MHz) |
|---|---|---|---|---|
| 72 | 5-(4-(3'-methyl-[1,1'-biphenyl]-3-yl)piperazin-1-yl)pyrimidine-2,4-diamine | 361.21 | 361.2 | (METHANOL-$d_4$) δ = 7.53 (s, 1H), 7.44-7.34 (m, 3H), 7.33-7.25 (m, 2H), 7.22-7.13 (m, 2H), 7.08 (br d, J = 7.6 Hz, 1H), 3.47 (br s, 4H), 3.06 (br s, 4H), 2.40 (s, 3H) |
| 73 | 5-(4-(3-(pyridazin-4-yl)phenyl)piperazin-1-yl)pyrimidine-2,4-diamine | 349.18 | 349.1 | (METHANOL-$d_4$) δ = 9.59 (s, 1H), 9.25 (d, J = 5.3 Hz, 1H), 8.10 (dd, J = 2.4, 5.5 Hz, 1H), 7.55-7.41 (m, 3H), 7.34 (br d, J = 7.9 Hz, 1H), 7.22 (br d, J = 8.4 Hz, 1H), 3.48 (br s, 4H), 3.04 (br d, J = 4.4 Hz, 4H) |
| 74 | 5-(4-(3-(pyrimidin-5-yl)phenyl)piperazin-1-yl)pyrimidine-2,4-diamine | 349.1 | 349.1 | (METHANOL-$d_4$) δ = 9.14 (br s, 1H), 9.07 (br s, 2H), 7.52 (s, 1H), 7.49-7.42 (m, 1H), 7.34 (br s, 1H), 7.21 (br dd, J = 7.7, 18.7 Hz, 2H), 3.48 (br s, 4H), 3.05 (br s, 4H) |
| 75 | 3'-(4-(2,4-diaminopyrimidin-5-yl)piperazin-1-yl)-[1,1'-biphenyl]-4-carbonitrile | 372.19 | 372.1 | (DMSO-$d_6$) δ = 7.90 (d, J = 1.2 Hz, 4H), 7.60 (s, 1H), 7.40-7.33 (m, 1H), 7.26 (s, 1H), 7.14 (d, J = 7.6 Hz, 1H), 7.07 (d, J = 2.0 Hz, 1H), 5.66 (s, 2H), 3.44-3.35 (m, 4H), 2.95-2.84 (m, 4H) |
| 76 | 5-(4-(5-bromo-[1,1'-biphenyl]-3-yl)piperazin-1-yl)pyrimidine-2,4-diamine | 425.1/427.1 | 425.1/427.1 | (METHANOL-d4) δ = 7.57 (d, J = 6.8 Hz, 2H), 7.50 (br. s., 1H), 7.44 (br. s., 2H), 7.37 (d, J = 6.8 Hz, 1H), 7.21 (br. s., 1H), 7.14 (br. s., 2H), 3.43 (br. s., 4H), 3.01 (br. s., 4H) |
| 77 | 5-(4-(3-(pyridin-3-yl)phenyl)piperazin-1-yl)pyrimidine-2,4-diamine | 348.2 | 348.2 | (METHANOL-$d_4$) δ = 9.08 (br s, 1H), 8.79-8.69 (m, 2H), 8.01 (br s, 1H), 7.52 (s, 1H), 7.49-7.44 (m, 1H), 7.36 (s, 1H), 7.24 (d, J = 7.6 Hz, 1H), 7.19 (dd, J = 2.0, 8.4 Hz, 1H), 3.48 (br s, 4H), 3.04 (br s, 4H) |
| 78 | 5-(4-(3-(2-methoxypyrimidin-5-yl)phenyl)piperazin-1-yl)pyrimidine-2,4-diamine | 379.2 | 379.1 | (METHANOL-$d_4$) δ = 8.81 (s, 2H), 7.51 (s, 1H), 7.39 (br t, J = 7.6 Hz, 1H), 7.22 (br s, 1H), 7.14-7.07 (m, 2H), 4.06 (s, 3H), 3.44 (br s, 4H), 3.03 (br s, 4H) |
| 79 | 5-(4-(3-(6-methoxypyridin-3-yl)phenyl)piperazin-1-yl)pyrimidine-2,4-diamine | 378.2 | 378.1 | (METHANOL-$d_4$) δ = 8.37 (s, 1H), 7.96 (d, J = 8.4 Hz, 1H), 7.52 (s, 1H), 7.37 (t, J = 8.0 Hz, 1H), 7.22 (s, 1H), 7.12 (d, J = 7.2 Hz, 1H), 7.06 (d, J = 8.4 Hz, 1H), 6.91 (d, J = 8.8 Hz, 1H), 3.96 (s, 3H), 3.44 (br s, 4H), 3.04 (s, 4H) |
| 80 | 5-(4-(3-(2-methoxypyridin-3-yl)phenyl)piperazin-1-yl)pyrimidine-2,4-diamine | 378.2 | 378.2 | (METHANOL-$d_4$) δ = 8.12 (d, J = 3.2 Hz, 1H), 7.69 (d, J = 6.4 Hz, 1H), 7.51 (s, 1H), 7.35-7.31 (m, 1H), 7.20 (s, 1H), 7.07-7.03 (m, 3H), 3.93 |

TABLE 6-continued

Compounds Prepared Using Synthetic Method B

| No. | IUPAC Name | LC/MS (M + 1) Expected MW | LC/MS (M + 1) Observed MW | ¹H NMR (400 MHz) |
|---|---|---|---|---|
| | | | | (s, 3H), 3.40 (br s, 4H), 3.03 (s, 4H) |
| 81 | 5-(4-(3-(2-fluoropyridin-3-yl)phenyl)piperazin-1-yl)pyrimidine-2,4-diamine | 366.2 | 366.2 | (METHANOL-d₄) δ = 8.18 (d, J = 4.0 Hz, 1H), 8.05 (t, J = 8.0 Hz, 1H), 7.51 (s, 1H), 7.46-7.36 (m, 2H), 7.22 (br. s., 1H), 7.11 (t, J = 9.6 Hz, 2H), 3.43 (br. s., 4H), 3.03 (br. s., 4H) |
| 82 | 5-(4-(3-(5-chloropyridin-3-yl)phenyl)piperazin-1-yl)pyrimidine-2,4-diamine | 382.1 | 382.1 | (METHANOL-d₄) δ = 8.75 (br s, 1H), 8.56 (br s, 1H), 8.16 (br s, 1H), 7.51 (s, 1H), 7.46-7.39 (m, 1H), 7.29 (br s, 1H), 7.17 (br dd, J = 7.6, 16.4 Hz, 2H), 3.47 (br s, 4H), 3.04 (br s, 4H) |
| 83 | 6-methyl-5-(4-(3-(2-methylpyrimidin-5-yl)phenyl)piperazin-1-yl)pyrimidine-2,4-diamine | 377.2 | 377.2 | (METHANOL-d₄) d = 8.96-8.92 (m, 2H), 7.46-7.38 (m, 1H), 7.28 (br s, 1H), 7.16 (br dd, J = 8.4, 15.5 Hz, 2H), 3.70 (br d, J = 11.2 Hz, 2H), 3.42-3.33 (m, 2H), 3.23-3.10 (m, 2H), 3.02 (br d, J = 11.2 Hz, 2H), 2.74 (s, 3H), 2.37 (s, 3H) |
| 84 | 5-(4-(3-(6-methylpyridin-3-yl)phenyl)piperazin-1-yl)pyrimidine-2,4-diamine | 362.2 | 362.2 | (METHANOL-d₄) δ 8.95 (s, 1H), 8.69 (br d, J = 8.4 Hz, 1H), 7.93 (br d, J = 8.4 Hz, 1H), 7.51 (s, 1H), 7.49-7.42 (m, 1H), 7.35 (br s, 1H), 7.23 (br d, J = 7.6 Hz, 1H), 7.18 (br d, J = 8.4 Hz, 1H), 3.61-3.37(m, 4H), 3.04 (br s, 4H), 2.81 (s, 3H) |
| 85 | 5-(4-(3-(6-fluoropyridin-3-yl)phenyl)piperazin-1-yl)pyrimidine-2,4-diamine | 366.1 | 366.1 | (METHANOL-d₄) δ = 8.43 (s, 1H), 8.21-8.14 (m, 1H), 7.51 (s, 1H), 7.43-7.36 (m, 1H), 7.22 (br s, 1H), 7.18-7.06 (m, 3H), 3.44 (br s, 4H), 3.03 (br s, 4H) |
| 86 | 5-(4-(3-(2-cyclopropylpyrimidin-5-yl)phenyl)piperazin-1-yl)pyrimidine-2,4-diamine | 389.21 | 389.2 | (METHANOL-d₄) δ = 8.89 (s, 2H), 7.52 (s, 1H), 7.43-7.41 (m, 1H), 7.28 (s, 1H), 7.19-7.13 (m, 2H), 3.46 (br s, 4H), 3.04 (br s, 4H), 2.30-2.25 (m, 1H), 1.17-1.15 (m, 4H) |
| 87 | 5-(4-(3-(2-(trifluoromethyl)pyrimidin-5-yl)phenyl)piperazin-1-yl)pyrimidine-2,4-diamine | 417.17 | 417.1 | (METHANOL-d4) δ = 9.23 (s, 2H), 7.51 (s, 1H), 7.46-7.44 (m, 1H), 7.36 (s, 1H), 7.25 (d, J = 8.0 Hz, 1H), 7.18 (d, J = 6.4 Hz, 1H), 3.47 (br s, 4H), 3.03 (br s, 4H) |
| 88 | 5-(4-(3-(6-(trifluoromethyl)pyridin-3-yl)phenyl)piperazin-1-yl)pyrimidine-2,4-diamine | 416.2 | 416.1 | (METHANOL-d₄) δ = 9.06 (s, 1H), 8.38 (br d, J = 8.0 Hz, 1H), 8.06 (s, 1H), 7.96 (d, J = 8.4 Hz, 1H), 7.86 (br d, J = 7.6 Hz, 1H), 7.77 (br d, J = 7.6 Hz, 2H), 7.70 (s, 1H), 3.92 (br s, 4H), 3.36 (br s, 4H) |

TABLE 6-continued

Compounds Prepared Using Synthetic Method B

| No. | IUPAC Name | LC/MS (M + 1) Expected MW | LC/MS (M + 1) Observed MW | $^1$H NMR (400 MHz) |
|---|---|---|---|---|
| 89 | 6-ethyl-5-(4-(3-(2-methylpyrimidin-5-yl)phenyl)piperazin-1-yl)pyrimidine-2,4-diamine | 391.2 | 391.1 | (METHANOL-d$_4$) δ = 8.96 (s, 2H), 7.45 (t, J = 7.6 Hz, 1H), 7.38-7.30 (m, 1H), 7.27-7.13 (m, 2H), 3.67 (br d, J = 12.0 Hz, 2H), 3.38-3.32 (m, 2H), 3.27-3.18 (m, 2H), 3.13-3.02 (m, 2H), 2.75 (s, 3H), 2.74-2.69 (m, 2H), 1.33 (t, J = 8.0 Hz, 3H) |
| 90 | 5-(4-(3-(2-fluoropyridin-4-yl)phenyl)piperazin-1-yl)pyrimidine-2,4-diamine | 366.1 | 366.1 | (METHANOL-d$_4$) δ = 8.23 (d, J = 5.6 Hz, 1H), 7.60 (d, J = 1.2 Hz, 1H), 7.52 (s, 1H), 7.47-7.39 (m, 1H), 7.37-7.33 (m, 2H), 7.25 (d, J = 7.6 Hz, 1H), 7.17 (dd, J = 2.0, 8.2 Hz, 1H), 3.54-3.35 (m, 4H), 3.07-3.00 (m, 4H) |
| 91 | 5-(4-(3-(5-fluoropyridin-3-yl)phenyl)piperazin-1-yl)pyrimidine-2,4-diamine | 366.1 | 366.1 | (METHANOL-d$_4$) δ = 8.72 (br s, 1H), 8.50 (br s, 1H), 7.99 (d, J = 9.5 Hz, 1H), 7.53 (s, 1H), 7.44 (t, J = 7.9 Hz, 1H), 7.35 (t, J = 1.9 Hz, 1H), 7.26-7.22 (m, 1H), 7.21-7.17 (m, 1H), 3.59-3.38 (m, 4H), 3.06 (br t, J = 4.6 Hz, 4H) |
| 92 | 5-(4-(3-chloro-5-(2-methylpyrimidin-5-yl)phenyl)piperazin-1-yl)pyrimidine-2,4-diamine | 397.16 | 397.1 | (MeOD-d$_4$) δ = 8.96 (s, 2H), 7.50 (s, 1H), 7.17 (d, J = 10.8 Hz, 2H), 7.09 (s, 1H), 3.46 (br s, 4H), 3.01 (br s, 4H), 2.75 (s, 3H). |
| 93 | 5-(4-(3-(5-methylpyridin-3-yl)phenyl)piperazin-1-yl)pyrimidine-2,4-diamine | 362.2 | 362.2 | (METHANOL-d$_4$) δ = 8.97 (br s, 1H), 8.74 (s, 1H), 8.67 (br s, 1H), 7.52 (s, 1H)1 7.47 (t, J = 8.0 Hz, 1H), 7.40 (s, 1H), 7.27 (d, J = 7.2 Hz, 1H), 7.21 (d, J = 1.6 Hz, 1H), 3.51-3.34 (m, 4H), 3.04 (br s, 4H), 2.64 (s, 3H) |
| 94 | 5-(4-(3-(2-methylpyrimidin-5-yl)phenyl)piperidin-1-yl)pyrimidine-2,4-diamine | 362.2 | 362.1 | (DMSO-d$_6$) δ = 9.02 (s, 2H), 7.68 (s, 1H), 7.61-7.56 (m, 2H), 7.46 (t, J = 8.0 Hz, 1H), 7.38 (d, J = 8.0 Hz, 1H), 6.06 (br s, 2H), 5.58 (s, 2H), 3.03-2.85 (m, 2H), 2.74-2.64 (m, 6H), 2.03-1.88 (m, 2H), 1.88-1.78 (m, 2H) |
| 95 | 5-(4-(3-(2-ethylpyrimidin-5-yl)phenyl)piperazin-1-yl)pyrimidine-2,4-diamine | 377.2 | 377.2 | (METHANOL-d$_4$) δ = 8.97 (s, 2H), 7.52 (s, 1H), 7.47-7.40 (m, 1H), 7.29 (s, 1H), 7.19 (d, J = 8.0 Hz, 1H), 7.14 (dd, J = 2.4, 10.4 Hz, 1H), 3.47 (br s, 4H), 3.07-2.98 (m, 6H), 1.39 (t, J = 7.6 Hz, 3H) |
| 96 | 5-(4-(3-(2-(dimethylamino)pyrimidin-5-yl)phenyl)piperazin-1-yl)pyrimidine-2,4-diamine | 392.22 | 392.1 | (METHANOL-d$_4$) δ = 8.66 (s, 2H), 7.50 (s, 1H), 7.39-7.35 (m, 1H), 7.22 (d, J = 2.0 Hz, 1H), 7.21-7.11 (m, 2H), 3.44 (br d, J = 4.0 Hz, 4H), 3.26 (s, 6H), 3.03 (br t, J = 4.4 Hz, 4H) |

TABLE 6-continued

Compounds Prepared Using Synthetic Method B

| No. | IUPAC Name | LC/MS (M + 1) Expected MW | LC/MS (M + 1) Observed MW | $^1$H NMR (400 MHz) |
|---|---|---|---|---|
| 97 | 5-(4-(3-(2-(methylamino)pyrimidin-5-yl)phenyl)piperazin-1-yl)pyrimidine-2,4-diamine | 378.21 | 378.2 | (METHANOL-$d_4$) δ = 8.77 - 8.54 (m, 2 H), 7.58-7.46 (m, 1 H), 7.42-7.27 (m, 1 H), 7.24-7.13 (m, 1 H), 7.12-7.01 (m, 2 H), 3.50-3.36 (m, 4 H), 3.07-2.97 (m, 7 H) |
| 98 | 5-(4-(3-(2-(azetidin-1-yl)pyrimidin-5-yl)phenyl)piperazin-1-yl)pyrimidine-2,4-diamine | 404.32 | 404.3 | (CDCl$_3$) δ = 8.65 (s, 2 H), 7.55-7.41 (m, 1 H), 7.38-7.27 (m, 1 H), 7.02-6.85 (m, 3 H), 6.37-6.20 (m, 1 H), 5.84-5.64 (m, 1 H), 4.42-4.30 (m, 4 H), 3.43-3.17 (m, 4 H), 2.96 (t, J = 4.4 Hz, 4 H), 2.61-2.35 (m, 2 H) |
| 99 | 5-(4-(3-cyclopropyl-5-methoxyphenyl)piperazin-1-yl)pyrimidine-2,4-diamine | 340.2 | 340.4 | (METHANOL-$d_4$) δ = 7.51 (s, 1H), 6.43 (d, J = 6.8 Hz, 2H), 6.27 (s, 1H), 3.76 (s, 3H), 3.38 (br s, 4H), 3.02 (br t, J = 4.8 Hz, 4H), 1.92-1.83 (m, 1H), 0.97-0.90 (m, 2H), 0.70-0.65 (m, 2H) |
| 100 | 5-(4-(3-(2-chloropyrimidin-5-yl)phenyl)piperazin-1-yl)pyrimidine-2,4-diamine | 383.1 | 383.1 | (METHANOL-$d_4$) δ = 8.95 (s, 2H), 7.50 (s, 1H), 7.45-7.39 (m, 1H), 7.28 (s, 1H), 7.19-7.11 (m, 2H), 3.45 (br s, 4H), 3.03 (br s, 4H) |

5-(4-(4-phenylthiazol-2-yl)piperazin-1-yl)pyrimidine-2,4-diamine was prepared by Suzuki coupling of 5-(4-(4-bromothiazol-2-yl)piperazin-1-yl)pyrimidine-2,4-diamine (prepared by Synthetic Method A) with phenylboronic acid according to synthetic Method B. The compounds listed in Table 7 were prepared analogously.

TABLE 7

Compounds Prepared Using Synthetic Method B

| No. | IUPAC Name | LC/MS (M + 1) Expected MW | LC/MS (M + 1) Observed MW | $^1$H NMR (400 MHz) |
|---|---|---|---|---|
| 101 | 5-(4-(4-phenylthiazol-2-yl)piperazin-1-yl)pyrimidine-2,4-diamine | 354.14 | 354 | (DMSO-$d_6$) δ = 12.00 (br s, 1H), 8.46 (s, 1H), 7.88-7.86 (m, 2H), 7.73 (s, 1H), 7.61 (s, 1H), 7.41(s, 2H), 7.39 (d, J = 8.0 Hz, 2H), 7.32-7.28 (m, 2H), 3.67 (br s, 4H), 2.90 (br s, 4H) |
| 118 | 5-(4-(3-cyclopropyl-5-fluorophenyl)piperazin-1-yl)pyrimidine-2,4-diamine | 329.1 | 328.4 | (METHANOL-$d_4$) δ = 7.48 (s, 1H), 6.56 (s, 1H), 6.51-6.47 (m, 1H), 6.24 (d, J = 10.0 Hz, 1H), 3.35 (s, 4H), 2.99-2.97 (m, 4H), 1.89-1.84 (m, 1H), 0.97-0.93 (m, 2H), 0.69-0.65 (m, 2H) |
| 119 | 5-(4-(3-(2-(methoxy-d3)pyrimidin-5-yl)phenyl)piperazin-1-yl)pyrimidine-2,4-diamine | 382.2 | 382.3 | (DMSO-$d_6$) δ = 8.92 (s, 2H), 7.60 (s, 1H), 7.47 (s, 2H), 7.35 (t, J = 16 Hz, 1H), 7.25 (s, 1H), 7.11 (d, J = 7.6 Hz, 1H), 7.02 (d, J = 8.2 Hz, 1H), 4.10 (s, 2H), 3.41 (s, 3H), 3.16 (s, 4H), 2.89 (s, 4H) |
| 120 | 5-(4-(3-bromo-5-(2-methoxypyrimidin-5-yl)phenyl)piperazin-1-yl)pyrimidine-2,4-diamine | 457.1 | 456.9 | (METHANOL-$d_4$) δ = 8.80 (s, 2H), 7.50 (s, 1H), 7.24 (s, 1H), 7.19 (t, J = 2.0 Hz, 1H), 7.16 (d, J = 1.6 Hz, 1H), 4.05 (s, |

TABLE 7-continued

Compounds Prepared Using Synthetic Method B

| No. | IUPAC Name | LC/MS (M + 1) Expected MW | LC/MS (M + 1) Observed MW | $^1$H NMR (400 MHz) |
|---|---|---|---|---|
| | | | | 3H), 3.49-3.45 (m, 4H), 3.00 (s, 4H) |
| 121 | 5-(4-(3-(2-ethoxypyrimidin-5-yl)phenyl)piperazin-1-yl)pyrimidine-2,4-diamine | 393.2 | 393.2 | (DMSO-d$_6$) δ = 8.91 (s, 2H), 7.60 (s, 1H), 7.36-7.30 (m, 1H), 7.25 (s, 1H), 7.10 (d, J = 8.0 Hz, 1H), 7.01 (d, J = 8.0 Hz, 1H), 6.10 (s, 2H), 5.63 (s, 2H), 4.42-4.37 (m, 2H), 3.37 (s, 4H), 2.89 (s, 4H), 1.36 (t, J = 7.0 Hz, 3H) |
| 122 | 5-(4-(3-(2-(2-methoxyethoxy)pyrimidin-5-yl)phenyl)piperazin-1-yl)pyrimidine-2,4-diamine | 423.2 | 423.4 | (METHANOL-d$_4$) δ = 8.80 (s, 2H), 7.51 (s, 1H), 7.39-7.37 (m, 1H), 7.22 (s, 1H), 7.10-7.09 (m, 2H), 4.59-4.56 (m, 2H), 3.81-3.77 (m, 2H), 3.42 (s, 7H), 3.03 (t, J = 4.6 Hz, 4H) |
| 123 | 5-(4-(3-(2-(oxetan-3-yloxy)pyrimidin-5-yl)phenyl)piperazin-1-yl)pyrimidine-2,4-diamine | 421.2 | 421.2 | (DMSO-d$_6$) δ = 8.93 (s, 2H), 7.60 (s, 1H), 7.36-7.31 (m, 1H), 7.26 (s, 1H), 7.10 (d, J = 8.0 Hz, 1H), 7.01 (d, J = 8.0 Hz, 1H), 6.11 (s, 2H), 5.63-5.59 (m, 3H), 4.92 (t, J = 6.8 Hz, 2H), 4.65-4.60 (m, 2H), 3.37 (s, 4H), 2.89 (s, 4H) |
| 124 | 5-(4-(3-(2-methoxy-4-methylpyrimidin-5-yl)phenyl)piperazin-1-yl)pyrimidine-2,4-diamine | 393.2 | 393.1 | (DMSO-d$_6$) δ = 8.39 (s, 1H), 7.59 (s, 1H), 7.32 (t, J = 8.0 Hz, 1H), 7.01 (d, J = 8.4 Hz, 1H), 6.95 (s, 1H), 6.80 (d, J = 7.6 Hz, 1H), 6.09 (s, 2H), 5.62 (s, 2H), 3.93 (s, 3H), 2.89-2.86 (m, 4H), 2.40 (s, 3H) |
| 125 | 5-(4-(3-(2,4-dimethoxypyrimidin-5-yl)phenyl)piperazin-1-yl)pyrimidine-2,4-diamine | 409.2 | 409.1 | (DMSO-d$_6$) δ = 8.36 (s, 1H), 7.59 (s, 1H), 7.28 (t, J = 7.8 Hz, 1H), 7.06 (s, 1H), 6.97 (d, J = 8.6 Hz, 1H), 6.93 (d, J = 7.6 Hz, 1H), 6.10 (s, 2H), 5.63 (s, 2H), 3.94 (s, 6H), 3.30 (s, 4H), 2.88 (s, 4H) |
| 126 | 5-(4-(3-(1-methyl-1H-imidazol-5-yl)phenyl)piperazin-1-yl)pyrimidine-2,4-diamine | 351.2 | 351.1 | (DMSO-d$_6$) δ = 7.67 (s, 1H), 7.59 (s, 1H), 7.30 (t, J = 8.0 Hz, 1H), 7.02 (d, J = 0.8 Hz, 1H), 6.99-6.96 (m, 2H), 6.88 (d, J = 7.2 Hz, 1H), 6.08 (s, 2H), 5.62 (s, 2H), 3.67 (s, 3H), 3.29 (s, 4H), 2.89-2.88 (m, 4H) |
| 127 | 5-(4-(3-(2-methoxy-5-methylthiazol-4-yl)phenyl)piperazin-1-yl)pyrimidine-2,4-diamine | 398.2 | 398.1 | (DMSO-d$_6$) δ = 7.59 (s, 1H), 7.28 (t, J = 8.0 Hz, 1H), 7.14 (s, 1H), 7.01 (d, J = 7.2 Hz, 1H), 6.96 (d, J = 9.2 Hz, 1H), 6.11 (s, 2H), 5.63 (s, 2H), 4.01 (s, 3H), 3.29 (s, 4H), 2.89 (s, 4H), 2.41 (s, 3H) |
| 128 | 5-(4-(3-(2-methoxy-1-methyl-1H-imidazol-5-yl)phenyl)piperazin-1-yl)pyrimidine-2,4-diamine | 381.2 | 381.2 | (METHANOL-d$_4$) δ = 7.62 (s, 1H), 7.32 (t, J = 7.8 Hz, 1H), 7.03-7.00 (m, 2H), 6.88 (d, J = 7.6 Hz, 1H), 6.62 (s, 1H), 4.03 (s, 3H), 3.42 (s, 3H), 3.35 (s, 4H), 3.01 (t, J = 4.8 Hz, 4H) |
| 129 | 5-(4-(3-(1-methyl-1H-tetrazol-5-yl)phenyl)piperazin-1-yl)pyrimidine-2,4-diamine | 353.2 | 353.4 | (DMSO-d$_6$) δ = 7.59 (s, 1H), 7.48-7.43 (m, 1H), 7.33 (s, 1H), 7.23 (d, J = 8.0 Hz, 1H), 7.19 (d, J = 7.6 Hz, 1H), 6.13 (s, 2H), 5.65 (s, 2H), 4.15 (s, 3H), 3.37 (s, 4H), 2.89 (t, J = 4.8 Hz, 4H) |
| 130 | (S)-5-(4-(3-(2-methoxypyrimidin-5-yl)phenyl)-3-methylpiperazin-1-yl)pyrimidine-2,4-diamine | 393.2 | 393.4 | (METHANOL-d$_4$) δ = 8.80 (s, 2H), 7.63 (s, 1H), 7.38 (t, J = 8.0 Hz, 1H), 7.19 (s, 1H), 7.08 (t, J = 7.6 Hz, 2H), 4.13 (s, 1H), 4.06 (s, 3H), 3.43-3.35 |

TABLE 7-continued

Compounds Prepared Using Synthetic Method B

| No. | IUPAC Name | LC/MS (M + 1) Expected MW | LC/MS (M + 1) Observed MW | ¹H NMR (400 MHz) |
|---|---|---|---|---|
| | | | | (m, 2H), 3.15-3.09 (m, 2H), 2.88-2.86 (m, 2H), 1.20 (d, J = 9.8 Hz, 3H) |
| 131 | 5-(4-(3-(2-cyclopropoxypyrimidin-5-yl)phenyl)piperazin-1-yl)pyrimidine-2,4-diamine | 405.2 | 405.4 | (DMSO-$d_6$) δ = 8.93 (s, 2H), 7.60 (s, 1H), 7.36-7.32 (m, 1H), 7.26 (s, 1H), 7.10 (d, J = 7.6 Hz, 1H), 7.01 (d, J = 8.0 Hz, 1H), 6.11 (s, 2H), 5.63-5.62 (m, 2H), 4.35-4.32 (m, 1H), 3.37 (s, 4H), 2.89 (s, 4H), 0.83-0.79 (m, 2H), 0.78-0.73 (m, 2H) |
| 132 | 5-(4-(3-(4-cyclopropyl-2-methoxythiazol-5-yl)phenyl)piperazin-1-yl)pyrimidine-2,4-diamine | 424.5 | 424.2 | (DMSO-$d_6$) δ = 8.44 (s, 1H), 7.64 (s, 1H), 7.56 (s, 1H), 7.44 (s, 1H), 7.30 (t, J = 84 Hz, 1H), 6.99-6.97 (m, 2H), 6.91 (d, J = 8.0 Hz, 1H), 3.96 (s, 3H), 3.36 (s, 4H), 2.89 (s, 4H), 2.03-1.98 (m, 1H), 0.88 (s, 2H), 0.86 (s, 2H) |
| 133 | (R)-5-(4-(3-(2-methoxypyrimidin-5-yl)phenyl)-3-methylpiperazin-1-yl)pyrimidine-2,4-diamine | 393.4 | 393.2 | (DMSO-$d_6$) δ = 8.92 (s, 2H), 8.48 (s, 1H), 7.60-7.55 (m, 4H), 7.36 (t, J = 7.6 Hz, 1H), 7.23 (s, 1H), 7.12 (s, 1H), 7.00 (d, J = 4.8 Hz, 1H), 4.25 (s, 1H), 3.96 (s, 3H), 3.52-3.35 (m, 2H), 3.10 (t, J = 11.4 Hz, 2H), 2.81 (d, J = 10.8 Hz, 1H), 2.57-2.53 (m, 1H), 1.15 (d, J = 6.4 Hz, 3H) |
| 134 | 5-(4-(4-(pyrimidin-5-yl)phenyl)piperazin-1-yl)pyrimidine-2,4-diamine | 349.1 | 349.1 | (DMSO-$d_6$) δ = 9.09 (s, 3H), 7.71 (d, J = 8.4 Hz, 2H), 7.60 (s, 1H), 7.11 (d, J = 8.8 Hz, 2H), 6.12 (s, 2H), 5.63 (s, 2H), 3.38 (s, 4H), 2.90 (s, 4H) |
| 135 | 5-(4-(4-(2-methoxypyrimidin-5-yl)phenyl)piperazin-1-yl)pyrimidine-2,4-diamine | 379.2 | 379.2 | (DMSO-$d_6$) δ = 8.87 (s, 2H), 7.61 (d, J = 5.2 Hz, 3H), 7.08 (d, J = 8.0 Hz, 2H), 6.10 (s, 2H), 5.62 (s, 2H), 3.95 (s, 3H), 3.35 (s, 4H), 2.90 (s, 4H) |
| 136 | 5-(4-(4-(2-methylpyrimidin-5-yl)phenyl)piperazin-1-yl)pyrimidine-2,4-diamine | 362.2 | 362.2 | (DMSO-$d_6$) δ = 8.95 (s, 2H), 7.65 (d, J = 8.8 Hz, 2H), 7.59 (s, 1H), 7.09 (d, J = 8.8 Hz, 2H), 6.14 (s, 2H), 5.65 (s, 2H), 3.36 (s, 4H), 2.90-2.89 (m, 4H), 2.63 (s, 3H) |

Example 4: Synthetic Method C

Synthetic Method C is Exemplified in the Synthesis of 5-(4-(3,5-dimethylphenyl)piperazin-1-yl)pyrimidine-2,4-diamine (Compound 109)

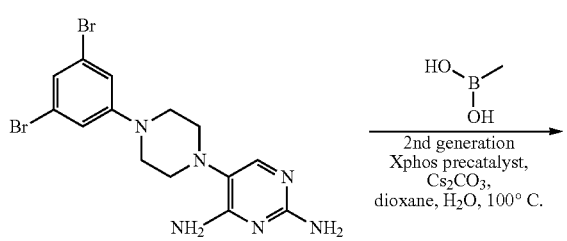

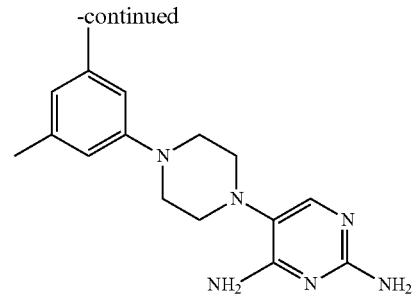

To a solution of 5-(4-(3,5-dibromophenyl)piperazin-1-yl)pyrimidine-2,4-diamine (50.0 mg, 116.7 μmol, 1.0 eq), prepared according to synthetic Method A, and methylboronic acid (13.9 mg, 233.5 μmol, 2.0 eq) in dioxane (2.0 mL) and H₂O (0.5 mL) was added Cs₂CO₃ (114.1 mg, 350.3 μmol, 3.0 eq) and the 2nd GENERATION XPHOS PRE-CATALYST (1.8 mg, 2.3 μmol, 0.02 eq). The mixture was stirred at 100° C. for 12 hours. The mixture was concentrated and the residue was purified by prep-HPLC (TFA condition) to give 5-(4-(3,5-dimethylphenyl)piperazin-1-yl)pyrimidine-2,4-diamine (4.4 mg, 14.7 umol, 12.6% yield) as white solid.

Example 5: Synthetic Method D

Synthetic Method D is Exemplified Below for the Synthesis of 5-(4-(3-(tetrahydro-2H-pyran-4-yl)phenyl)piperazin-1-yl)pyrimidine-2,4-diamine (Compound 110)

Step 1. 5-(4-(3-(3,6-dihydro-2H-pyran-4-yl)phenyl)piperazin-1-yl)pyrimidine-2,4-diamine

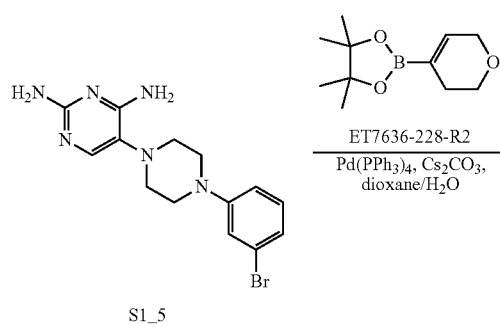

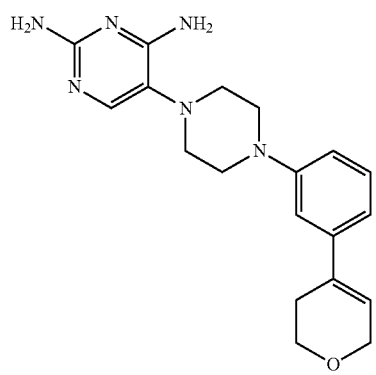

Cpd 31A

To a mixture of 5-(4-(3-bromophenyl)piperazin-1-yl)pyrimidine-2,4-diamine (50.0 mg, 143.1 μmol, 1.0 eq) and 1-(3,6-dihydro-2H-pyran-4-yl)-3,3,4,4-tetramethylborolane (60.1 mg, 286.3 μmol, 2.0 eq) in 1,4-dioxane (4.0 mL) and H$_2$O (1.0 mL) was added Cs$_2$CO$_3$ (69.9 mg, 214.7 μmol, 1.5 eq) and Pd(PPh$_3$)$_4$ (8.2 mg, 7.1 μmol, 0.05 eq) in one portion at 20° C. under N$_2$. The mixture was stirred at 100° C. for 12 hours. The reaction mixture was filtered and concentrated under reduced pressure to give a residue. The residue was purified by prep-HPLC (TFA condition) to give 5-(4-(3-(3,6-dihydro-2H-pyran-4-yl)phenyl)piperazin-1-yl)pyrimidine-2,4-diamine (30.0 mg, 85.1 μmol, 59.4% yield) as a white solid. $^1$H NMR (400 MHz, METHANOL-d$_4$) δ=7.53 (s, 1H), 7.32-7.28 (m, 1H), 7.17 (s, 1H), 7.10-7.04 (m, 2H), 6.19 (s, 1H), 4.30 (d, J=2.4 Hz, 2H), 3.94-3.91 (m, 2H), 3.45-3.31 (m, 4H), 3.08-3.06 (m, 4H), 2.53-2.52 (m, 2H).

Step 2. 5-(4-(3-(Tetrahydro-2H-pyran-4-yl)phenyl)piperazin-1-yl)pyrimidine-2,4-diamine

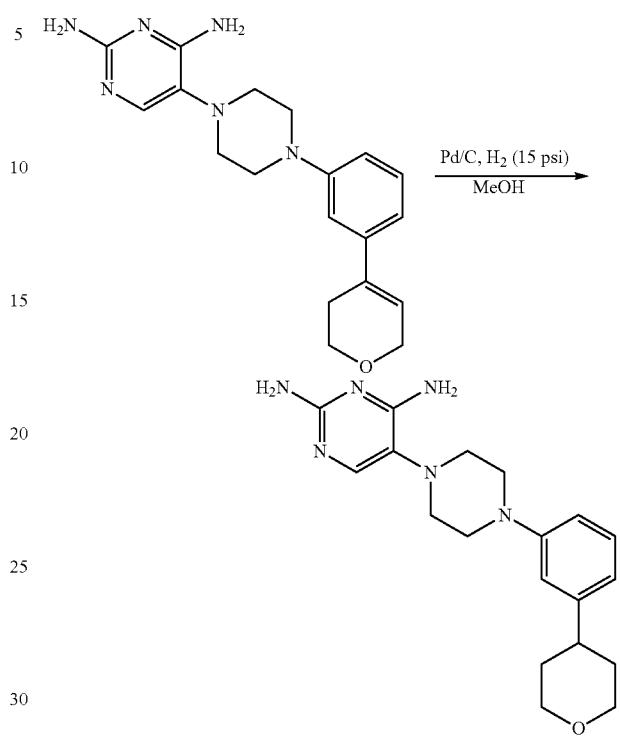

To a solution of 5-(4-(3-(3,6-dihydro-2H-pyran-4-yl)phenyl)piperazin-1-yl)pyrimidine-2,4-diamine (30.0 mg, 85.1 μmol, 1.0 eq) in CH$_3$OH (10.0 mL) was added Pd/C (10 mg) under Ar atmosphere. The suspension was degassed and purged with H$_2$ 3 times. The mixture was stirred under H$_2$ (15 Psi) at 15° C. for 1 hour, filtered on celite and the filtrate was concentrated under reduced pressure to give 5-(4-(3-(Tetrahydro-2H-pyran-4-yl)phenyl)piperazin-1-yl)pyrimidine-2,4-diamine (19.0 mg, 51.2 μmol, 30.0% yield, 95.53% purity) as a white solid. LCMS (ESI+): m/z 355.1 (M+1)$^+$, Rt: 2.147 Min. $^1$H NMR (400 MHz, METHANOL-d$_4$) δ=7.52 (s, 1H), 7.25 (br t, J=7.5 Hz, 1H), 7.02-6.92 (m, 2H), 6.88 (brd, J=7.1 Hz, 1H), 4.04 (brd, J=10.6 Hz, 2H), 3.56 (br t, J=11.0 Hz, 2H), 3.40 (br s, 4H), 3.04 (br s, 4H), 2.78 (br s, 1H), 1.88-1.71 (m, 4H).

Example 6: Synthetic Method E

Synthetic Method E is Exemplified Below for the Synthesis of 5-(4-(3-(pyrimidin-4-yl)phenyl)piperazin-1-yl)pyrimidine-2,4-diamine (Compound 102)

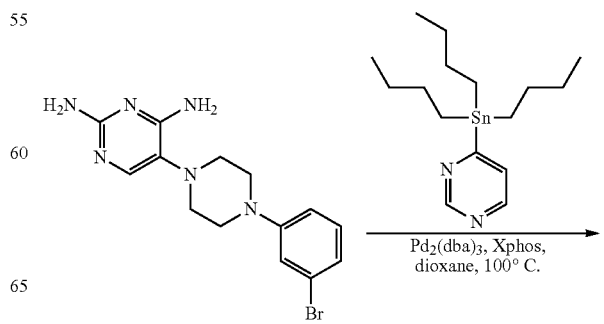

73
-continued

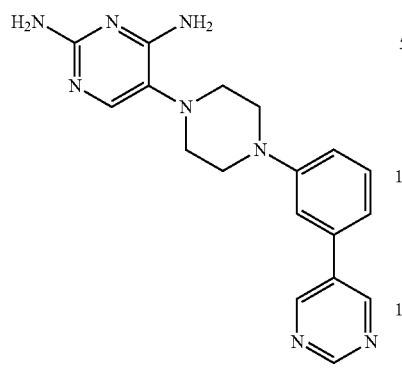

A mixture of 5-(4-(3-bromophenyl)piperazin-1-yl)pyrimidine-2,4-diamine (100.0 mg, 286.3 μmol, 1.0 eq), tributyl(pyrimidin-4-yl)stannane (105.7 mg, 286.3 umol, 1 eq), Pd$_2$(dba)$_3$ (7.8 mg, 8.6 μmol, 0.03 eq). XPhos (23.2 mg, 48.6 umol, 0.17 eq) in dioxane (8.0 mL) and was degassed and purged with N$_2$ for 3 times, and then the mixture was stirred at 100° C. for 12 hours under N$_2$ atmosphere. The mixture was concentrated under reduced pressure and the residue was purified by prep-HPLC (TFA condition) to give 5-(4-(3-(pyrimidin-4-yl)phenyl)piperazin-1-yl)pyrimidine-2,4-diamine (4.5 mg, 12.9 μmol, 4.51% yield) as a yellow solid. Compounds prepared by method E are listed in Table 8.

74

Example 7: Synthetic Method F

Synthetic Method F is Exemplified Below for the Synthesis of 5-(3-(4-(2,4-diaminopyrimidin-5-yl)piperazin-1-yl)phenyl)pyrimidin-2-ol (Compound 111)

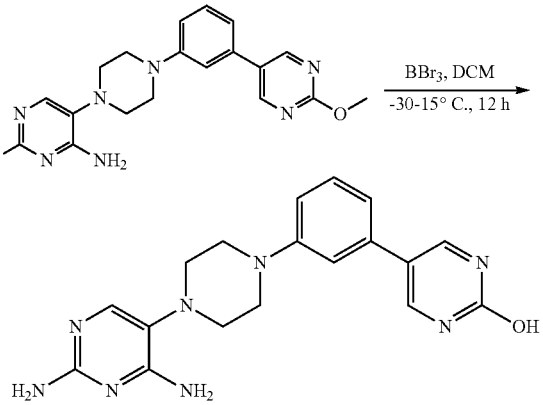

To a solution of 5-(4-(3-(2-methoxypyrimidin-5-yl)phenyl)piperazin-1-yl)pyrimidine-2,4-diamine (500.0 mg, 1.3 mmol, 1.0 eq) in dichloromethane (5.0 mL) was added BBr$_3$ (3.3 g, 13.2 mmol, 1.2 mL, 10.0 eq) at −30° C. The mixture was warmed to 15° C. and stirred at 15° C. for 12 hours. The mixture was quenched with CH$_3$OH (10 mL), concentrated under reduced pressure and the residue was purified by prep-HPLC (neutral condition) to afford 5-(3-(4-(2,4-di-

TABLE 8

Compounds Prepared Using Synthetic Method E

| Compd # | IUPAC Name | LC/MS (M + 1) Expected MW | LC/MS (M + 1) Observed MW | $^1$H NMR (400 MHz) |
|---|---|---|---|---|
| 102 | 5-(4-(3-(pyrimidin-4-yl)phenyl)piperazin-1-yl)pyrimidine-2,4-diamine | 349.2 | 349.1 | (METHANOL-d$_4$) δ = 9.17 (s, 1H), 8.78 (d, J = 6.0 Hz, 1H), 7.99 (dd, J = 1.2, 5.6 Hz, 1H), 7.84 (t, J = 2.0 Hz, 1H), 7.62 (dd, J = 0.8, 7.6 Hz, 1H), 7.51 (s, 1H), 7.44 (t, J = 8.0 Hz, 1H), 7.23 (dd, J = 2.2, 7.6 Hz, 1H), 3.57-3.32 (m, 4H), 3.04 (br t, J = 9.2 Hz, 4H) |
| 103 | 5-(4-(3-(pyrimidin-2-yl)phenyl)piperazin-1-yl)pyrimidine-2,4-diamine | 349.2 | 349.2 | (METHANOL-d$_4$) δ = 8.85 (br s, 2H), 8.07 (br s, 1H), 7.92 (br d, J = 6.6 Hz, 1H), 7.52 (br s, 1H), 7.40 (br d, J = 13.7 Hz, 2H), 7.21 (br s, 1H), 3.46 (br s, 4H), 3.05 (br s, 4H) |
| 104 | 5-(4-(3-(pyrazin-2-yl)phenyl)piperazin-1-yl)pyrimidine-2,4-diamine | 349.2 | 349.2 | (METHANOL-d$_4$) δ = 9.19 (s, 1H), 8.73 (s, 1H), 8.60 (br d, J = 2.0 Hz, 1H), 8.30 (s, 1H), 8.11 (br d, J = 7.6 Hz, 1H), 7.73-7.65 (m, 2H), 7.62 (s, 1H), 3.85 (br s, 4H), 3.30-3.26 (m, 4H) |
| 105 | 5-(4-(3-(pyridin-2-yl)phenyl)piperazin-1-yl)pyrimidine-2,4-diamine | 348.2 | 348.1 | (METHANOL-d$_4$) δ = 8.60 (br d, J = 4.9 Hz, 1H), 7.94-7.88 (m, 1H), 7.87-7.82 (m, 1H), 7.63 (s, 1H), 7.58 (s, 1H), 7.42-7.34 (m, 3H), 7.12 (br s, 1H), 3.39 (br d, J = 11.0 Hz, 4H), 3.03 (br t, J = 4.6 Hz, 4H) | aminopyrimidin-5-yl)piperazin-1-yl)phenyl)pyrimidin-2-ol (60.0 mg, 154.3 μmol, 11.6% yield, 93.72% purity) as a yellow solid. LCMS (ESI+): m/z 365.2 (M+1)+, Rt: 1.906 Min. $^1$H NMR (DMSO-d$_6$ 400 MHz) δ=8.60 (br s, 2H), 7.58 (d, J=0.8 Hz, 1H), 7.31-7.23 (m, 1H), 7.13 (s, 1H), 7.03-6.89 (m, 2H), 3.33 (br s, 4H), 2.87 (br t, J=4.6 Hz, 4H).

Example 8: Synthetic Method G

According to Synthetic Method G, compounds of the present invention can be prepared as described below. Halogenation of an appropriately substituted malonate, e.g., 1013, such as with sulfuryl chloride provides the 2-chloromalonate 1014, which can undergo reaction with an appropriately substituted piperazine to give the 2-piperazinyl malonate intermediate 1015. Reaction with guanidine in a polar protic solvent such as ethanol or methanol gives the 2-amino-4-hydroxypyrimidine 1016. Chlorination followed by reaction with ammonia gives the target 2,4-diaminopyrimidines 1018.

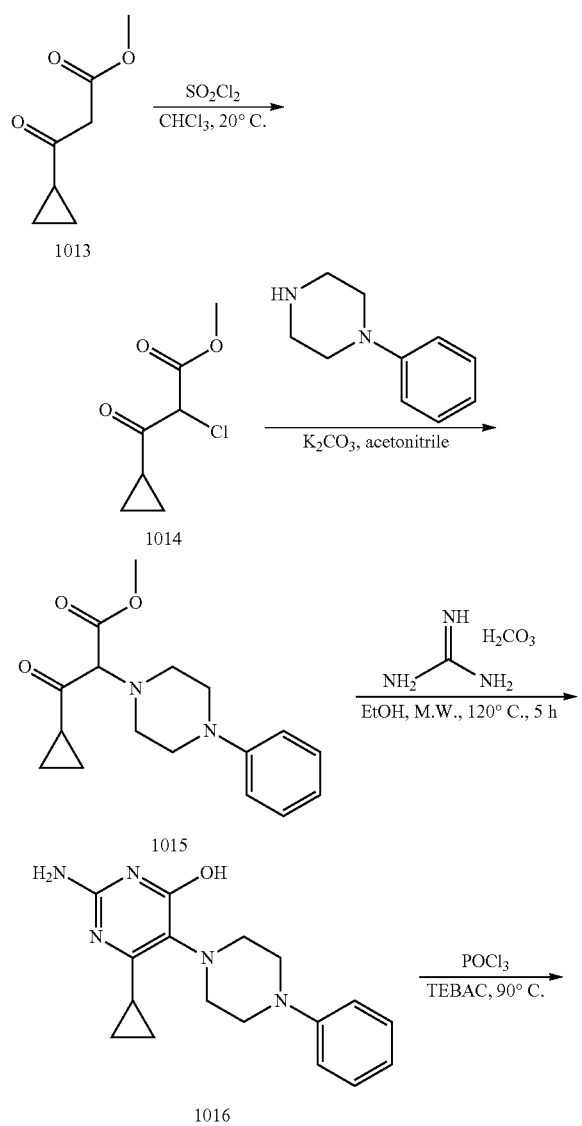

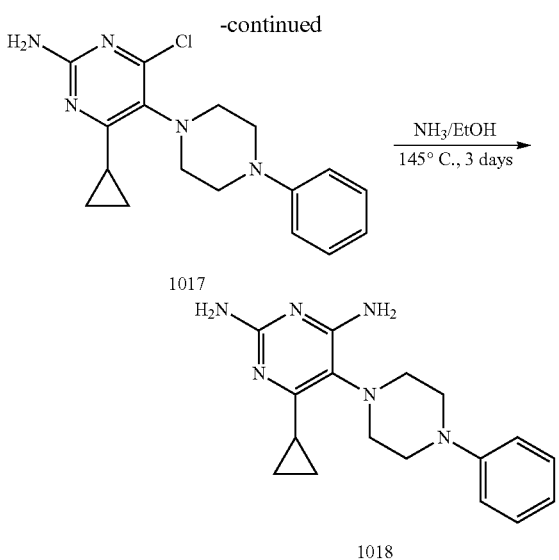

Synthetic Method G is Exemplified Below for the Preparation of 6-cyclopropyl-5-(4-phenylpiperazin-1-yl)pyrimidine-2,4-diamine (Compound 112)

Step 1. Methyl 2-chloro-3-cyclopropyl-3oxopropanoate

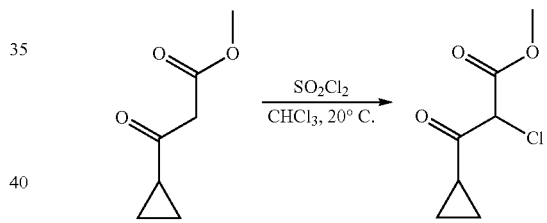

A mixture of methyl 3-cyclopropyl-3-oxo-propanoate (5.00 g, 35.17 mmol, 1.00 eq), sulfuryl chloride (5.70 g, 42.20 mmol, 4.22 mL, 1.20 eq) in CHCl$_3$ (50.00 mL) was degassed and purged with N$_2$ for 3 times, and then the mixture was stirred at 20° C. for 2 hours under N$_2$ atmosphere. Removal of the solvent gave the methyl 2-chloro-3-cyclopropyl-3-oxo-propanoate (5.00 g, crude) as a yellow oil which was used to next step without further purification.

Step 2. Methyl 3-cyclopropyl-3-oxo-2-(4-phenylpiperazin-1-yl)propanoate

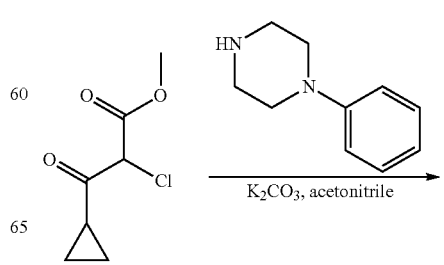

-continued

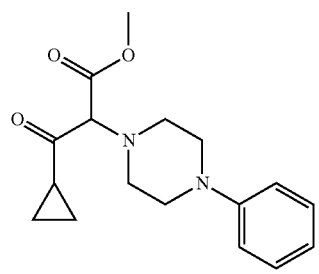

To a solution of methyl 2-chloro-3-cyclopropyl-3-oxo-propanoate (2.50 g, 14.16 mmol, 1.00 eq) and 1-phenylpiperazine (2.30 g, 14.16 mmol, 2.17 mL, 1.00 eq) in MeCN (60.00 mL) was added K₂CO₃ (2.94 g, 21.24 mmol, 1.50 eq) at 25° C. and the mixture was stirred for 5 h. The reaction was poured into water (150 mL) and extracted with ethyl acetate (3×50 mL). The combined organic layers were dried over Na₂SO₄, filtered and concentrated in vacuo. The residue was purified by column chromatography (SiO₂, Petroleum ether/Ethyl acetate=100/1 to 20:1) to give methyl 3-cyclopropyl-3-oxo-2-(4-phenylpiperazin-1-yl)propanoate (1.70 g, 5.62 mmol, 39.71% yield) as a white solid.

Step 3. 2-Amino-6-cyclopropyl-5-(4-phenylpiperazin-1-yl)pyrimidin-4-ol

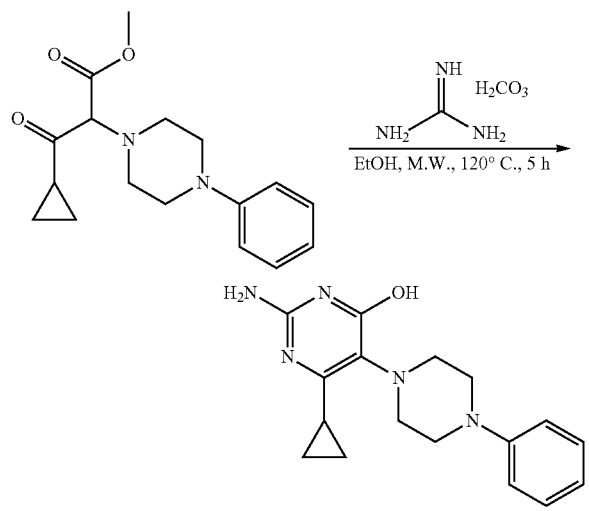

Methyl 3-cyclopropyl-3-oxo-2-(4-phenylpiperazin-1-yl)propanoate (100.00 mg, 330.72 µmol, 1.00 eq), EtOH (3.00 mL) and carbonic acid:guanidine (40.05 mg, 330.72 µmol, 1.00 eq) were combined in a microwave vial. The vial was sealed and allowed to react at 120° C. with stirring for 5 hours. This was repeated 6 times and the batches were combined and solvent was removed under reduced pressure. Water (25 ml) was added and the mixture was brought to pH 5 via careful addition of acetic acid. The precipitate was isolated via filtration to afford a yellow solid. The solid was purified by Prep-HPLC (TFA condition) to give 2-amino-6-cyclopropyl-5-(4-phenylpiperazin-1-yl)pyrimidin-4-ol (300 mg, 963 µmol, 48.6% yield) as a yellow solid.

Step 4. 4-Chloro-6-cyclopropyl-5-(4-phenylpiperazin-1-yl)pyrimidin-2-amine

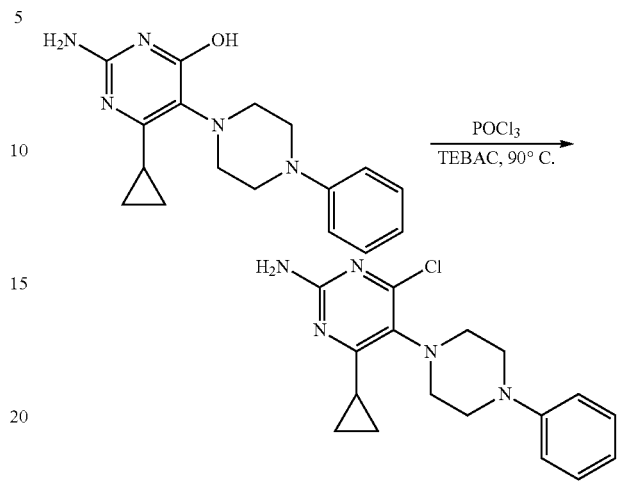

To a mixture of 2-amino-6-cyclopropyl-5-(4-phenylpiperazin-1-yl)pyrimidin-4-ol (150 mg, 482 µmol, 1.00 eq), TEBAC (53.7 mg, 289 µmol, 50.2 uL, 0.60 eq) and PhNMe₂ (58.4 mg, 481.7 µmol, 60.8 µL, 1.00 eq) in MeCN (10.0 mL) was added POCl₃ (739 mg, 4.82 mmol, 448 µL, 10.00 eq) under N₂ atmosphere. The mixture was stirred at 90° C. for 1 hour, quenched by addition aqueous NaHCO₃ (50 mL) and extracted with dichloromethane (3×20 mL). The combined organic layers were dried over anhydrous Na₂SO₄, filtered and concentrated under reduced pressure to give a residue. The residue was purified by silica gel chromatography to provide 4-chloro-6-cyclopropyl-5-(4-phenylpiperazin-1-yl)pyrimidin-2-amine (60.0 mg, 182 µmol, 37.8% yield) was obtained as a yellow solid. LCMS (ESI+): m/z 330 (M+1)⁺, Rt: 0.972 Min.

Step 5. 6-Cyclopropyl-5-(4-phenylpiperazin-1-yl)pyrimidine-2,4-diamine

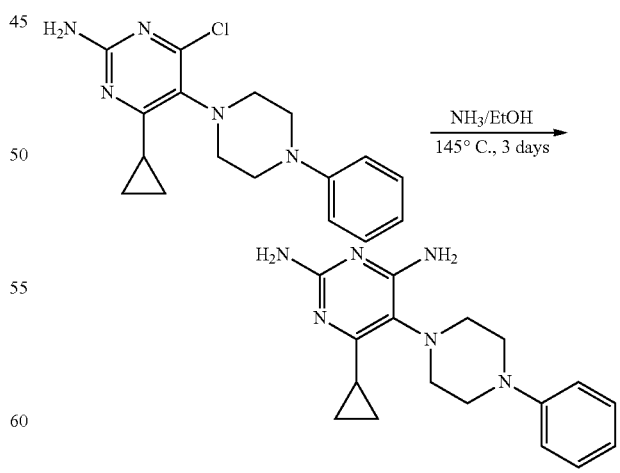

To a mixture of NH₃ (155 mg, 9.10 mmol, 50.0 eq) in ethanol (5.0 mL) was added 4-chloro-6-cyclopropyl-5-(4-phenylpiperazin-1-yl)pyrimidin-2-amine (60.0 mg, 181.9 µmol, 1.00 eq) under N₂ atmosphere. The mixture was stirred at 145° C. for 3 days in a steel bomb, cooled to 25° C. and concentrated under reduced pressure. The solids were collected by filtration, washed with EtOAc (200 mL) and purified by prep-HPLC to give 6-cyclopropyl-5-(4-phenylpiperazin-1-yl)pyrimidine-2,4-diamine (3.0 mg, 6.44 umol, 9.03% yield) as a white solid. LCMS (ESI+): m/z 311.2 (M+1)⁺, Rt: 2.146 Min. ¹H NMR (400 MHz, METHANOL-d4): δ=7.44-7.37 (m, 2H), 7.33-7.25 (m, 2H), 7.18-7.08 (m, 1H), 3.64 (br d, J=10.4 Hz, 4H), 3.50-3.34 (m, 2H), 3.30-3.09 (m, 2H), 2.34-2.21 (m, 1H), 1.32-1.25 (m, 2H), 1.14-1.08 (m, 2H).

6-(Cyclopropylmethyl)-5-(4-phenylpiperazin-1-yl)pyrimidine was prepared in a similar manner as described in synthetic method G, but starting with methyl 3-cyclopropylmethyl-3-oxo-propanoate. Other compounds prepared analogously, by method G, are listed in Table 9.

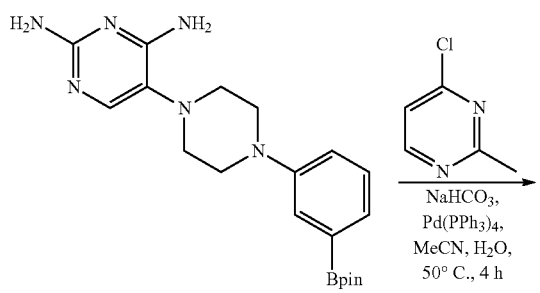

TABLE 9

Compounds Prepared Using Synthetic Method G

| Compd # | IUPAC Name | LC/MS (M + 1) Expected MW | LC/MS (M + 1) Observed MW | ¹H NMR (400 MHz) |
|---|---|---|---|---|
| 106 | 6-(cyclopropylmethyl)-5-(4-phenylpiperazin-1-yl)pyrimidine-2,4-diamine | 325.21 | 325.2 | (METHANOL-d₄) δ = 7.31 (t, J = 7.2 Hz, 2H), 7.11 (br d, J = 8.0 Hz, 2H), 6.97 (br s, 1H), 7.01-6.94 (m, 1H), 3.51-3.49 (m, 2H), 3.27-3.23 (m, 4H), 3.12-3.09 (m, 2H), 2.66-2.65 (m, 2H), 1.06 (m, 1H), 0.70-0.65 (m, 2H), 0.42-0.38 (m, 2H) |
| 137 | 5-(4-phenylpiperazin-1-yl)-6-(3,3,3-trifluoropropyl)pyrimidine-2,4-diamine | 367.2 | 367.2 | (METHANOL-d₄) δ = 7.33 (t, J = 7.8 Hz, 2H), 7.14 (d, J = 8.0 Hz, 2H), 7.00 (t, J = 7.2 Hz, 1H), 3.46-3.43 (m, 2H), 3.34-3.31 (m, 2H), 3.27-3.22 (m, 4H), 2.99-2.95 (m, 2H), 2.66-2.59 (m, 2 H) |
| 138 | 5-(4-(5-fluoropyridin-2-yl)piperazin-1-yl)-6-(3,3,3-trifluoropropyl)pyrimidine-2,4-diamine | 386.4 | 386.2 | (METHANOL-d₄) δ = 8.03 (d, J = 2.8 Hz, 1H), 7.58-7.53 (m, 1H), 7.03-7.00 (m, 1H), 3.82 (d, J = 12.4 Hz, 2H), 3.54-3.51 (m, 2H), 3.16-3.10 (m, 4H), 2.95-2.91 (m, 2H), 2.63-2.59 (m, 2 H) |

Example 9: Synthetic Method H

Synthetic Method H is Exemplified Below for the Preparation of 5-(4-(3-(2-methylpyrimidin-4-yl)phenyl)piperazin-1-yl)pyrimidine-2,4-diamine (Compound 113)

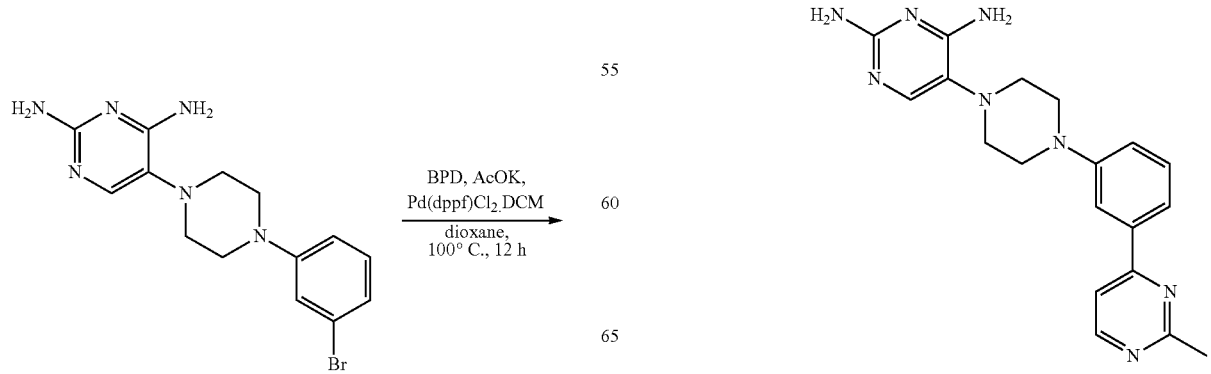

Step 1. 5-(4-(3-(4,4,5,5-tetramethyl-1,3,2-dioxaborolan-2-yl)phenyl)piperazin-1-yl)pyrimidine-2,4-diamine

Step 2. 5-(4-(3-(2-methylpyrimidin-4-yl)phenyl)piperazin-1-yl)pyrimidine-2,4-diamine

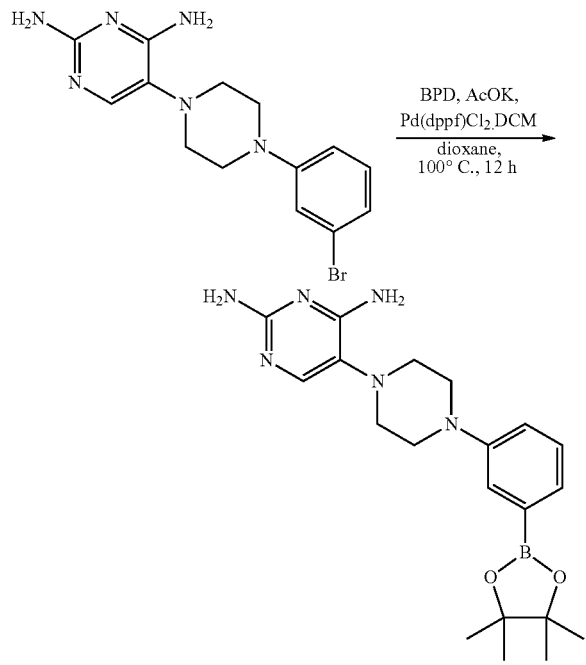

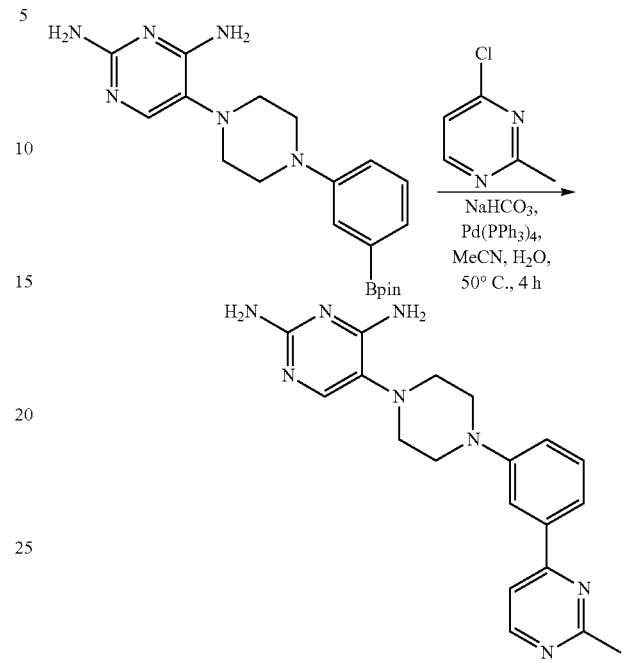

A mixture of 5-(4-(3-bromophenyl)piperazin-1-yl)pyrimidine-2,4-diamine (1.0 g, 2.8 mmol, 1.0 eq), bis(pinacolato)diboron (1.1 g, 4.2 mmol, 1.5 eq), AcOK (842.0 mg, 8.5 mmol, 3.0 eq), Pd(dppf)Cl$_2$·CH$_2$Cl$_2$ (467.1 mg, 572.0 umol, 0.2 eq) in dioxane (20.0 mL) was degassed and purged with N$_2$ for 3 times, and then the mixture was stirred at 100° C. for 12 hours under N$_2$ atmosphere. The mixture was concentrated under reduced pressure to give 5-(4-(3-(4,4,5,5-tetramethyl-1,3,2-dioxaborolan-2-yl)phenyl)piperazin-1-yl)pyrimidine-2,4-diamine (800.0 mg, 1.2 mmol, 44.4% yield) as a black brown oil which was used to next step without further purification. LCMS (ESI+): m/z 397.1 (M+1)$^+$, Rt: 1.271 Min.

A mixture of 5-(4-(3-(4,4,5,5-tetramethyl-1,3,2-dioxaborolan-2-yl)phenyl)piperazin-1-yl)pyrimidine-2,4-diamine (200.0 mg, 504.6 μmol, 1.0 eq), 4-chloro-2-methyl-pyrimidine (64.8 mg, 504.6 μmol, 1.0 eq), NaHCO$_3$ (127.1 mg, 1.5 mmol, 3.0 eq), Pd(PPh$_3$)$_4$ (116.6 mg, 100.9 μmol, 0.2 eq) in H$_2$O (1.0 mL) and CH$_3$CN (3.0 mL) was degassed and purged with N$_2$ 3 times, and then the mixture was stirred at 50° C. for 4 hours under N$_2$ atmosphere. The mixture was concentrated under reduced pressure to give a residue. The residue was purified by prep-HPLC (TFA condition) to give 5-(4-(3-(2-methylpyrimidin-4-yl)phenyl)piperazin-1-yl)pyrimidine-2,4-diamine (20.9 mg, 55.3 μmol, 10.9% yield, 95.9% purity) as a black brown solid. LCMS (ESI+): m/z 363.1 (M+1)$^+$, Rt: 2.142 Min. $^1$H NMR (MeOD 400 MHz) δ=8.73 (d, J=5.7 Hz, 1H), 7.90 (d, J=5.5 Hz, 1H), 7.87 (s, 1H), 7.66 (d, J=7.7 Hz, 1H), 7.52 (s, 1H), 7.46 (t, J=7.9 Hz, 1H), 7.26 (dd, J=2.2, 8.2 Hz, 1H), 3.48 (br s, 4H), 3.05 (br t, J=4.6 Hz, 4H), 2.79 (s, 3H).

TABLE 10

Compounds Prepared Using Synthetic Method H

| Compd # | IUPAC Name | LC/MS (M + 1) Expected MW | LC/MS (M + 1) Observed MW | $^1$H NMR (400 MHz) |
|---|---|---|---|---|
| 107 | 5-(4-(3-(pyridazin-3-yl)phenyl)piperazin-1-yl)pyrimidine-2,4-diamine | 349.1 | 349.1 | (METHANOL-d$_4$) δ = 9.19 (dd, J = 1.6, 5.2 Hz, 1H), 8.25 (dd, J = 1.6, 8.4 Hz, 1H), 7.86 (dd, J = 5.2, 8.8 Hz, 1H), 7.77 (s, 1H), 7.54-7.50 (m, 2H), 7.49-7.45 (m, 1H), 7.25-7.21 (m, 1H), 3.48 (br s, 4H), 3.05 (br t, J = 4.4 Hz, 4H) |

TABLE 10-continued

Compounds Prepared Using Synthetic Method H

| Compd # | IUPAC Name | LC/MS (M + 1) Expected MW | LC/MS (M + 1) Observed MW | $^1$H NMR (400 MHz) |
|---|---|---|---|---|
| 108 | 5-(4-(3-(6-methylpyridazin-3-yl)phenyl)piperazin-1-yl)pyrimidine-2,4-diamine | 363.2 | 363.1 | (METHANOL-d$_4$) δ = 8.26 (d, J = 8.8 Hz, 1H), 7.87 (d, J = 8.8 Hz, 1H), 7.74 (s, 1H), 7.53-7.43 (m, 3H), 7.22 (dd, J = 1.2, 8.0 Hz, 1H), 3.48 (br s, 4H), 3.04 (br t, J = 4.4 Hz, 4H), 2.78 (s, 3H) |

Example 10

Certain of the compounds prepared as described above were assayed to determine their IC$_{50}$ for inhibition of hDHFR, *T. gondii* DHFR (tgDHFR), *T. cruzi* DHFR (tcDHFR), *T. brucei* DHFR (tbDHFR), *L. major* DHFR (lmDHFR), and *P. falciparum* DHFR (pfDHFR). At least three independent replicates of the assay were conducted for each compound tested. In the assay, DHFR-catalyzed conversion of dihydrofolic acid+NADPH to tetrahydrofolic acid+NADP$^+$ was conducted in the presence of various concentrations of the compound being assayed. After an incubation period of 60 minutes, diaphorase and resazurin were added. That mixture was incubated for 10 minutes, during which time diaphorase catalyzed the reduction of resazurin to resorufin using NADPH that had not been consumed in the first, DHFR-catalyzed reaction. The fluorescence of resorufin indicated the amount of unreacted NADPH. Compounds were tested at various concentrations to determine their IC$_{50}$, pIC$_{50}$ (−log$_{10}$IC$_{50}$), and selectivity for the parasite DHFR (hDHFR IC$_{50}$/parasite DHFR IC$_{50}$). The results are presented in Tables 11-15 below. The DHFR sequences in protozoans of genus *Leishmania, Typanosoma*, and *Plasmodium* are highly conserved relative to *T. gondii*. Compounds described herein that are selective for tgDHFR are expected to be selective for DHFR derived from those genuses as well.

TABLE 11

Potency and Selectivity against *T. gondii* DHFR

| No. | Compound Name | hDHFR pIC50 - DHFR primary assay | tgDHFR pIC50 - DHFR primary assay | Average DHFR selectivity (h/tg) |
|---|---|---|---|---|
| — | Methotrexate: (4-(((2,4-diaminopteridin-6-yl)methyl)(methyl)amino)benzoyl)-L-glutamic acid | 8.37 | 7.11 | 0.06 |
| — | Pyrimethamine: 5-(4-chlorophenyl)-6-ethylpyrimidine-2,4-diamine | 5.38 | 6.56 | 14.95 |
| — | Trimetrexate: 5-methyl-6-(((3,4,5-trimethoxyphenyl)amino)methyl)quinazoline-2,4-diamine | 8.39 | 8.87 | 3.02 |
| 1 | 5-(4-(3,4-dichlorophenyl)piperazin-1-yl)pyrimidine-2,4-diamine | 7.12 | 7.86 | 5.5 |
| 2 | 5-(4-([1,1'-biphenyl]-3-yl)piperazin-1-yl)pyrimidine-2,4-diamine | 6.16 | 8.06 | 78.60 |
| 3 | 5-(4-(3-(trifluoromethyl)phenyl)piperazin-1-yl)pyrimidine-2,4-diamine | 6.27 | 7.21 | 8.71 |
| 4 | 5-(4-phenylpiperazin-1-yl)pyrimidine-2,4-diamine | 4.90 | 6.68 | 58.2 |
| 6 | 5-(4-(4-chlorophenyl)piperazin-1-yl)pyrimidine-2,4-diamine | 5.96 | 7.34 | 23.71 |
| 7 | 5-(4-(m-tolyl)piperazin-1-yl)pyrimidine-2,4-diamine | 5.22 | 7.12 | 79.43 |
| 11 | 5-(4-(3-bromophenyl)piperazin-1-yl)pyrimidine-2,4-diamine | 6.36 | 7.93 | 37.15 |
| 12 | 5-(4-([1,1'-biphenyl]-2-yl)piperazin-1-yl)pyrimidine-2,4-diamine | 5.75 | 7.51 | 57.99 |
| 15 | 5-(4-phenylpiperidin-1-yl)pyrimidine-2,4-diamine | 5.39 | 6.79 | 25.26 |
| 22 | 5-(4-(3-chlorophenyl)piperazin-1-yl)-6-methylpyrimidine-2,4-diamine | 6.62 | 8.09 | 29.68 |
| 47 | 6-methyl-5-(4-phenylpiperazin-1-yl)pyrimidine-2,4-diamine | 5.65 | 7.58 | 84.63 |

TABLE 11-continued

| | | Potency and Selectivity against *T. gondii* DHFR | | |
|---|---|---|---|---|
| No. | Compound Name | hDHFR pIC50 - DHFR primary assay | tgDHFR pIC50 - DHFR primary assay | Average DHFR selectivity (h/tg) |
| 26 | 5-(4-([1,1'-biphenyl]-3-yl)-3-methylpiperazin-1-yl)pyrimidine-2,4-diamine | 7.52 | 8.70 | 14.96 |
| 27 | 5-(4-([1,1'-biphenyl]-3-yl)-2-methylpiperazin-1-yl)pyrimidine-2,4-diamine | 4.52 | 6.86 | 218.78 |
| 28 | 6-ethyl-5-(4-phenylpiperazin-1-yl)pyrimidine-2,4-diamine | 5.87 | 8.24 | 235.78 |
| 31 | 6-ethyl-5-(4-(m-tolyl)piperazin-1-yl)pyrimidine-2,4-diamine | 6.38 | 8.46 | 119.54 |
| 33 | 6-ethyl-5-(4-(3-methoxyphenyl)piperazin-1-yl)pyrimidine-2,4-diamine | 6.28 | 8.36 | 120.23 |
| 34 | 6-ethyl-5-(4-(pyridin-2-yl)piperazin-1-yl)pyrimidine-2,4-diamine | 5.99 | 8.19 | 158.49 |
| 35 | 6-ethyl-5-(4-(4-fluorophenyl)piperazin-1-yl)pyrimidine-2,4-diamine | 5.85 | 8.16 | 204.17 |
| 36 | 6-ethyl-5-(4-(pyridin-4-yl)piperazin-1-yl)pyrimidine-2,4-diamine | 4.52 | 6.57 | 110.92 |
| 49 | 5-(4-phenylpiperazin-1-yl)-6-propylpyrimidine-2,4-diamine | 5.04 | 7.74 | 501.19 |
| 64 | 5-(4-(3'-fluoro-[1,1'-biphenyl]-3-yl)piperazin-1-yl)pyrimidine-2,4-diamine | 5.97 | 7.94 | 93.86 |
| 66 | 5-(4-(3-cyclopropylphenyl)piperazin-1-yl)pyrimidine-2,4-diamine | 5.79 | 7.54 | 56.23 |
| 67 | 3'-(4-(2,4-diaminopyrimidin-5-yl)piperazin-1-yl)-[1,1'-biphenyl]-3-carbonitrile | 6.52 | 8.41 | 77.18 |
| 103 | 5-(4-(3-(pyrimidin-2-yl)phenyl)piperazin-1-yl)pyrimidine-2,4-diamine | 5.89 | 7.56 | 47.50 |
| 104 | 5-(4-(3-(pyrazin-2-yl)phenyl)piperazin-1-yl)pyrimidine-2,4-diamine | 5.88 | 7.99 | 129.32 |
| 69 | 5-(4-(3-(2-methylpyrimidin-5-yl)phenyl)piperazin-1-yl)pyrimidine-2,4-diamine | 5.99 | 8.35 | 231.36 |
| 73 | 5-(4-(3-(pyridazin-4-yl)phenyl)piperazin-1-yl)pyrimidine-2,4-diamine | 5.96 | 8.22 | 184.08 |
| 74 | 5-(4-(3-(pyrimidin-5-yl)phenyl)piperazin-1-yl)pyrimidine-2,4-diamine | 5.84 | 8.32 | 302.00 |
| 78 | 5-(4-(3-(2-methoxypyrimidin-5-yl)phenyl)piperazin-1-yl)pyrimidine-2,4-diamine | 5.92 | 8.49 | 375.84 |
| 80 | 5-(4-(3-(2-methoxypyridin-3-yl)phenyl)piperazin-1-yl)pyrimidine-2,4-diamine | 5.99 | 8.21 | 165.32 |
| 95 | 5-(4-(3-(2-ethylpyrimidin-5-yl)phenyl)piperazin-1-yl)pyrimidine-2,4-diamine | 5.80 | 8.14 | 218.78 |
| 110 | 5-(4-(3-(tetrahydro-2H-pyran-4-yl)phenyl)piperazin-1-yl)pyrimidine-2,4-diamine | 5.21 | 7.46 | 177.83 |
| 113 | 5-(4-(3-(2-methylpyrimidin-5-yl)phenyl)piperidin-1-yl)pyrimidine-2,4-diamine | 6.43 | 8.21 | 59.91 |
| 96 | 5-(4-(3-(2-(dimethylamino)pyrimidin-5-yl)phenyl)piperazin-1-yl)pyrimidine-2,4-diamine | 5.94 | 8.00 | 115.48 |
| 51 | 5-(4-phenylpiperidin-1-yl)-6-propylpyrimidine-2,4-diamine | 5.61 | 7.93 | 241.03 |
| 52 | 5-(4-(4-fluorophenyl)piperazin-1-yl)-6-propylpyrimidine-2,4-diamine | 5.00 | 7.48 | 303.92 |

TABLE 11-continued

Potency and Selectivity against *T. gondii* DHFR

| No. | Compound Name | hDHFR pIC50 - DHFR primary assay | tgDHFR pIC50 - DHFR primary assay | Average DHFR selectivity (h/tg) |
|---|---|---|---|---|
| 97 | 5-(4-(3-(2-(methylamino)pyrimidin-5-yl)phenyl)piperazin-1-yl)pyrimidine-2,4-diamine | 6.13 | 8.25 | 131.33 |
| 98 | 5-(4-(3-(2-(azetidin-1-yl)pyrimidin-5-yl)phenyl)piperazin-1-yl)pyrimidine-2,4-diamine | 6.02 | 8.14 | 130.84 |
| 56 | 6-propyl-5-(4-(pyridin-2-yl)piperazin-1-yl)pyrimidine-2,4-diamine | 5.17 | 7.59 | 269.78 |
| 100 | 5-(4-(3-(2-chloropyrimidin-5-yl)phenyl)piperazin-1-yl)pyrimidine-2,4-diamine | 5.88 | 8.17 | 197.28 |
| 59 | 5-(4-(5-methylpyrimidin-2-yl)piperazin-1-yl)-6-propylpyrimidine-2,4-diamine | 5.09 | 7.15 | 118.81 |
| 39 | 6-ethyl-5-(4-(p-tolyl)piperazin-1-yl)pyrimidine-2,4-diamine | 5.76 | 7.91 | 144.58 |
| 60 | 5-(4-(5-methoxypyridin-2-yl)piperazin-1-yl)-6-propylpyrimidine-2,4-diamine | 5.54 | 7.70 | 149.75 |
| 25 | 5-(4-(3-morpholinophenyl)piperazin-1-yl)pyrimidine-2,4-diamine | 4.85 | 6.86 | 105.15 |
| 44 | 6-ethyl-5-(4-(5-fluoropyridin-2-yl)piperazin-1-yl)pyrimidine-2,4-diamine | 6.53 | 8.38 | 71.23 |
| 45 | 6-ethyl-5-(4-(5-methylpyridin-2-yl)piperazin-1-yl)pyrimidine-2,4-diamine | 6.10 | 8.23 | 136.15 |
| 106 | 6-(cyclopropylmethyl)-5-(4-phenylpiperazin-1-yl)pyrimidine-2,4-diamine | 5.23 | 7.56 | 218.96 |

TABLE 12

Potency and Selectivity against *T. cruzi* DHFR

| No. | Compound Name | hDHFR pIC$_{50}$ - DHFR primary assay | tcDHFR pIC$_{50}$ - DHFR primary assay | Average DHFR selectivity (h/tc) |
|---|---|---|---|---|
| — | Methotrexate: (4-(((2,4-diaminopteridin-6-yl)methyl)(methyl)amino)benzoyl)-L-glutamic acid | 8.27 | 8.96 | 4.9 |
| — | Pyrimethamine: 5-(4-chlorophenyl)-6-ethylpyrimidine-2,4-diamine | 5.39 | 6.00 | 4 |
| 4 | 5-(4-phenylpiperazin-1-yl)pyrimidine-2,4-diamine | 4.90 | 7.04 | 133 |
| 112 | 5-(4-(6-(trifluoromethyl)pyridin-3-yl)piperazin-1-yl)pyrimidine-2,4-diamine | 5.69 | 8.25 | 364 |
| 6 | 5-(4-(4-chlorophenyl)piperazin-1-yl)pyrimidine-2,4-diamine | 5.99 | 8.17 | 150 |
| 8 | 5-(4-(p-tolyl)piperazin-1-yl)pyrimidine-2,4-diamine | 5.58 | 7.74 | 146 |
| 114 | 5-(4-(4-methoxyphenyl)piperazin-1-yl)pyrimidine-2,4-diamine | 6.09 | 8.25 | 144 |
| 115 | 5-(4-(4-(trifluoromethyl)phenyl)piperazin-1-yl)pyrimidine-2,4-diamine | 6.09 | 8.21 | 132 |
| 9 | 5-(4-(3-methoxyphenyl)piperazin-1-yl)pyrimidine-2,4-diamine | 5.50 | 7.54 | 108 |
| 102 | 5-(4-(3-(pyrimidin-4-yl)phenyl)piperazin-1-yl)pyrimidine-2,4-diamine | 5.78 | 7.80 | 103 |

TABLE 12-continued

Potency and Selectivity against *T. cruzi* DHFR

| No. | Compound Name | hDHFR pIC$_{50}$ - DHFR primary assay | tcDHFR pIC$_{50}$ - DHFR primary assay | Average DHFR selectivity (h/tc) |
|---|---|---|---|---|
| 116 | 5-(4-(4-fluorophenyl)piperazin-1-yl)pyrimidine-2,4-diamine | 5.30 | 7.30 | 100 |

TABLE 13

Potency and Selectivity against *T. brucei* DHFR

| No. | Compound Name | hDHFR pIC$_{50}$ - DHFR primary assay | tbDHFR pIC$_{50}$ - DHFR primary assay | Average DHFR selectivity (h/tb)* - DHFR IC$_{50}$ |
|---|---|---|---|---|
| — | Methotrexate: (4-(((2,4-diaminopteridin-6-yl)methyl)(methyl)amino)benzoyl)-L-glutamic acid | 8.26 | 8.89 | 4.2 |
| — | Pyrimethamine: 5-(4-chlorophenyl)-6-ethylpyrimidine-2,4-diamine | 5.39 | 6.39 | 9.8 |
| 4 | 5-(4-phenylpiperazin-1-yl)pyrimidine-2,4-diamine | 4.90 | 7.50 | 400 |
| 87 | 5-(4-(3-(2-(trifluoromethyl)pyrimidin-5-yl)phenyl)piperazin-1-yl)pyrimidine-2,4-diamine | 5.26 | 8.13 | 739 |
| 74 | 5-(4-(3-(pyrimidin-5-yl)phenyl)piperazin-1-yl)pyrimidine-2,4-diamine | 5.51 | 8.25 | 550 |
| 100 | 5-(4-(3-(2-chloropyrimidin-5-yl)phenyl)piperazin-1-yl)pyrimidine-2,4-diamine | 5.88 | 8.60 | 522 |
| 78 | 5-(4-(3-(2-methoxypyrimidin-5-yl)phenyl)piperazin-1-yl)pyrimidine-2,4-diamine | 6.05 | 8.68 | 420 |
| 69 | 5-(4-(3-(2-methylpyrimidin-5-yl)phenyl)piperazin-1-yl)pyrimidine-2,4-diamine | 6.10 | 8.70 | 401 |
| 95 | 5-(4-(3-(2-ethylpyrimidin-5-yl)phenyl)piperazin-1-yl)pyrimidine-2,4-diamine | 5.85 | 8.42 | 375 |
| 94 | 5-(4-(3-(2-ethylpyrimidin-5-yl)phenyl)piperidin-1-yl)pyrimidine-2,4-diamine | 6.49 | 9.05 | 357 |
| 86 | 5-(4-(3-(2-cyclopropylpyrimidin-5-yl)phenyl)piperazin-1-yl)pyrimidine-2,4-diamine | 6.08 | 8.60 | 330 |

TABLE 14

Potency and Selectivity against *L. major* DHFR

| No. | Compound Name | hDHFR pIC$_{50}$ - DHFR primary assay | lmDHFR pIC$_{50}$ - DHFR primary assay | Average DHFR selectivity (h/lm)* - DHFR IC$_{50}$ |
|---|---|---|---|---|
| — | Methotrexate: (4-(((2,4-diaminopteridin-6-yl)methyl)(methyl)amino)benzoyl)-L-glutamic acid | 8.28 | 8.64 | 2.3 |
| — | Pyrimethamine: 5-(4-chlorophenyl)-6-ethylpyrimidine-2,4-diamine | 5.41 | 5.25 | 0.7 |
| 4 | 5-(4-phenylpiperazin-1-yl)pyrimidine-2,4-diamine | 4.90 | 6.30 | 25.1 |
| 6 | 5-(4-(4-chlorophenyl)piperazin-1-yl)pyrimidine-2,4-diamine | 6.31 | 8.12 | 65 |

TABLE 14-continued

Potency and Selectivity against *L. major* DHFR

| No. | Compound Name | hDHFR pIC$_{50}$ - DHFR primary assay | lmDHFR pIC$_{50}$ - DHFR primary assay | Average DHFR selectivity (h/lm)* - DHFR IC$_{50}$ |
|---|---|---|---|---|
| 98 | 5-(4-(3-(2-(azetidin-1-yl)pyrimidin-5-yl)phenyl)piperazin-1-yl)pyrimidine-2,4-diamine | 5.86 | 7.54 | 48 |
| 73 | 5-(4-(3-(pyridazin-4-yl)phenyl)piperazin-1-yl)pyrimidine-2,4-diamine | 5.80 | 7.44 | 44 |
| 19 | 5-(4-(quinolin-3-yl)piperazin-1-yl)pyrimidine-2,4-diamine | 6.89 | 8.43 | 35 |
| 110 | 5-(4-([2,4'-bipyridin]-4-yl)piperazin-1-yl)pyrimidine-2,4-diamine | 6.57 | 8.10 | 34 |
| 107 | 5-(4-(3-(pyridazin-3-yl)phenyl)piperazin-1-yl)pyrimidine-2,4-diamine | 5.80 | 7.28 | 30 |
| 12 | 5-(4-([1,1'-biphenyl]-4-yl)piperazin-1-yl)pyrimidine-2,4-diamine | 6.67 | 8.13 | 29 |
| 90 | 5-(4-(3-(2-fluoropyridin-4-yl)phenyl)piperazin-1-yl)pyrimidine-2,4-diamine | 5.94 | 7.37 | 27 |

TABLE 15

Potency and Selectivity against *P. Falciparum* DHFR

| No. | Compound Name | hDHFR pIC$_{50}$ - DHFR primary assay | pfDHFR pIC$_{50}$ - DHFR primary-assay | Average DHFR selectivity (h/pf)* - DHFR IC$_{50}$ |
|---|---|---|---|---|
| — | Methotrexate: (4-(((2,4-diaminopteridin-6-yl)methyl)(methyl)amino)benzoyl)-L-glutamic acid | 8.27 | 9.05 | 6 |
| — | Pyrimethamine: 5-(4-chlorophenyl)-6-ethylpyrimidine-2,4-diamine | 5.39 | 8.28 | 760 |
| 4 | 5-(4-phenylpiperazin-1-yl)pyrimidine-2,4-diamine | 4.90 | 8.72 | 6660 |
| 110 | 5-(4-(3-(tetrahydro-2H-pyran-4-yl)phenyl)piperazin-1-yl)pyrimidine-2,4-diamine | 5.11 | 8.96 | 7,100 |
| 78 | 5-(4-(3-(2-methoxypyrimidin-5-yl)phenyl)piperazin-1-yl)pyrimidine-2,4-diamine | 6.04 | 9.15 | 1,300 |
| 49 | 5-(4-phenylpiperazin-1-yl)-6-propylpyrimidine-2,4-diamine | 4.95 | 7.85 | 806 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound having the structure of formula (I) or a pharmaceutically acceptable salt thereof:

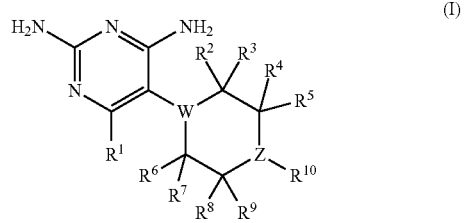

(I)

wherein:

R$^1$ is H, C$_{1-6}$ alkyl, C$_{3-6}$ cycloalkyl, C$_{4-8}$ cycloalkylalkyl, or halogen;

W is N or CR$^{18}$ and Z is N or CR$^{17}$, provided that at least one of W and Z is N;

R$^2$, R$^3$, R$^4$, R$^5$, R$^6$, R$^7$, R$^8$, R$^9$, R$^{17}$, and R$^{18}$ are independently selected from H, C$_{1-6}$ alkyl, C$_{3-6}$ cycloalkyl, hydroxyl or fluorine; provided that at least four of R$^2$, R$^3$, R$^4$, R$^5$, R$^6$, R$^7$, R$^8$, and R$^9$ are H; if W is N, then none of R$^2$, R$^3$, R$^6$, and R$^7$ is hydroxyl; and if Z is N, then none of R$^4$, R$^5$, R$^8$, and R$^9$ is hydroxyl;

R$^{10}$ is substituted or unsubstituted C$_{6-10}$ aryl or 5- to 10-membered heteroaryl;

provided that:
a. Z is CR$^{17}$;
b. at least one of R$^2$, R$^3$, R$^4$, R$^5$, R$^6$, R$^7$, R$^8$, and R$^9$ is C$_{1-6}$ alkyl, C$_{3-6}$ cycloalkyl, or halogen;
c. R$^1$ is C$_{4-6}$ alkyl, C$_{3-6}$ cycloalkyl, C$_{4-8}$ cycloalkylalkyl, or fluoro;
d. R$^{10}$ is substituted or unsubstituted 5- to 10-membered heteroaryl or C$_{10}$ aryl;
e. Z and W are N and R$^{10}$ is phenyl substituted at the meta or ortho position with at least one substituent selected from chloro, alkoxy, phosphoryl, phosphate, phosphonate, phosphinate, amino, amidine, imine, cyano, azido, sulfhydryl, or alkylthio, heterocyclyl, aralkyl, aryl, or heteroaryl;
f. R$^{10}$ is phenyl substituted with R$^{12}$ or X—R$^{12}$; or
g. R$^1$ is C$_{3-6}$ alkyl and R$^{10}$ is phenyl optionally substituted with halogen, hydroxyl, alkoxy, phosphoryl, phosphate, phosphonate, phosphinate, amino, amidine, imine, azido, sulfhydryl, or alkylthio; and further wherein:
each instance of R$^{12}$ is independently selected from substituted or unsubstituted phenyl, 5- or 6-membered heteroaryl, or 4 to 7-membered heterocyclyl;
each instance of X is independently selected from carbonyl, Y, —CH$_2$Y—, or —YCH$_2$—;
each instance of Y is independently selected from —CH$_2$—, —O—, —S—, or —NR$^{13}$—; and
each instance of R$^{13}$ is independently H or C$_{1-6}$ alkyl.

2. The compound of claim 1, wherein the compound has the structure of formula (Ia):

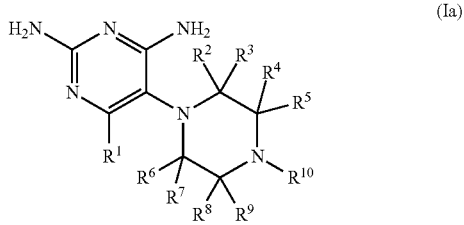

(Ia)

wherein:
R$^1$ is H, C$_{1-6}$ alkyl, C$_{3-6}$ cycloalkyl, or halogen;
R$^2$, R$^3$, R$^4$, R$^5$, R$^6$, R$^7$, R$^8$, and R$^9$ are independently selected from H, C$_{1-6}$ alkyl, C$_{3-6}$ cycloalkyl, or fluorine, provided that at least four of R$^2$, R$^3$, R$^4$, R$^5$, R$^6$, R$^7$, R$^8$, and R$^9$ are H; and
R$^{10}$ is substituted or unsubstituted C$_{6-10}$ aryl or 5- to 10-membered heteroaryl;

provided that:
a. at least one of R$^2$, R$^3$, R$^4$, R$^5$, R$^6$, R$^7$, R$^8$, and R$^9$ is C$_{1-6}$ alkyl, C$_{3-6}$ cycloalkyl, or halogen;
b. R$^1$ is C$_{4-6}$ alkyl, C$_{3-6}$ cycloalkyl, or fluoro;
c. R$^{10}$ is substituted or unsubstituted 5- to 10-membered heteroaryl or C$_{10}$ aryl;

d. R$^{10}$ is phenyl substituted at the meta or ortho position with at least one substituent selected from chloro, alkoxy, phosphoryl, phosphate, phosphonate, phosphinate, amino, amidine, imine, cyano, azido, sulfhydryl, or alkylthio, heterocyclyl, aralkyl, aryl, or heteroaryl;

e. R$^{10}$ is phenyl substituted with R$^{12}$ or X—R$^{12}$.

3. The compound of claim 1, wherein R$^{10}$ is C$_{6-10}$ aryl or 5- to 10-membered heteroaryl, and is optionally substituted with a substituent selected from alkyl, cycloalkyl, halogen, hydroxyl, alkoxy, cycloalkyloxy, cycloalkylalkyl, cycloalkylalkoxy, phosphoryl, phosphate, phosphonate, phosphinate, amino, amidine, imine, cyano, azido, sulfhydryl, or alkylthio, heterocyclyl, aralkyl, or an aromatic or heteroaromatic moiety.

4. The compound of claim 1, wherein R$^{10}$ is substituted with at least one substituent selected from alkyl, cycloalkyl, halogen, hydroxyl, alkoxy, cycloalkyloxy, cycloalkylalkyl, cycloalkylalkoxy, phosphoryl, phosphate, phosphonate, phosphinate, amino, amidine, imine, cyano, azido, sulfhydryl, or alkylthio, heterocyclyl, aralkyl, or an aromatic or heteroaromatic moiety.

5. The compound of claim 1, wherein R$^1$ is H, C$_{1-3}$ alkyl, C$_{3-5}$ cycloalkyl, C$_{4-6}$ cycloalkylalkyl, or halogen.

6. The compound of claim 1, wherein R$^{10}$ is substituted or unsubstituted C$_{6-10}$ aryl or 5- to 10-membered heteroaryl, and is further substituted with R$^{12}$ or X—R$_{12}$.

7. The compound of claim 6, wherein R$^{10}$ is phenyl.

8. The compound of claim 7, wherein R$^{10}$ is phenyl substituted with R$^{12}$ at the meta position.

9. The compound of claim 1, wherein the substituents on each instance of R$^{12}$ are selected from hydroxy, C$_{1-6}$ alkyl, C$_{1-6}$ alkoxy, C$_{3-7}$ alkoxyalkoxy, C$_{1-6}$ haloalkyl, C$_{1-6}$ haloalkyloxy, C$_{3-7}$ haloalkoxyalkoxy, C$_{3-6}$ cycloalkyl, C$_{3-6}$ cycloalkyloxy, C$_{4-8}$ cycloalkylalkyloxy, C$_{4-8}$ cycloalkylalkyl, 4 to 7-membered heterocyclyl, 4 to 7-membered heterocyclyloxy, halo, cyano, oxo, or amino optionally substituted with up to 2 C$_{1-6}$ alkyl or C$_{3-6}$ cycloalkyl.

10. The compound of claim 9, wherein the substituents on each instance of R$^{12}$ are selected from C$_{1-6}$ alkyl, C$_{3-6}$ cycloalkyl, halo, cyano, or oxo.

11. The compound of claim 9, wherein the substituents on each instance of R$^{12}$ are selected from C$_{1-6}$ alkoxy.

12. The compound of claim 1, wherein R$^1$ is H, and R$^{10}$ is substituted or unsubstituted phenyl.

13. The compound of claim 7, wherein:
R$^{10}$ is substituted with R$^{12}$ and is optionally substituted with one or more substituents independently selected from R$^{11}$;
each instance of R$^{11}$ is independently selected from C$_{1-6}$ alkyl, C$_{1-6}$ alkoxy, C$_{2-6}$ alkoxyalkyl, cyano, or halogen.

14. The compound of claim 13, wherein R$^{12}$ is substituted or unsubstituted phenyl, 5- or 6-membered heteroaryl, or 4- to 7-membered heterocyclyl and is substituted with methyl, ethyl, methoxy, or trifluoromethyl.

15. The compound of claim 13, wherein R$^1$ is H.

16. The compound of claim 9, wherein R$^{10}$ is phenyl substituted with R$^{12}$.

17. The compound of claim 9, wherein R$^{12}$ is pyrimidin-5-yl or pyridin-3-yl.

18. The compound of claim 9, wherein $R^{12}$ is 2-methoxy-pyrimidin-5-yl, 3-methoxyphenyl, 2-methoxy-pyridin-3-yl, 2-methyl-pyrimidin-5-yl, or tetrahydropyran-4-yl.

19. The compound of claim 18, wherein the compound has one of the following structures or is a pharmaceutically acceptable salt thereof:

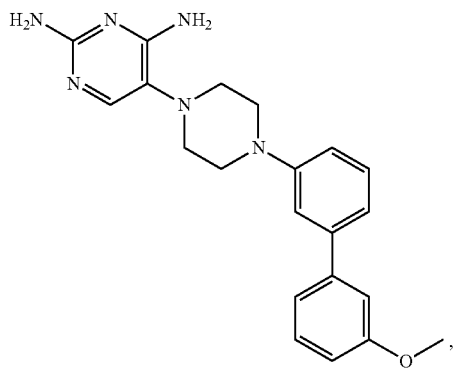

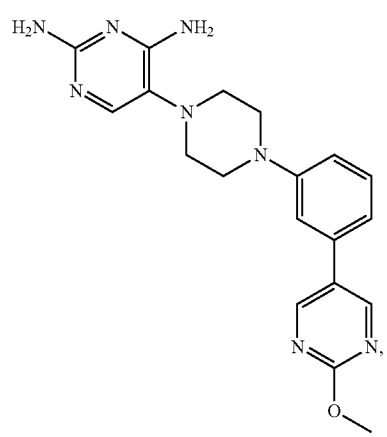

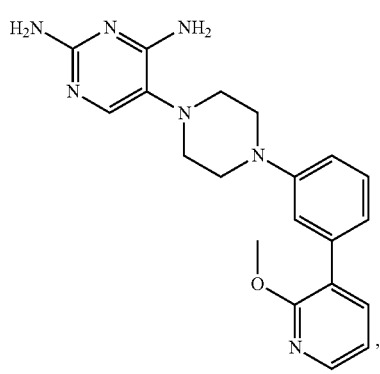

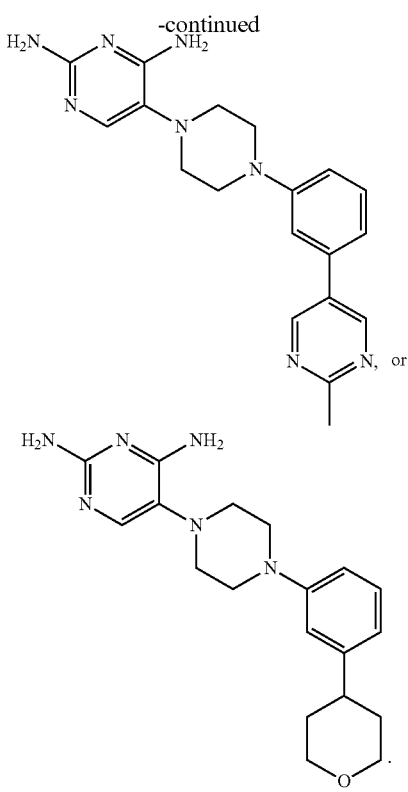

20. A pharmaceutical composition comprising a compound of claim 1.

21. A method of treating toxoplasmosis, comprising administering to a patient in need thereof a compound having the structure of formula (I), a pharmaceutically acceptable salt thereof, or a pharmaceutical composition comprising the compound or salt:

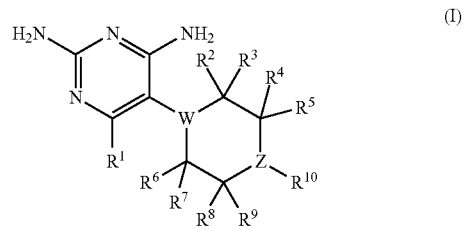

(I)

wherein:
$R^1$ is H, $C_{1-6}$ alkyl, $C_{3-6}$ cycloalkyl, $C_{4-8}$ cycloalkylalkyl, or halogen;
W is N or $CR^{18}$ and Z is N or $CR^{17}$, provided that at least one of W and Z is N;
$R^2$, $R^3$, $R^4$, $R^5$, $R^6$, $R^7$, $R^8$, $R^9$, $R^{17}$, and $R^{18}$ are independently selected from H, $C_{1-6}$ alkyl, $C_{3-6}$ cycloalkyl, hydroxyl or fluorine; provided that at least four of $R^2$, $R^3$, $R^4$, $R^5$, $R^6$, $R^7$, $R^8$, and $R^9$ are H; if W is N, then none of $R^2$, $R^3$, $R^6$, and $R^7$ is hydroxyl; and if Z is N, then none of $R^4$, $R^5$, $R^8$, and $R^9$ is hydroxyl; and
$R^{10}$ is substituted or unsubstituted $C_{6-10}$ aryl or 5- to 10-membered heteroaryl.

* * * * *

UNITED STATES PATENT AND TRADEMARK OFFICE
CERTIFICATE OF CORRECTION

PATENT NO. : 10,774,073 B2
APPLICATION NO. : 16/075924
DATED : September 15, 2020
INVENTOR(S) : Stephen B. Thomas et al.

It is certified that error appears in the above-identified patent and that said Letters Patent is hereby corrected as shown below:

In the Claims

At Column 94, Claim number 2, Line number 5, please replace:
"or alkylthio, heterocyclyl, aralkyl, aryl, or heteroaryl;"
With:
-- or alkylthio, heterocyclyl, aralkyl, aryl, or heteroaryl; or --.

At Column 94, Claim number 6, Line number 29, please replace:
"and is further substituted with $R^{12}$ or $X-R_{12}$"
With:
-- and is further substituted with $R^{12}$ or $X-R^{12}$ --.

Signed and Sealed this
Eighth Day of December, 2020

Andrei Iancu
*Director of the United States Patent and Trademark Office*